US006238676B1

(12) United States Patent
Porcelli et al.

(10) Patent No.: US 6,238,676 B1
(45) Date of Patent: *May 29, 2001

(54) PRESENTATION OF HYDROPHOBIC ANTIGENS TO T-CELLS BY CD1 MOLECULES

(75) Inventors: Steven A. Porcelli, Bronx, NY (US); Michael B. Brenner, Newton; Evan M. Beckman, Sudbury, both of MA (US); Stephen T. Furlong, Wilmington, DE (US)

(73) Assignee: Brigham and Women's Hospital, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/501,600

(22) Filed: Jul. 12, 1995

Related U.S. Application Data

(63) Continuation-in-part of application No. 08/322,980, filed on Oct. 13, 1994, now Pat. No. 5,679,347, which is a continuation of application No. 08/322,979, filed on Oct. 13, 1994, now Pat. No. 5,853,737, which is a continuation-in-part of application No. PCT/US94/06991, filed on Jun. 21, 1994, which is a continuation-in-part of application No. 08/080,072, filed on Jun. 21, 1993, now abandoned, which is a continuation-in-part of application No. 07/989,790, filed on Dec. 10, 1992, now abandoned.

(51) Int. Cl.[7] ............................. A61K 39/04; C07K 14/00
(52) U.S. Cl. .................................... 424/248.1; 424/282.1; 530/351
(58) Field of Search .............................. 424/185.1, 193.1, 424/245.1, 282.1; 530/300, 350, 395, 565, 351

(56) References Cited

U.S. PATENT DOCUMENTS

| | | | |
|---|---|---|---|
| 4,329,452 | * | 5/1982 | Maruyama . |
| 4,394,502 | * | 7/1983 | Maruyama . |
| 4,455,142 | * | 6/1984 | Martins et al. . |
| 5,296,466 | | 3/1994 | Kilbourn et al. . |
| 5,679,347 | * | 10/1997 | Porcelli et al. . |
| 5,853,737 | | 12/1998 | Modlin et al. . |

FOREIGN PATENT DOCUMENTS

| | | |
|---|---|---|
| 0 604 727 | 7/1994 | (EP) . |
| WO 90/00594 | 1/1990 | (WO) . |
| WO 92/01796 | 2/1992 | (WO) . |
| WO 92/14154 | 8/1992 | (WO) . |
| WO 92/14155 | 8/1992 | (WO) . |
| WO 95/00163 | 1/1995 | (WO) . |
| WO 96/12190 | 4/1996 | (WO) . |
| WO 98/39025 | 9/1998 | (WO) . |
| WO 99/12562 | 3/1999 | (WO) . |
| WO 99/15199 | 4/1999 | (WO) . |

OTHER PUBLICATIONS

Porcelli, S.A. Advs. Immunol. vol. 59, pp. 1098, 1995.*
Porcelli, SA., Current Opin. Immunol. vol. 5, pp. 510–516, 1996.*
Lederer, Springer Semin. Immunopathol. vol. 2, pp. 133–148, 1979.*
Bekierkunst et al. Infection and Immunity. vol. 10(5), pp. 1044–1050, 1974.*
Morita. Eur. J. Immunol. vol. 21, pp. 2999–3007, 1991.*
Campbell, A.M. Monoclonal antibody technology, Elservier Sci Publ. Co., Inc. NY, pp. 1–32, 1984.*
Male, D.A. Immunology, An Illustrated Guide, C.V. Mosby co., Gower Med. Publ., London/NY, p. 55, 1986.*
Favoloro et al., Leukocyte Typing III, Chapter T1.4—Heterogeneity of Antigens within CD1, Ed. A.J. McMichael, (1987), pp. 77–79.
Favoloro et al., "Characterization of a p43 Human Thymocyte Antigen," Disease Markers, (1986) vol. 4, pp. 261–270.
Minnikin, D.E., Chapter 4, "Lipids: Complex Lipids, Their Chemistry, Biosynthesis and Roles," *The Biology of the Mycobacteria*, vol. 1 Physiology, Identification and Classification edited by Ratledge, C. et al., 1982.
White R.G., "Characterization of Microbacterial Components of Adjuvant Mixtures," *Sympos. Series Immunobiol. Standard*, 6:49–58 (1967).
Allison, A.C., et al., "Immunological Adjuvants: Desirable Properties and Side–Effects," *Mol. Immunology*, 28:279–284 (1991).
Porcelli, S.A., et al., "T–Cell Recognition of Non–Peptide Antigens," *Current Opinion in Immunology*, 8:510–516 (1996).
Gong J. et al., "Isolation of Mycobacterium–Reactive CD1–restricted T Cells from Patients with Human Immunodeficiency Virus Infection," *J. Clin. Invest.* 101:383–389 (1998).

(List continued on next page.)

Primary Examiner—Christina Y. Chan
Assistant Examiner—Marianne DiBrino
(74) Attorney, Agent, or Firm—Wolf, Greenfield & Sacks, PC

(57) ABSTRACT

Provided are CD-1 presented antigens, compositions, cells, inhibitors and methods relating to the use of hydrophobic antigen presentation by CD1 molecules, including:

methods for detecting the presence of a CD1-presented hydrophobic antigen in a sample;

methods for isolating such CD1-presented antigens and the isolated antigens;

vaccines containing CD1-presented antigens and vaccination methods;

methods of blocking CD1 antigen presentation;

methods of identifying and/or isolating CD1 blocking agents and the isolated CD1 blocking agents;

methods of inducing CD1 expression; and

T-cells for use in the methods disclosed.

28 Claims, 36 Drawing Sheets

OTHER PUBLICATIONS

Dorman S.E., et al., "Adjunctive Corticosteroid Therapy for Patients Whose Treatment for Disseminated *Mycobacterium Avium* Complex Infection Has Failed," *Clinical Infectious Diseases*, 26:682–686 (1998).

Giuliani A., et al., "Effect of Firampin on CD1b Expression and Double–Negative T Cell Response Against Mycobacteria–Derived Glycolipid Antigen," *Life Sciences* 63(12):985–994 (1998).

Haq, T.A., "Oral Immunization with a Recombinant Bacterial Antigen Produced in Transgenic Plants," *Science*, 268:714–716 (1995).

Hochstenbach, F. et al., "Endoplasmic Reticulum Resident Protein of 90 Kilodaltons Associates with the T– and B–Cell Antigen Receptors and Major Histocompatibility Complex Antigens During Their Assembly," *Proc. Natl. Acad. Sci. USA*, 89:4734–4738 (1992).

Porcelli S. et al., "Analysis of T Cell Antigen Receptor (TCR) Expression by Human Peripheral Blood $CD4^- 8^-\alpha/\beta$ T Cells Demonstrates Preferential Use of Several V$\beta$ Genes and an Invariant TCR $\alpha$ Chain," *J. Exp. Med.* 178:1–16 (1993).

Constant, P. et al., "Stimulation of Human $\gamma\delta$ T Cells by Nonpeptidic Mycobacterial Ligands," *Science*, 264:267–270 (1994).

Singh, A.P., et al., "Enhancement of Immunogenicity of an Immunoprotective Glycophospholipid Antigen of Mycobacteria Using Liposomes Containing Lipid A," *Journal of Liposome Research*, 3(2):303–316 (1993).

Talwar, G.P., et al., "Present Approaches to Immunotherapy and Immunoprophylaxis for Leprosy," Chapter 28, In Prog. Vaccin. 2:301–311 (1989).

Minnikin, D.E. et al., "Mycolipenates and Mycolipanolates of Trehalose from *Mycobacterium tuberculosis*," *Journal of General Microbiology*, 131:1369–1374 (1985).

Minnikin, D.E. et al., "Mycolic Acid Patterns for Four Vaccine Strains of *Mycobacterium bovis* BCG," *Journal of General Microbiology*, 129:889–891 (1983).

Orbach–Arbouys, S. et al., "Enhancement of In Vitro and In Vivo Antitumor Activity by Cord Factor (6–6'–Dimycolate of Trehalose) Administered Suspended in Saline," *Int. Archs Allergy appl. Immun.* 71:67–73 (1983).

Salamone, M.d.C. et al., "Intracellular Expression of CD1 Molecules on PHA–Activated Normal T Lymphocytes," *Immunology Letters*, 32:111–116 (1992).

Saito, R. et al., Adjuvanticity (Immunity–Inducing Property) of Cord Factor in Mice and Rats, *Infection and Immunity*, 16(3):725–729 (1977).

Masihi, K.N., et al., "Stimulation of Nonspecific Resistance Against Aerogenic Viral and Bacterial Infections by Muramyl Dipeptide Combined with Trehalose Dimycolate," *Biological Properties of Peptidoglycan*, pp. 401–406 (1986).

Kato, M., "Effect of Anti–Cord Factor Antibody on Experimental Tuberculosis in Mice," *Infection and Immunity*, 7(1):14–21 (1973).

Kato, M., Site II–Specific Inhibition of Mitochondrial Oxidative Phosphorylation by Trehalose–6,6'–dimycolate (Cord Factor) of *Mycobacterium tuberculosis*, 140:379–390 (1970).

Ellner, J.J., et al., "Immunosuppression by Mycobacterial Arabinomannan," *Clin. Exp. Immunol.*, 35:250–257 (1979).

Misaki, A., et al., "Structural and Immunochemical Studies on D–Arabino–D–Mannans and D–Mannans of *Mycobacterium Tuberculosis* and Other Mycobacterium Species," *J. Biochem.* 82:1759–1770 (1977).

Misaki, A., et al., "Structure and Immunological Properties of D–Arabino–D–galactans Isolated from Cell Walls of Mycobacterium Species," *J. Biochem.* 76:15–27 (1974).

Hacker, G., et al., "Opportunist Mycobacteria Express Ligands that Stimulate Production of Human V$\gamma$9V$\gamma$2 T Lymphocytes," *Infection and Immunity*, 60(7):2753–2757 (1992).

Pfeffer, K. et al., "A Lectin–Binding, Protease–Resistant Mycobacterial Ligand Specifically Activates $V\gamma9^+$ Human $\gamma\delta$ T Cells," *The Journal of Immunology*, 148(2):575–583 (1992).

Cruaud, P., et al., "Evaluation of a Novel 2,3–Diacyl–Trehalose–2'–Sulphate (SL–IV) Antigen for Case Finding and Diagnosis of Leprosy and Tuberculosis," *Res. Microbiol.* 141:679–694 (1990).

Azuma, I. et al., "Chemical Synthesis and Biological Activities of 6,6'–di–O–my–coloyl–$\beta,\beta$– and –$\alpha$, $\beta$–trehalose," *Carbohydrate Research*, 212:47–53 (1991).

Horwitz, M.A., et al., "Protective Immunity Against Tuberculosis Induced by Vaccination with Major Extracellular Proteins Of *Mycobacterium tuberculosis*," *Proc. Natl. Acad. Sci. USA*, 92:1530–1534 (1995).

Lemassu, A., et al., "Revised Structure of a Trehalose–Containing Immunoreactive Glycolipid of *Mycobacterium Tuberculosis*," *FEMS Microbiology Letters*, 78:171–176 (1991).

Leclerc, C. et al., "Nonspecific Immunoprevention of L1210 Leukemia by Cord Factor (6–6' Dimycolate of Trehalose) Administered in a Metabolizable Oil," *Cancer Immunol. Immunother.*, 1:227–232 (1976).

Mehta, P.K., et al., "Immunogenicity of Mannophosphoinositides of Mycobacteria: Effect of Cord Factor (Trehalose–6–6'–Dimycolate)," *Folia Microbiol.*, 35:570–577 (1990).

Parant, M. et al., "Nonspecific Immunostimulant Activities of Synthetic Trehalose–6–6'–Diesters (Lower Homologs of Cord Factor)," *Infection and Immunity*, 20(1):12–19 (1978).

Bekierkunst, A., et al., "Immune Response to Sheep Red Blood Cells in Mice Pretreated with Mycobacterial Fractions," *Infection and Immunity*, 4(3):256–263 (1971).

Batra, J.K., et al., "Effect of Cord Factor, A Toxic Glycolipid from *Mycobacterium Tuberculosis*, on Mouse Liver Drug Metabolizing Enzymes," *Toxicon*, 25(3):345–349 (1987).

Daffe, M. et al., "Novel Type–Specific Lipooligosaccharides from *Mycobacterium tuberculosis*," *Biochemistry*, 30:378–388 (1991).

Kasprzak, A.A., et al., "Location of a Contact Site Between Actin and Myosin in the Three–Dimensional Structure of the Acto–S1 Complex," *Biochemistry*, 28:9230–9238 (1989).

Takayama, K., et al., Chapter 13, "Structure and Synthesis of Lipids," *The Mycobacteria—A SourceBook*, Part A, edited by Kubica, G.P. et al., pp. 315–344 (1984).

Bloom, B.R., et al., "Tuberculosis: Commentary on a Reemergent Killer," *Science*, 257:1055–1064 (1992).

Stahl, D.A., "The Division Between Fast– and Slow–Growing Species Corresponds to Natural Relationships Among the Mycobacteria," *Journal of Bacteriology*, 172(1):116–124 (1990).

Cerundolo, V., et al., "Presentation of Viral Antigen Controlled by a Gene in the Major Histocompatibility Complex," *Letters to Nature*, 345:449–452 (1990).

Lotteau, V., et al., "Intracellular Transport of Class II MHC Molecules Directed by Invariant Chain," *Nature*, 348:600–605 (1990).

Theodorou, I.D., et al., "CD1 Stimulation of Human T Cell Lines Induces a Rapid Increase in the Intracellular Free $Ca^{2+}$ Concentration and the Production of IL–$2^1$," *The Journal of Immunology*, 144(7):2518–2523 (1990).

Yewdell, J.W., et al., "The Binary Logic of Antigen Processing and Presentation to T Cells," *Cell*, 62:203–206 (1990).

Orlandi, P.A., et al., "Structure of Lipid Moiety of the *Leishmania donovani* Lipophosphoglycan," *The Journal of Biological Chemistry*, 262(21):10384–10391 (1987).

Bukowski, J.F., et al., "Vγ2Vδ2 TCR–Dependent Recognition of Non–Peptide Antigens and Daudi Cells Analyzed by TCR Gene Transfer," *The Journal of Immunology*, 154:998–1006 (1995).

Ishioka, G.Y., et al., "MHC Interaction and T Cell Recognition of Cabohydrafts and Glycopeptides," *The Journal of Immunology*, 148(8):2446–2451 (1992).

Harding, C.V., et al., "Glypeptides Bind MHC Molecules and Elicit Specific T Cell Responses," *The Journal of Immunology*, 151(5):2419–2425 (1993).

Hunter, S.W., et al., "The Major Native Proteins of the Leprosy Bacillus," *The Journal of Biological Chemistry*, 265(24):14065–14068 (1990).

Salgame, P. et. al., "Differing Lymphokine Profiles of Functional Subsets of Human CD4 and CD8 T Cell Clones," *Science*, 254:279–282 (1991).

Wang, X. et al., T Cells Bearing Vβ6 T Cell Receptors in the Cell–Mediated Immune Response to *Mycobacterium leprae*, *The Journal of Immunology*, 151(12):7105–7116 (1993).

Sieling, P.A., "Immunosuppressive Roles for IL–10 and IL–4 in Human Infection," *The Journal of Immunology*, 150(12):5501–5510 (1993).

Beckman, E.M., et al., "MHC Class I–Like, Class II–Like and CD1 Molecules: Distinct Roles in Immunity," *Immunology Today*, 16(7);349–352 (1995).

Beckman, E.M., et al., "CD1c Restricts Responses of Mycobacteria–Specific T Cells," *The Journal of Immunology*, 157:2795–2803 (1996).

Moody, D.B., et al., "The CD1–Restricted T–Cell Response to Mycobacteria," *Res. In Immunology*, 147(8–9):550–9 (1996).

Moody, D.B., et al., "Structural Requirements for Glycolipid Antigen Recognition by CD1b–Restricted T Cells," *Science*, 278:283–286 (1997).

Calabi, F., et al., "Two Classes of CD1 Genes," *Eur. J. Immunol.*, 19:285–292 (1989).

Porcelli, S.A., "The CD1 Family: A Third Lineage of Antigen–Presenting Molecules," *Advances in Immunology*, 59:1–98 (1995).

D'Erchia, A.M., et al., "The Guinea–Pig Is Not a Rodent," *Nature*, 381:597–600 (1996).

Ribi, E., et al., "Immunopotentiating Activities of Monophosphoryl Lipid A," *Immunopharmacology of Infectious Diseases: Vaccine Adjuvants and Modulators of Non–Specific Resistance*, pp. 101–112 (1987).

Uyemura, K., et al., "Selective Expansion of Vδ1 + T–Cells from Leprosy Skin Lesions," *J. Invest. Dermatol.* 99:848–852 (1992).

Sakamoto, A., et al., "T Cell Receptor Vβ Repertoire of Double–Negative α/β T Cells in Patients with Systemic Sclerosis," *Arthritis and Rheumatism*, 35(8):944–948 (1992).

Tanaka, Y., et al., "Nonpeptide Ligands for Human γδ T Cells," *Proc. Natl. Acad. Sci. USA*, 91:8175–8179 (1994).

Zeng, Z–H., et al., "Crystal Structure of Mouse CD1: An MHC–Like Fold with a Large Hydrophobic Binding Groove," *Science*, 277:339–345 (1997).

Besra, G.S., et al., "Identification of the Apparent Carrier in Mycolic Acid Synthesis," *Proc. Natl. Acid. Sci. USA*, 91:12735–12739 (1994).

Rush, J.S., et al., "Mannosylphosphoryldolichol–Mediated Reactions in Oligosaccharide–P–P–Dolichol Biosynthesis," *The Journal of Biological Chemistry*, 268(18):13110–13117 (1993).

Krag, S.S., "Breakthroughs and Views—The Importance of Being Dolichol," *Biochemical and Biophysical Research Communications*, 243:1–5 (1998).

Wolinsky, E., Chapter 37, "Mycobacteria," *Microbiology Including Immunology and Molecular Genetics*, Third Edition, (1980) by Harper & Row, Publishers, Inc., pp. 724–742.

Anthony, L.S.D., et al., "Lipoarabinomannan from *Mycobacterium tuberculosis* Modulates the Generation of Reactive Nitrogen Intermediates by Gamma Interferon–Activated Macrophages," *FEMS Immunology and Medical Microbiology*, 8:299–306 (1994).

Parham, P., "Chewing the Fat," *Nature*, 372:615–616 (1994).

Porcelli, S.A., "Presentation of Lipid Antigens to T Cells by the CD1 System," Abstract of Cellular Immunology and the Immunotherapy of Cancer–III (Keystone Meeting Presentation) in Copper Mountain, Co. (1997).

Roncarolo, M.G., et al., "Antigen Recognition by MHC–Incompatible Cells of a Human Mismatched Chimera," *J. Exp. Med.*, 168:2139–2152 (1988).

Calabi, F., et al., Chapter 8, "CD1: From Structure to Function," *Immunogenetics of the Major Histocompatibility Complex*, edited by Srivastava, R., et al., (1991).

Howard, C.J., et al., "6.3 Comparison of CD1 Monoclonal Antibodies on Bovine Cells and Tissues," *Veterinary Immunology and Immunopathology*, 39:77–83 (1993).

Sugita, M., et al., "Cytoplasmic Tail–Dependent Localization of CD1b Antigen–Presenting Molecules to MIICs," *Science*, 273:349–352 (1996).

Stone, R., "The Price of Broad Patents," *Science*, 268:658 (1995).

Moffat, A.S., "Exploring Transgenic Plants as a New Vaccine Source," *Science*, 268:658–659 (1995).

Chatterjee, D. et al., "Lipoarabinomannan of *Mycobacterium tuberculosis*," (1992) vol. 267, No. 9, pp. 6234–6239.

Gaylord H. et al., "Most *Mycobacterium leprae* Carbohydrate–Reactive Monoclonal Antibodies Are Directed to Lipoarabinomannan," *Infection and Immunity*, (1987), vol. 55, No. 11, pp. 2860–2863.

Beckman, E.M., Porcelli, S.A., Furlong, S. and Brenner, M.B., "A Newly Described Class of Antigens Recognized by αβ T Cells and Presented by CD1 Molecules," Abstract 309, [from *Arthritis & Rheumatism*, vol. 37, No. 9, p. S211 (Suppl. Sep., 1994)].

Sieling, P., Porcelli, S., Chatterjee, D., Brennan, P, Brenner, M., Rea, T., and Modlin, R., "CD1–Restricted αβ TCR T–Cells Recognize Non–Peptide Ligands from Microbial Pathogens," Abstract 90, (from *The Journal of Investigative Dermatology*, vol. 104, No. 4 (Apr., 1995), p. 569.

Beckman, E.M., Porcelli, S.A., Morita, C.T., Behar, S.M., Furlong, S.T., and Brenner, M.B., "Recognition of a Lipid Antigen by CD1–Restricted αβ$^+$ T Cells," *Letters to Nature*, vol. 372, No. 6507, pp. 691–694 (Dec. 15, 1994).

Sieling, P.A., Chatterjee, S.A., Porcelli, T., Prigozy, I., Mazzaccaro, B.J., Soriano, T., Bloom, B.R., Brenner, M.B., Kronenberg, M., Brennan, P.J., and Modlin, R.L., "CD–1 Restricted T. Cell Recognition of Microbial Lipoglycan Antigens," *Science*, vol. 269, No. 5221, pp. 227–230 (Jul. 14, 1995).

Prinzis, S., Chatterjee, D., and Brennan, P.J., "Structure and Antigenicity of Lipoarabinomannan from *Mycobacterium bovis* BCG," *Journal of General Microbiology*, vol. 139, No. 11, pp. 2649–2658 (Nov. 1993).

Anegon, I., et al., "Regulation of HILDA/LIF Gene Expression in Activated Human Monocytic Cells," *J. Immunol.*, 147:3973:3980 (1991).

Balk, S. P., et al., "Oligoclonal Expansion and CD1 Recognition by Human Intestinal Intraepithelial Lymphocytes," *Science*, 253:1411–1415 (1991).

Balk, S. P., et al., "Isolation and Characterization of a cDNA and Gene Coding for a Fourth CD1 Molecule," *Proc. Natl. Acad. Sci. USA*, 86:252–256 (1989).

Bluestone, J. A., "TCRγδ Cells—Minor Redundant T Cell Subset or Specialized Immune System Component," *J. Immunol.*, 142:1785–1788 (1989).

Calabi, F., and Milstein, C., "A Novel Family of Human Major Histocompatibility Complex–Related Genes not Mapping to Chromosome 6," *Nature*, 323:540–543 (1986).

Faure, F., et al., "CD1c as a Target Recognition Structure for Human T Lymphocytes Analysis with Peripheral Blood γδ Cells," *Eur. J. Immunol.*, 20:703–706 (1990).

Glimcher, L. H. and Shevach, E. M., "Production of Autoreactive I Region–Restricted T Cell Hybridomas," *J. Exp. Med.*, 156:640–645 (1982).

Janeway, C. A., Jr., et al., "Specificity and Function of T Cells Bearing γδ Receptors," *Immunol. Today*, 9:73–76 (1988).

Martin, L. H., et al., "Structure and Expression of the Human Thymocyte Antigens CD1a, CD1b and CD1c," *Proc. Natl. Acad. Sci. USA*, 84:9189–9193 (1987).

Morita, C. T., et al., "Functionally Distinct Subsets of Human γδ Cells," *Eur. J. Immunol.*, 21:2999–3007 (1991).

Olive, D., et al., "Two Distinct TL–Like Molecular Subsets Defined by Monoclonal Antibodies on the Surface of Human Thymocytes with Different Expression on Leukemia Lines," *Immunogenetics*, 20:253–264 (1984).

Panchamoorthy, G., et al., "A Predominance of the T Cell Receptor Vγ2/Vδ2 Subset in Human Mycobacteria–Responsive T Cells Suggests Germline Gene Encoded Recognition," *J. Immunol.*, 147:3360–3369 (1991).

Porcelli, S., et al., "Recognition of Cluster of Differentiation 1 Antigens by Human CD4$^-$ CD8$^-$ Cytolytic T Lymphocytes," *Nature*, 341:447–450 (1989).

Porcelli, S., et al., "Biology of the Human γδ T–Cell Receptor," *Immunol. Rev. 120*:137–183 (1991).

Reinherz, E. L., et al., "Discrete Stages of Human Intrathymic Differentiation: Analysis of Normal Thymocytes and Leukemic Lymphoblasts of T–Cell Lineage," *Proc. Natl. Acad. Sci. USA*, 77:1588–1592 (1980).

Strominger, J. L., "The γδ T Cell Receptor and Class 1B MHC–Related Proteins: Enigmatic Molecules of Immune Recognition," *Cell*, 57:895–898 (1989).

Granger, D. L., et al., "Delayed Hypersensitivity and Granulomatous Response after Immunization with Protein Antigens Associated with a Mycobacterial Glycolipid and Oil Droplets," *The Journal of Immunology*, 116(2) :482–488 (1976).

Chaparas, et al., "Tuberculin–Active Carbohydrate that Induces Inhibition of Macrophage Migration but not Lymphocyte Transformation," *Science*, 170:637–639 (1970).

Collins, F. M., "Kinetics of the Delayed–Type Hypersensitivity Response in Tuberculous Guinea Pigs and Mice Tested with Several Mycobacterial Antigen Preparations," *Am. Rev. Respir. Dis. 127*: 599–604 (1983).

Bekierkunst, A., et al., "Immunotherapy of Cancer with Nonliving BCG and Fractions Derived from Mycobacteria: Role of Cord Factor (Trehalose–6,6'–Dimycolate) in Tumor Regression," *Infection and Immunity*, 10:1044–1050 (1974).

Modlin, R. L., et al., "Lymphocytes Bearing Antigen–Specific γδ T–Cell Receptors Accumulate in Human Infectious Disease Lesions," *Nature*, 339:544–548 (1989).

Singh, I. G., et al., "In Vitro Characterization of T Cells from Mycobacterium w–Vaccinated Mice," *Infection and Immunity*, 60(1) :257–263 (1992).

Shivakumar, S., et al., "T Cell Receptor α/β Expressing Double–Negative (CD4$^-$/CD8$^-$) and CD4$^+$ T Helper Cells in Humans Augment the Production of Pathogenic Anti–DNA Autoantibodies Associated with Lupus Nephritis," *J. Immunol.*, 143(1):103–112 (1989).

Rajagopalan, S., et al., "Pathogenic Anti–DNA Autoantibody–Inducing T Helper Cell Lines from Patients with Active Lupus Nephritis: Isolation of CD4$^-$8$^-$T Helper Cell Lines that Express the γδ T–Cell Antigen Receptor," *Proc. Natl. Acad. Sci. USA*, 87:7020–7024 (1990).

Kaufman, S. H. E., "Vaccines Against Tuberculosis: The Impact of Modern Biotechnology," *Scand. J. Infect. Dis. Suppl.* 76:54–59 (1990).

Calabi, F. and Bradbury, A., "The CD1 System," *Tissue Antigens*, 37:1–9 (1991).

Aldovini, A. and Young, R. A., "Humoral and Cell–Mediated Immune Responses to Live Recombinant BCG–HIv Vaccines," *Nature*, 351:479–482 (1991).

Bleicher, P. A., et al., "Expression of Murine CD1 on Gastrointestinal Epithelium," *Science*, 250:679–682 (1990).

Brenner, M. B., et al., "Two Forms of the T–Cell Receptor γ Protein Found on Peripheral Blood Cytotoxic T Lymphocytes," *Nature*, 325:689–694 (1987).

Porcelli, S., et al., "CD1b Restricts the Response of Human CD4$^-$8$^-$ T Lymphocytes to a Microbial Antigen," *Nature*, 360:593–597 (1992).

Daffé, M., et al., "Glycolipids of Recent Clinical Isolates of *Mycobacterium Tuberculosis*: Chemical Characterization and Immunoreactivity," *J. Gen. Microbiol.*, 135:2759–2766 (1989).

Mehta, P. K. and Khuller, G. K., "Protective Immunity to Experimental Tuberculosis by Mannophosphoinositides of Mycobacteria," *Med. Microbiol. Immunol.*, 177:265–284 (1988).

Ribi, S., et al., "Induction of Resistance to Tuberculosis in Mice with Defined Components of Mycobacteria and with some Unrelated Materials," *Immunology*, 46:297–305 (1982).

Janis, E. M., et al., "Activation of γδ T Cells in the Primary Immune Response to *Mycobacterium Tuberculosis*," *Science*, 244:713–244 (1989).

Bekierkunst, B., et al., "Granuloma Formation Induced in Mice by Chemically Defined Mycobacterial Fractions," *J. Bacteriol.* 100(1):95–102 (1969).

Bekierkunst, B., et al., "Cellular Reaction in the Footpad and Draining Lymph Nodes of Mice Induced by Mycobacterial Fractions and BCG Bacilli," *Infection and Immunity*, 4(3):245–255 (1971).

Talwar, G. P., "Immunotherapeutic Effects of a Vaccine Based on a Saprophytic Cultivable Mycobacterium, Mycobacterium w in Multibacillary Leprosy Patients," *Vaccine*, 8:121–129 (1990).

Talwar, G. P., et al., "Immunotherapeutic Trials with a Candidate Anti–Leprosy Vaccine Based on Mycobacterium w," *Trop. Med. Parasitol.*, 41:369–370 (1990).

Okubo, Y., et al., "PPD–Specific Proliferative Response in Humans," *Microbiol. Immunol.*, 26(6):511–521 (1982).

Band, H., et al., "Recognition of Mycobacterial Antigens by γδ T Cells," *Res. Immunol.*, 141:645–651 (1990).

Goerlich, R., et al., "*Plasmodium falciparium* Merozoites Primarily Stimulate the Vγ9 Subset of Human γ/δ T Cells," *Eur. J. Immunol.*, 21:2613–2616 (1991).

Khuller, G. K. and Subrahmanyam, D., "Antigenicity of Phosphatidyl Inositomannosides of *Mycobacterium Tuberculosis*," *Immunochemistry*, 8:251–256 (1971).

Khuller, G. K. and Chopra, A., "Mannophosphoinositides of Actinomycetales," *Actinomycetes*, 17:22–50 (1983).

Lederer, E., "Cord Factor and Related Synthetic Trehalose Diesters," *Springer Semin. Immunopathol.*, 2:133–148 (1979).

Malik, U. and G. K. Khuller, "Effect of Streptomycin on Antibody Response to Mannophosphoinositides in Experimental Tuberculosis," *Indian J. Exp. Biol.*, 21:513–514 (1983).

Reggiardo, Z. and Middlebrook, G., "Serologically Active Glycolipid Families from *Mycobacterium Bovis* BCG," *American J. Epidemiol.*, 100(6):469–476 (1975).

Band, H., et al., "Antigens and Antigen–Presenting Molecules for γδ Cells," *Curr. Top. Microbiol. Immunol.*, 173:229–234 (1991).

Goren, M. B., "Immunoreactive Substances of Mycobacteria," *Amer. Rev. Resp. Dis.*, 125(3):50–69 (1982).

Pfeffer, K., et al., "Primary Responses of Human T Cells to Mycobacteria: A Frequent Set of γδ T Cells are Stimulated by Protease–Resistant Ligands," *Eur. J. Immunol.*, 20:1175–1179 (1990).

Bendelac A., et al., "CD1 Recognition by Mouse NK1[30] T Lymphocytes," *Science* 268:863–865 (1995).

Castaño, A., et al., "Peptide Binding and Presentation by Mouse CD1," *Science* 269:223–226 (1995).

* cited by examiner

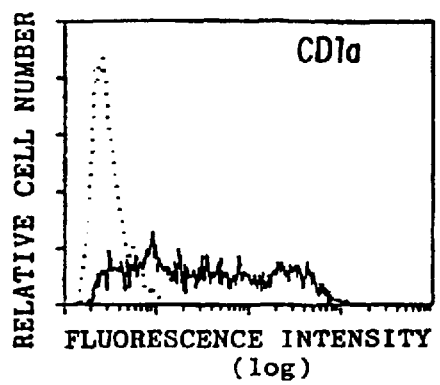
FIG. IA
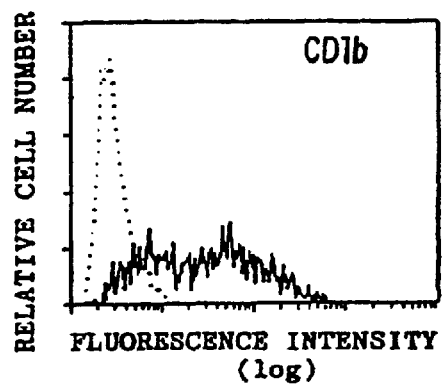
FIG. IB
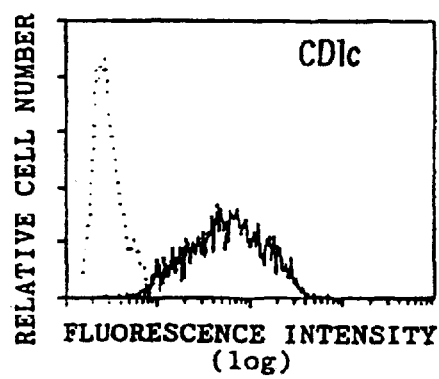
FIG. IC
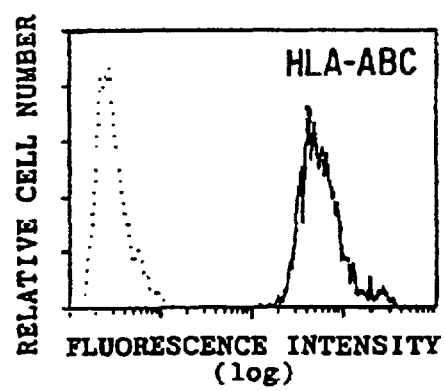
FIG. ID

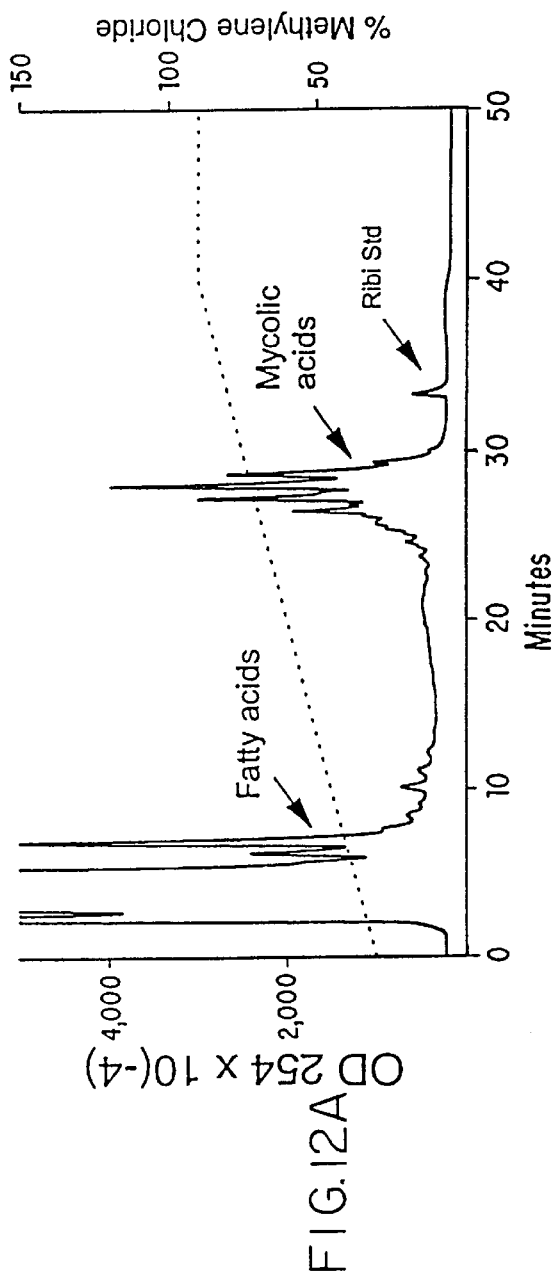
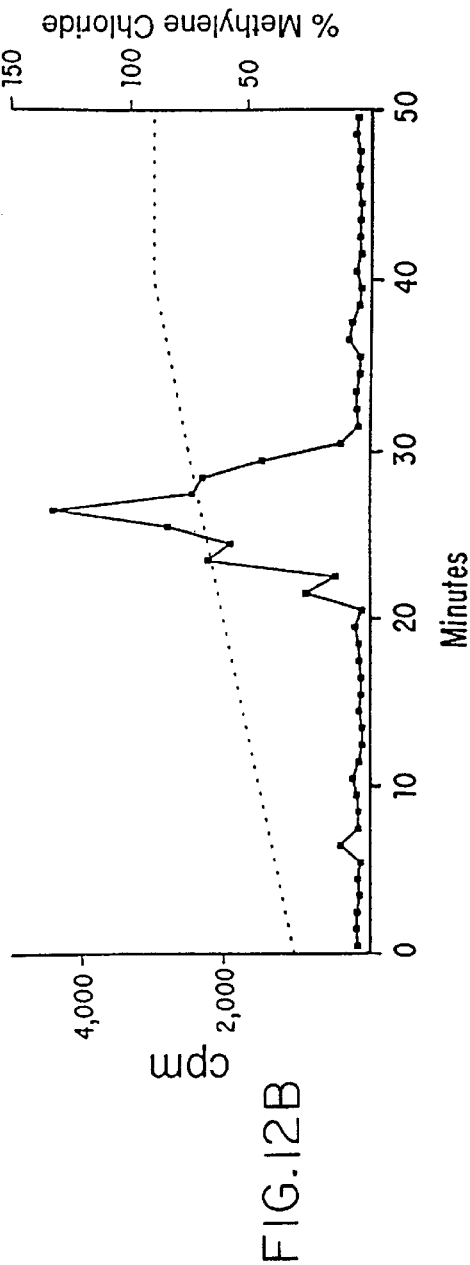
FIG. 12A
FIG. 12B

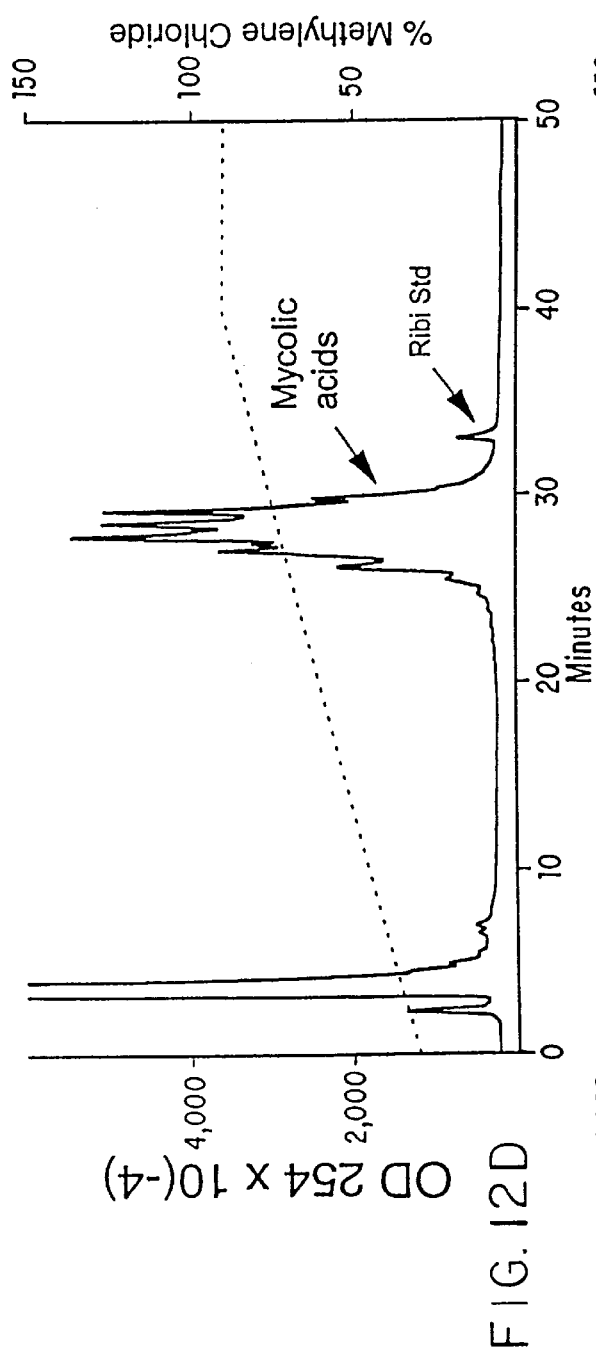
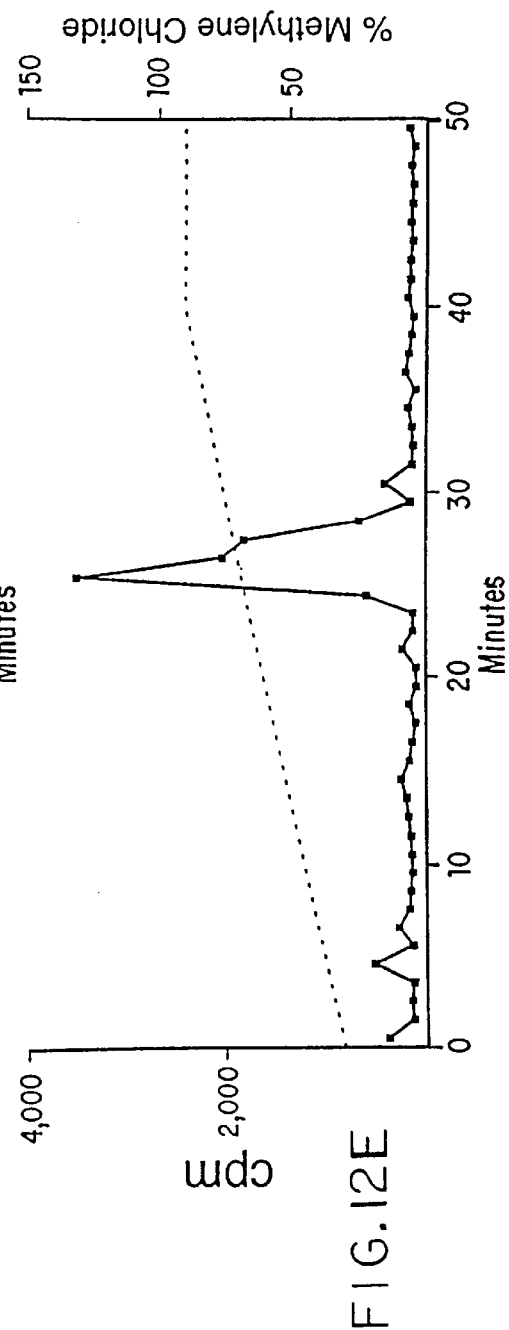
FIG. 12D
FIG. 12E

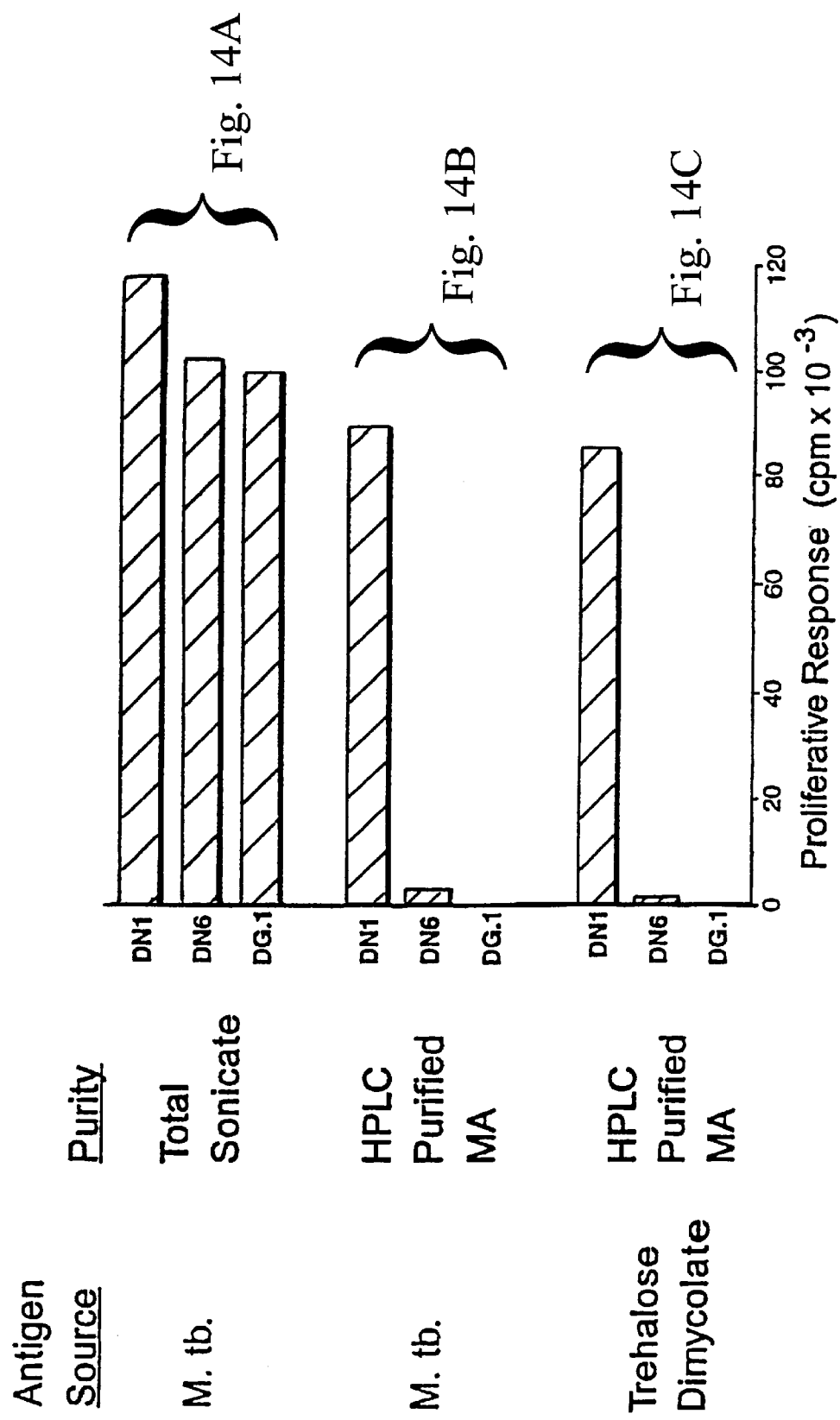

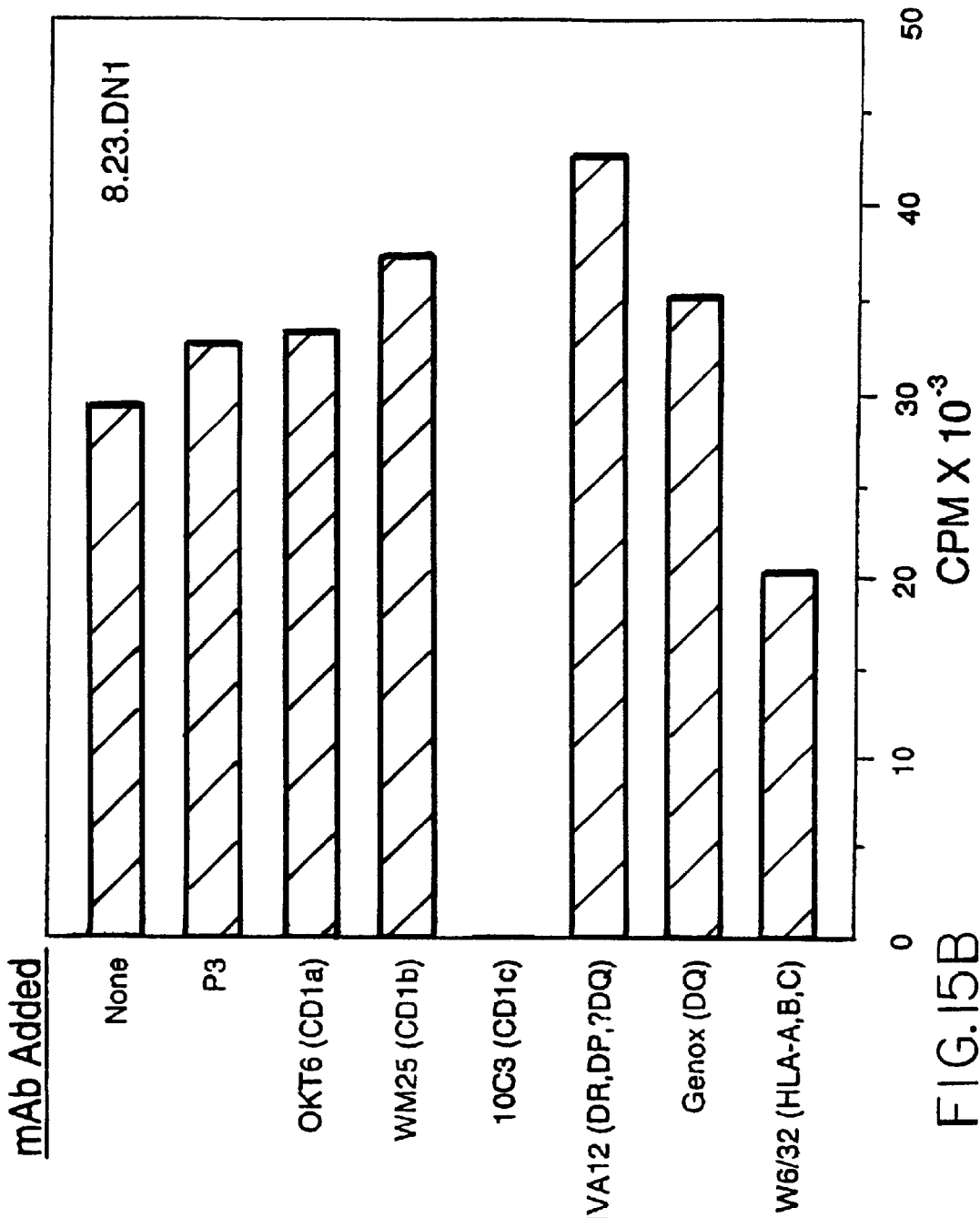

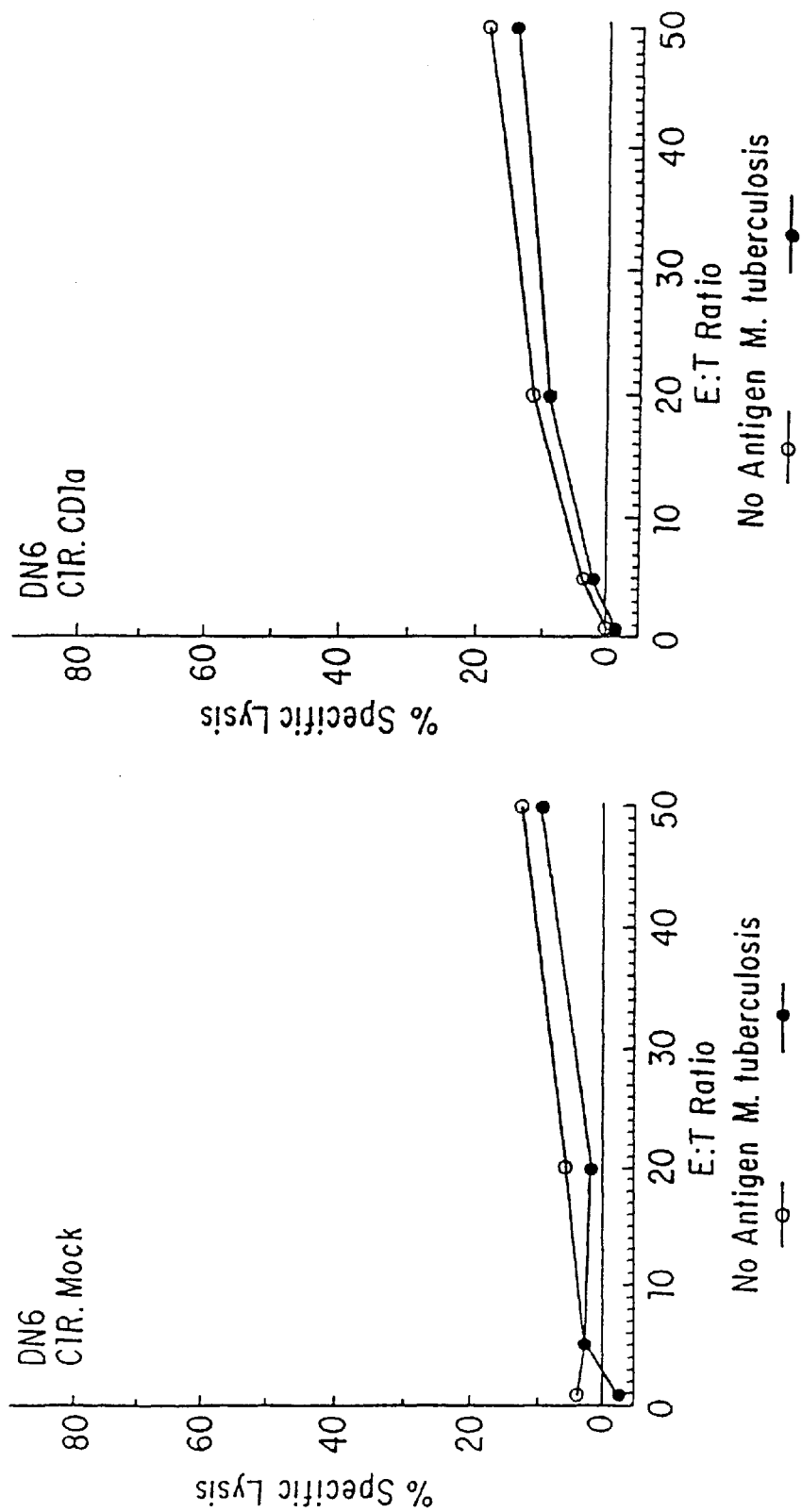

PRESENTATION OF HYDROPHOBIC ANTIGENS TO T-CELLS BY CD1 MOLECULES

RELATED APPLICATIONS

This application is a continuation-in-part of U.S. Ser. No. 08/322,980, filed Oct. 13, 1994 now U.S. Pat. No. 5,679,347, which is a continuing reissue of application Ser. No. 08/322,979, filed Oct. 13, 1994, now U.S. Pat. No. 5,853,737, which is a continuation-in-part application of PCT application PCT/US94/06991, filed Jun. 21, 1994, which is a continuation-in-part application of U.S. Ser. No. 08/080,072, filed Jun. 21, 1993, now abandoned, which is a continuation-in-part application of U.S. Ser. No. 07/989,790, filed Dec. 10, 1992, now abandoned.

STATEMENT OF GOVERNMENT RIGHTS IN THE INVENTION

Part of the work performed during the development of the present invention utilized U.S. Government funds. The U.S. Government has certain rights in the invention.

FIELD OF THE INVENTION

The invention disclosed herein is directed to CD-1 presented antigens, compositions, cells, blocking agents and methods relating to the use of hydrophobic antigen presentation by CD1 molecules, including detection, isolation, vaccine production and administration, blocking of CD1 presentation, blocking agents, induction of CD1 expression and isolated T-cells. CD1-presented antigens of the invention stimulate T-cells to undergo an immune response.

DESCRIPTION OF THE BACKGROUND ART

The Immune System and T-cells

Animals have a complex array of molecular and cellular defenses, collectively referred to as the immune system, that recognize and attack potentially harmful foreign or endogenous but abnormal cells (respectively represented by, e.g., pathogens such as bacteria or viruses, and cancerous or pathogen-infected cells), but tolerate endogenous normal cells. When stimulated by foreign or abnormal biomolecules, the immune system undergoes a series of activities designed to neutralize and destroy the pathogens, or cancerous or pathogen-infected cells, with which the foreign or abnormal biomolecules are associated. These activities, collectively known as an immune response, may consist of a cell-mediated immune response, a humoral (antibody-mediated) immune response, or an immune response that includes elements of cell-mediated and humoral responses.

Humoral immune responses are mediated by antibodies that bind specific foreign or abnormal biomolecules. Antibodies are immunoglobulin (Ig) molecules produced by B-cells, as lymphocytes which originate in avian bursa or in mammalian bone marrow, but migrate to and mature in other organs, particularly the spleen. Robertson, M., *Nature* 301:114 (1983). Cell-mediated immune responses are the result of activities of T-cells, lymphocytes that undergo maturation within the thymus of an animal. Tizard, I. R., *Immunology: An Introduction*, 2d Ed., Saunders, Philadelphia (hereafter "Tizard"), p. 163, 1988. Both T and B-cells migrate between various organs and/or tissues within an animal's body. Lydyard, P., and Grossi, C., Chapter 3 in *Immunology*, 2d Ed., Roitt, I., et al., eds., Gower Medical Publishing, London, New York, 1989.

T-cells mediate at least two general types of immunologic functions, effector and regulatory, reflecting the fact that T-cell activities vary considerably among different subpopulations of T-cells within an animal. Rook, G., Chapter 9 in *Immunology*, 2d Ed., Roitt, I., et al., eds., Gower Medical Publishing, London, New York, 1989. Effector functions include delayed hypersensitivity, allograft rejection, tumor immunity, and graft-versus-host reactivity. Effector functions reflect the ability of some T-cells to secrete proteins called lymphokines, and the ability of other T-cells ("cytotoxic" or "killer" T-cells) to kill other cells. The regulatory functions of T-cells are represented by the ability of "helper" T-cells. Helper T-cells interact with, and produce biomolecules that influence the behavior of, both B-cells and cytotoxic T-cells, in order to promote and direct antibody production and cytotoxic activities, respectively. Mosier, D. E., *Science* 158:1573–1575 (1967). Other classes of T-cells, including suppressor T-cells and memory T-cells, also exist. Miedema, F., and Melief, C. J. M., *Immunol. Today* 6:258–259 (1983); Tizard, pp. 225–228.

Antigen Recognition

In order to function properly, the T- and B-cells of an animal's immune system must accurately and reliably identify the enormous number of molecular compositions derived from foreign ("non-self"), or endogenous ("self") but abnormally expressed, compositions that are encountered. Recognition and identification by the immune system occurs at the molecular level. An antigen, a molecular composition having the potential to generate an immune response, is composed of one or more molecular-sized identifying features known as epitopes. A polypeptide antigen which has an amino acid sequence which comprises, e.g., a hundred amino acids might comprise dozens of epitopes, wherein each epitope is defined by a portion of the polypeptide comprising from about 3 to about 25 amino acids. The number of eptitopes derivable from polypeptides alone is estimated to be about ten million. Tizard, p. 25.

An antigen encountered by a T or B-cell of an animal must be identified as either being associated with normal endogenous (i.e., self) antigens, an immune response to which would be injurious to the animal, or with foreign or abnormal (i.e., non-self) antigens, to which an immune response should be mounted. As part of the immune system's means of identifying antigens, individual T and B-cells produce antigen receptors which are displayed on the T or B-cell's surface and which bind specific antigens. Turner, M., Chapter 5 in *Immunology*, 2d Ed., Roitt, I., et al., eds., Gower Medical Publishing, London, New York, 1989. B-cells produce and display antigen receptors that comprise Ig molecules which have unique antigen-binding portions due to unique amino acid sequences in the variable regions of each of the two antibody subunits, known as the Ig heavy and Ig light chains. Each B-cell membrane comprises from 20,000 to 200,000 identical Ig molecules. Tizard, pp. 78–80 and 202.

The T-cell antigen receptors (TCRs) produced by and displayed on individual T-cells comprise heavy (TCRβ) and light (TCRα) chains (polypeptide subunits) which are linked by a disulfide bond on the T-cell surface. Each TCRα and β subunit has a carboxy-terminal constant region, the amino acid sequence of which does not vary from T-cell to T-cell, and an amino-terminal variable region, the amino acid sequence of which does vary from T-cell to T-cell. When TCRα and TCRβ subunits associate with each other, the variable regions of the TCRα and TCRβ polypeptide subunits combine to form the unique antigen-binding portion of an α:β TCR. A second type of TCR heterodimer, γ:δ, has been described but its function, if any, is unknown. Davis, M. M., and Bjorkman, P. J., *Nature* 334:395–404 (1988).

Although at least one mixed TCR heterodimer of unknown function, β:δ TCR, has been described, T-cells bearing α:β TCR molecules are numerically dominant in mature animals. Hochstenbach, F., and Brenner, M. B., *Nature* 340:562–565 (1989).

Although each individual T- or B-cell displays identical antigen receptors, the receptor displayed varies from cell to cell; an animal's collection of different antigen receptors is thus quite diverse. The genetic basis of this diversity is as follows. The variable region of an Ig heavy chain, or that of a TCRβ chain, is encoded by three gene segments, the variable (V), diversity (D) and joining (J) segments. The variable region of an Ig light chain, or that of a TCRα chain, is encoded by V and J gene segments. Multiple DNA sequences encoding many different V, D and J gene segments are present as unexpressed copies in germline DNA; an analogous but different collection of variable gene segments for TCR subunits is also present. During development of an animal, genes encoding diverse variable regions are generated in individual cells of the immune system by the random joining of V, D and J, or V and J, gene segments. The process of DNA rearrangements that generates a randomly assembled variable region of an Ig heavy or TCRβ subunit is called V-D-J joining; the analogous process that generates a rearranged variable region of an Ig light or TCRα subunit is called V-J joining. Sakano, H., et al., *Nature* 280:288–294 (1979); Early, P., et al., *Cell* 19:981–992 (1980); Alt, F. W., et al., *Science* 238:1079–1087 (1987); Harlow, E., and Lane, D., *Antibodies: A Laboratory Manual*, Cold Spring Harbor Laboratory Press, Cold Spring Harbor, pages 10–18, 1988; Davis, M. M., and Bjorkman, P. J., *Nature* 334:395–404 (1988).

A functionally rearranged Ig or TCR subunit gene is one in which the DNA rearrangements of V-D-J or V-J joining have not resulted in a reading frame that is prematurely terminated because of the introduction of stop codons or frameshifting mutations. Because each T or B-cell of the immune system expresses genes encoding their respective antigen receptors in which a unique functionally rearranged variable region is present, many different T or B-cells, each producing a receptor that has a unique antigen-recognizing region, are generated. Hay, F., Chapter 6 in *Immunology*, 2d Ed., Roitt, I., et al., eds., Gower Medical Publishing, London, New York, 1989. The total catalog of different antigen receptors displayed on the T-cells of an animal is referred to as the animal's TCR repertoire. Bevan, M. J., et al., *Science* 264:796–797 (1994).

For mature T- or B-cells, binding of antigen to a cell's antigen receptor activates the cell, i.e., stimulates the cell to undertake activities related to generating a cell-mediated or humoral immune response. Typically, activated mature T or B-cells proliferate in response to antigen. In contrast, for immature T or B-cells, binding of antigen to a displayed TCR or B-cell antigen receptor, respectively, results in elimination of the cell by a process called negative selection or clonal deletion. Clonal deletion occurs during normal development of a healthy wildtype animal, and is a mechanism by which the immune system learns to tolerate the animal's normal endogenous (self) antigens, i.e., to treat the animal's self antigens as non-immunogenic antigens. Failure of the immune system to achieve or maintain tolerance of self antigens may result in autoimmune responses (i.e., autoimmune response to self antigens) that can culminate in autoimmune disease in animals including humans. Autoimmune disease can occur when an appropriate immune response to a non-self antigen results in the production of immune effector biomolecules (e.g., autoantibodies) or cells that cross-react with self antigens. Human autoimmune diseases include such crippling conditions as Multiple Sclerosis (MS) and Systemic Lupus Erythematosus (SLE). Roitt, I., Chapter 23 in *Immunology*, 2d Ed., Roitt, I., et al., eds., Gower Medical Publishing, London, New York, 1989; Steinman, L., *Sci. American* 269:107–114 (1993).

Antigen Presentation

Although the antigen receptors of B-cells can directly bind soluble antigen, T-cells typically respond to antigen only when it is displayed on specific classes of other cells known generically as an antigen-presenting cells (APCs). Feldmann, M., and Male, D., Chapter 8 in *Immunology*, 2d Ed., Roitt, I., et al., eds., Gower Medical Publishing, London, New York, 1989. APCs, e.g., macrophages and dendritic cells, present antigens derived from polypeptides via glycoproteins, known as MHC (major histocompatibility complex) proteins, which are displayed on the surface of APCs. Bevan, M. J., et al., *Science* 264:796–797 (1994). The nomenclature for MHC gene products varies from species to species. For example, human MHC proteins are also referred to as human lymphocyte antigens (HLA), murine MHC proteins are also referred to as H-2 antigens, and rat MHC proteins are also called RT1 antigens. Tizard, p. 181. Particular MHC proteins bind selected classes of antigens with limited specificity. For the most part, the specificity determinants in a TCR:Ag:MHC complex are (1) the unique polypeptide sequences of the variable portion of the TCR and (2) the unique polypeptide sequences of antigen. However, to some degree, MHC-presented oligopeptide antigens are embedded within an MHC molecule and TCR recognition of antigen only occurs within the context of an appropriate class of MHC molecule. Janeway, C. A., *Sci. American* 269:73–79 (1993). This phenomenon, called MHC restriction, is of fundamental importance to T-cell antigen recognition and physiology. Zinkernagel, R. M., and Doherty, P. C., *Nature* 248:701–702 (1974).

In MHC-mediated presentation of antigens, the α:β T-cell antigen receptor recognizes peptide antigens in conjunction with products of MHC genes. In the case of soluble antigens, recognition occurs in conjunction with Class II molecules. For viral antigens, recognition is in conjunction with Class I molecules. Furthermore, large soluble antigens are processed from polypeptides by an appropriate accessory cell, such as a macrophage or dendritic cell.

The general sequence of events involved in T-cell recognition of polypeptide antigens in MHC restriction is as follows. A polypeptide antigen is phagocytosed by an antigen-presenting cell, internalized, processed, and then a peptide derived from the polypeptide is displayed on the cell surface in conjunction with Class I or Class II MHC molecules. In order to present antigen, MHC Class I molecules require an additional protein, $\beta_2$-microglobulin. Tizard, pp. 181–183. A T-cell antigen receptor α:β heterodimer then recognizes the peptide antigen plus the MHC gene product. Recognition of peptide antigen alone or MHC gene product alone is not sufficient to signal T-cell activation. Only the MHC:Ag complex can be appropriately recognized by a TCR molecule. Steward, M., Chapter 7 in *Immunology*, 2d Ed., Roitt, I., et al., eds., Gower Medical Publishing, London, New York, 1989.

The genes encoding MHC proteins are diverse; however, unlike Ig and TCR molecules, which vary from cell to cell in an individual animal, MHC antigens vary from individual animal to individual animal or from one group of related individual animals to another group. Members of familial groups, represented in the mouse by inbred strains of mice, share similar MHC antigens with each other, but not with individuals from other strains of mice. Snell, G. D., *Science* 213:172–178 (1981); Owen, M., Chapter 4 in *Immunology*, 2d Ed., Roitt, I., et al., eds., Gower Medical Publishing, London, New York, 1989. Because variant MHC molecules will be capable of binding different antigens, the antigens that T-cells will be able to recognize (i.e., specifically bind in the MHC context) and respond to varies among different strains of mice. Cooke, A., Chapter 11 in *Immunology*, 2d Ed., Roitt, I., et al., eds., Gower Medical Publishing, London, New York, 1989. In humans, particular genetic alleles encoding MHC (HLA) molecules are more highly associated with autoimmune diseases, presumably because these MHC molecules are more competent at binding (and thus presenting to T-cells) self antigens. Vaughan, in *Immunological Diseases*, 3rd Ed., Vol. II, Samter, M., ed., pp. 1029–1037 (1978); Steinman, L., *Sci. American* 269:107–114 (1993).

T-cell Subsets

Classes of T-cells are to some extent distinguished on the basis that different T-cells display different CD proteins on their surfaces. Immature T-cells display both CD4 and CD8 proteins (i.e., immature T-cells are CD4$^+$8$^+$), mature helper T-cells are CD4$^+$8$^-$ (i.e., display CD4 protein but not CD8 protein) and mature cytotoxic T-cells are CD4$^-$8$^+$ (i.e., display CD8 protein but not CD4 protein). Smith, L., *Nature* 326:798–800 (1987); Weissman, I. L., and Cooper, M. D., *Sci. American* 269:65–71 (1993).

In most cases so far examined, CD8$^+$ T lymphocytes recognize MHC class I complexes, while CD4$^+$ cells recognize MHC class II complexes on antigen presenting cells. The involvement of CD8 and CD4 in antigen recognition by $\alpha:\beta$ TCRs is significant. CD4 and CD8 molecules increase the avidity of the TCR interaction Ag:MHC complexes and are sometimes referred to as co-receptors (Bierer, B. E., et al., *Ann. Rev. Immunol.* 7:579–599 (1989); Steward, M., Chapter 7 in *Immunology*, 2d Ed., Roitt, I., et al., eds., Gower Medical Publishing, London, New York, 1989). Because of the importance of CD4 and CD8 in antigen recognition in the MHC context, CD4$^-$8$^-$ (double negative; DN) T-cells have classically been considered to be immature thymic T-cell precursors. Lydyard, L., and Grossi, C., Chapters 2 and 14 in *Immunology*, 2d Ed., Roitt, I., et al., eds., Gower Medical Publishing, London, New York, 1989; Smith, L., *Nature* 326:798–800 (1987); Strominger, J. L., et al., *Int. J. Cancer Suppl.* 4:43–47 (1989); Shirai, T., et al., *J. Immunology* 144:3756–3761 (1990); Weissman, I. L. and Cooper, M. D., *Sci. American* 269:65–71 (1993).

The DN subpopulation of T-cells is distinctive in regard to the TCRs that they display. The majority of human DN T-cells isolated from peripheral blood express $\delta:\gamma$ TCRs. Porcelli, S., et al., *Immunological Reviews* 120:137–183 (1991). A large proportion (approximately 60%) of murine DN $\alpha:\beta$ TCR T-cells express V$\beta$8 gene products (Fowlkes, B. J., et al., *Nature* 329:251–254 (1987); Bix, M., et al., *J. Exp. Med.* 178:901–908 (1993)). Several analyses in mice point to a striking lack of junctional (V-J or V-D-J) diversity and restricted use of germline V and J gene elements, especially for TCR$\alpha$ subunits. Koseki, H., et al., *Proc. Natl. Acad. Sci. USA* 87:5248–5252 (1990); Kubota, H., et al., *J. Immunol.* 149:1143–1150 (1992). Examination of fresh DN $\alpha:\beta$ TCR T-cells in humans revealed a striking predominance of an invariant (canonical) V$\alpha$24-J$\alpha$Q rearrangement that lacked N region additions. Porcelli, S., et al., *J. Exp. Med.* 178:1–16 (1993). Taken together, these observations suggest that DN $\alpha:\beta$ TCR T-cells may represent a developmentally distinct subpopulation of T lymphocytes whose limited receptor repertoire reflects recognition of a restricted set of antigens and/or antigen-presenting molecules.

CD1 Proteins

Polypeptide molecules encoded by the genes of the CD1 locus are recognized by select CD4$^-$8$^-$ T-cell clones expressing either $\alpha:\beta$ or $\gamma:\delta$ TCRs (Porcelli, S., et al., *Nature* 341:447–450 (1989); Faure, F., et al., *Eur. J. Immun.* 20:703–706 (1990)). Because of the structural resemblance of CD1 molecules, encoded by genes on human chromosome 1, to MHC molecules, encoded by genes on human chromosome 6 (Calabi, F. and Milstein, C., *Nature* 323:540–543 (1986); Balk, S. P., et al., *Proc. Natl. Acad. Sci. USA* 86:252–256 (1989)), it has been suggested that CD1 may represent a family of antigen presenting molecules separate from those encoded by the MHC genes. Porcelli, S., et al., *Nature* 341:447–450 (1989); Strominger, J. L., *Cell* 57:895–898 (1989); Porcelli, S., et al., *Immun. Rev.* 120:137–183 (1991).

The five CD1 genes reveal exon and domain structure ($\alpha 1$, $\alpha 2$, $\alpha 3$) that is similar to that of MHC class I genes, yet the proteins are only distantly related in sequence. All CD1 family members share a conserved $\alpha 3$ domain; however, even this domain shows only 32% homology in amino acid sequence with consensus residues of class I MHC $\alpha 3$ domains and there is no detectable homology with $\alpha 1$ domains. A major difference between MHC and CD1 molecules is polymorphism. Human MHC genes are extremely polymorphic: multiple alleles have been described at each known MHC locus. In contrast, CD1 genes are apparently nonpolymorphic. Despite these differences, the CD1 proteins, like MHC Class I molecules, are expressed as large subunits (heavy chains) non-covalently associated with $\beta_2$-microglobulin. Van Agthoven, A., and Terhorst, C., *J. Immunol.* 128:426–432 (1982); Terhorst, C., et al., *Cell* 23:771–780 (1981)).

Five CD1 genes have thus far been identified in humans: CD1a, CD1b, CD1c, CD1d and CD1e. Four of the five CD1 gene products have been defined serologically, are referred to as CD1a, CD1b, CD1c and CD1d and are distinguished by unique heavy chains with approximate molecular weights of 49kDa, 45kDa, 43kDa and 48kDa respectively (Amiot, M., et al., *J. Immunol.* 136:1752–1758 (1986); Porcelli, S., et al., *Immunol. Rev.* 120:137–183 (1991); Bleicher, P. A., et al., *Science* 250:679–682 (1990)). CD1 proteins are displayed on a number of APCs including Langerhans cells (which are the major dendritic antigen–presenting cells in the skin), activated B-cells, dendritic cells in lymph nodes, and on activated blood monocytes (Porcelli, S., et al., *Nature* 360:593–597 (1992); *Leukocyte Typing IV*, Knapp, W., ed., Oxford University Press, Oxford, U.K., pp. 251–269, 1989; *Tissue Antigens*, Kissmeyer-Nielsen, F., ed., Munksgard, Copenhagen, Denmark, pp. 65–72, 1989.

Previous work has shown that CD1 proteins are recognized by CD4$^-$8$^-$ T-cell lines derived from patients with SLE. Porcelli, et al., *Nature* 341:447–450 (1989). Leukemia cells expressing CD1 proteins were lysed by the T-cells independent of MHC restriction, even though no foreign (non-self) antigen was present. DN T-cells lysed leukemic cells in a CD1-dependent manner in the absence of antigen. Thus, the possibility exists that CD1 proteins play a role in autoimmune diseases.

The central dogma of immunology has been that the immune system does not normally react to self. Autoimmunity defines a state in which the natural unresponsiveness or tolerance to self terminates. As a result, antibodies or cells react with self constituents, thereby causing disease. There is as yet no established unifying concept to explain the origin and pathogenesis of the various autoimmune disorders. The disease process may be caused, among other things, by sensitized T lymphocytes. These lymphocytes produce tissue lesions by poorly understood mechanisms which may involve the release of destructive lymphokines or which attract other inflammatory cells to the lesion. For a review of autoimmunity, see Theofilopoulos, A. N., Chapter 11 in *Basic and Clinical Immunology,* 6th Ed., Stites, D. P., et al., eds., Appleton and Lang, 1987.
Tuberculosis Mycobacteria are a genus of aerobic intracellular bacterial organisms which upon invasion of their host, survive within endosomal compartments of monocytes and macrophages. Human mycobacterial diseases include tuberculosis (caused by *M. tuberculosis*), leprosy (caused by *M. leprae*), Bairnsdale ulcers (caused by *M. ulcerans*), and various infections caused by *M. marinum, M. kansasii, M. scrofulaceum, M. szulgai, M. xenopi, M. fortuitum, M. chelonei, M. haemophilum* and *M. intracellulare.* Wolinsky, E., Chapter 37 in *Microbiology: Including Immunology and Molecular Genetics,* 3rd Ed., Harper & Row, Philadelphia, 1980, hereafter "Wolinksy"; Daniel, T. M., Miller, R. A. and Freedman, S. D., Chapters 119, 120 and 121, respectively, in *Harrison's Principles of Internal Medicine,* 11th Ed., Braunwald, E., et al., eds., McGraw-Hill, New York, 1987.

One third of the world's population harbors *M. tuberculosis* (M. tb.) and is at risk for developing tuberculosis (TB), which is specifically responsible for 18.5% of deaths in adults aged 15 to 59. Bloom, B. R., and Murray, C. J. L., *Science* 257:1055–1064 (1992). Because improved public health and antibiotic therapy have greatly reduced the occurrence and/or severity of TB in the United States, these alarming statistics derive largely from third-world countries. Unfortunately, with the advent of AIDS, tuberculosis is increasing at a nearly logarithmic rate, and multidrug resistant strains are appearing and now account for one third of all cases in New York City. Bloom, B. R., and Murray, C. J. L., *Science* 257:1055–1064 (1992); U.S. Congress, Office of Technology Assessment, *The Continuing Challenge of Tuberculosis,* OTA-H-574, U.S. Government Printing Office, Washington, D.C., 1993. Mycobacterial strains which were previously considered to be nonpathogenic strains (e.g., *M. avium*) have now become major killers of immunosuppressed AIDS patients. Moreover, current Mycobacterial vaccines are either inadequate, in the case of the BCG vaccine to M. tb., or, with regard to *M. leprae*, unavailable. Kaufmann, S., *Microbiol. Sci.* 4:324–328 (1987); U.S. Congress, Office of Technology Assessment, *The Continuing Challenge of Tuberculosis,* pp. 62–67, OTA-H-574, U.S. Government Printing Office, Washington, D.C., 1993.

The major response to mycobacteria involves cell mediated delayed hypersensitivity (DTH) reactions with T-cells and macrophages playing major roles in the intracellular killing and containing or walling off (granuloma formation) of the organism. A major T-cell response involves CD4$^+$ lymphocytes that recognize mycobacterial heat shock proteins (such as hsp65) as immunodominant antigens. Kaufmann, S. H., et al., *Eur. J. Immunol.* 17:351–357 (1987).
Leprosy Leprosy (Hansen's disease) is a chronic granulomatous infection of humans which attacks superficial tissues, especially the skin and peripheral nerves. Accounts of leprosy extend back to the earliest historical records and document a stigmatization of leprosy patients which transcends cultural and religious boundaries. Miller, R. A., Chapter 120 in *Harrison's Principles of Internal Medicine,* 11th Ed., Braunwald, E., et al., eds., McGraw-Hill, New York, 1987, hereafter "Miller." In ancient times leprosy was rampant throughout most of the world, but for unknown reasons it died out in Europe in the sixteenth century and now occurs there only in a few isolated pockets. Wolinsky, p. 741.

There are probably 10 to 20 million persons affected with leprosy in the world. The disease is more common in tropical countries, in many of which the prevalent rate is 1 to 2 percent of the population. A warm environment is not critical for transmission, as leprosy also occurs in certain regions with cooler climates, such as Korea and central Mexico. Distribution of infected individuals within countries is very nonhomogeneous, and districts in which 20 percent of the population is affected can be found. Miller, p. 633.

In the United States, leprosy occurs particularly in Texas, California, Louisiana, Florida, New York City, and Hawaii, usually in persons originally from Puerto Rico, the Philippines, Mexico, Cuba, or Samoa. Indigenous transmission occurs primarily in Hawaii, the Pacific Island territories, and specifically along the Gulf coast. Several hundred patients are cared for at the national leprosarium in Carville, La. Wolinsky, p. 741.

*Mycobacterium leprae,* or Hansen's bacillus, is the causal agent of leprosy. It is an acid-fast rod assigned to the family Mycobacteriaceae on the basis of morphologic, biochemical, antigenic, and genetic similarities to other mycobacteria. *M. leprae* causes chronic granulomatous lesions closely resembling those of tuberculosis, with epithelioid and giant-cells, but without caseation. The organisms in the lesions are predominantly intercellular and can evidently proliferate within macrophages, like tubercle bacilli. Wolinsky, p. 740.

Although *M. leprae* has not been cultivated in artificial media or tissue culture, it can be consistently propagated in the foot pads of mice. Systemic infections with manifestations similar to those of human disease can be induced in armadillos and mangabey monkeys. The bacillus multiplies exceedingly slowly, with an estimated optimal doubling time of 11 to 13 days during logarithmic growth in mouse foot pads. The mouse model has been used extensively for the study of antileprosy drugs, and the high bacterial yield from armadillos has been crucial for immunogenic studies. Miller, p. 633.

Leprosy is apparently transmitted when exudates of mucous membrane lesions and skin ulcers reach skin abrasions; it is not highly contagious and patients need not be isolated. Young children appear to acquire the disease on briefer contact than adults. The incubation period is estimated to range from a few months to 30 years or more. Apparently, *M. leprae* can lie dormant in tissues for prolonged periods. Wolinsky, p. 741. Leprosy can present at any age, although cases in infants less than one year of age are extremely rare. The age-specific incidence peaks during childhood in most developing countries, with up to 20% of cases occurring in children under 10. Since leprosy is most prevalent in poorer socioeconomic groups, this may simply reflect the age distribution of the high-risk population. The sex ratio of leprosy presenting during childhood is essentially 1:1, but males predominate by a 2:1 ratio in adult cases. Miller, p. 633.

Leprosy is distinguished by its chronic, slow progress and by its mutilating and disfiguring lesions. These may be so distinctive that the diagnosis is apparent at a glance; or the clinical manifestations may be so subtle as to escape detection by any except the most experienced observers armed with a high index of suspicion. The organism has a predilection for skin and for nerve. In the cutaneous form of the disease, large, firm nodules (lepromas) are distributed widely, and on the face they create a characteristic leonine appearance. In the normal form, segments of peripheral nerves are involved, more or less at random, leading to localized patches of anesthesia. The loss of sensation in fingers and toes increases the frequency of minor trauma, leading to secondary infections and mutilating injuries. Both forms may be present in the same patient.

In either form of leprosy, three phases may be distinguished. (1) In the lepromatous or progressive type, the lesions contain many lepra cells: macrophages with a characteristically foamy cytoplasm, in which acid-fast bacilli are abundant. When these lesions are prominent, the lepromin test is usually negative, presumably owing to desensitization by massive amounts of endogenous lepromin, and the cell-mediated immune reactions to specific and nonspecific stimuli are markedly diminished. The disease is then in a progressive phase and the prognosis is poor. (2) In the tuberculoid or healing phase of the disease, in contrast, the lesions contain few lepra cells and bacilli, fibrosis is prominent, and the lepromin test is usually positive. (3) In the intermediate type of disease, bacilli are seen in areas of necrosis but are rare elsewhere, the skin test is positive, and the long-range outlook is fair. Shifts from one phase to another, with exacerbation and remission of the disease, are common.

Hansen's bacillus may be widely distributed in the tissues of persons with leprosy, including the liver and spleen. Nevertheless, no destructive lesions or disturbance of function are observed in these organs. Most deaths in leprous patients are due not to leprosy per se but to intercurrent infections with other microorganisms—often tuberculosis. Leprosy itself often causes death through the complication of amyloidosis, which is characterized by massive waxy deposits, containing abundant precipitates of fragments of immunoglobulin light chain in kidneys, liver, spleen, and other organs. Wolinsky, pp. 740–741.

Bacteriologic diagnosis of leprosy is accomplished by demonstrating acid-fast bacilli in scrapings from ulcerated lesions, or in fluid expressed from superficial incisions over non-ulcerated lesions. No useful serologic test is available, but patients with leprosy frequently have a false-positive serologic test for syphilis. Also useful in the tuberculoid phase is the skin test with lepromin, an antigenic bacillary material prepared by boiling human lepromatous tissue or infected armidillo tissues, which is typically standardized to contain $160 \times 10^6$ acid-fast bacilli/ml. Wolinsky, pp. 740–741.

Therapy with dapsone (4,4'-diaminodiphenylsulfone) or related compounds usually produces a gradual improvement over several years, and is continued for a prolonged period after apparent clinical remission. However, resistance to sulfonic drugs, with a concomittant relapse, may be noted after years of apparently successful treatment. Rifampin and clofazimine (B663, a phenozine derivative) are promising agents now under investigation for treating leprosy. Treatment results may be evaluated by counting the acid-fast bacilli in serial biopses and skin scrapings. Wolinsky, p. 741.

Because of the neurodegenerative nature of leprosy, and associated symptoms, the management of leprosy involves a broad, multidisciplinary approach, including consulatative services such as orthopedic surgery, opthamology, and physical therapy in addition to antimicrobial chemotherapy. In any event, however, recovery from neurologic impairment is limited. Miller, pp. 635–636.

SUMMARY OF THE INVENTION

The present invention is based on the novel and unexpected observation that CD1 molecules function to present foreign antigens as well as autoimmune antigens to T-cells. The invention is further based on the observation that isolated blood monocytes can be induced to express CD1, and therefore become competent to present antigens to T-cells, by contacting the monocytes with cytokines. Based on these two observations, the present invention discloses methods of isolating $CD1^+$ antigen-presenting cells ($CD1^+$ APCs) which are used to identify, isolate, and purify CD1-presented hydrophobic antigens, various methods for determining whether a sample contains one or more CD1-presented antigens, methods for isolating and purifying CD1-presented antigens, purified CD1-presented antigens isolated by the methods disclosed herein, and methods of providing and using isolated CD1-presented antigens in vaccines.

In one embodiment, the present invention provides methods for determining whether a sample contains a CD1-presented hydrophobic antigen. In one such method, the presence of a CD1-presented antigen in the sample can be determined by (1) contacting the sample with cells which have been induced to express a CD1 protein, (2) contacting the cells from the first step with T-cells that specifically recognize a CD1-presented antigen, and (3) measuring the proliferative or cytolytic response of the T-cells, wherein increased T-cell proliferation or T-cell-mediated cytolysis of $CD1^+$ target-cells, respectively, correlates with the presence of a CD1-presented antigen. In a related embodiment, the present invention provides for methods of determining whether a sample contains a CD1 blocking agent, i.e., a composition that inhibits CD1-restricted antigen presentation. In the related embodiment, the assay for CD1-presented antigen described above is performed in duplicate, with a first (control) assay being performed as above, and a second assay additionally containing a sample suspected of containing a CD1 blocking agent. The presence of CD1 blocking agents in the sample correlates with a T-cell proliferative or cytolytic response in the second assay that is less than that measured in the first assay.

The present invention further provides methods for inducing CD1 expression in cells, such as monocytes, in order to generate $CD1^+$ antigen-presenting cells (APCs). In one method, CD1 expression is induced in isolated blood monocytes by contacting the cells with one or more cytokines. The preferred cytokines for CD1 induction are granulocyte/macrophage colony stimulating factor (GM-CSF), GM-CSF in combination with interleukin-4 (IL-4), or interleukin-3 (IL-3). $CD1^+$ APCs are cells that express and display CD1 proteins and are thus competent to present CD-restricted antigens to $TCR^+$ T-cells. $CD1^+$ APCs are used in several of the methods disclosed herein.

The present invention further provides methods for isolating a CD1-presented antigen from a sample. In one such method, a sample containing a CD1-presented antigen is first fractionated using conventional techniques. The resulting fractions are then tested using known procedures, or those disclosed herein, for the presence of a CD1-presented antigen. The fractions containing the CD1-presented antigen are then either used in the development of vaccines or are further fractionated to obtain higher levels of purity of the CD1-presented antigen.

The present invention further provides alternative methods for isolating CD1-presented antigens from a sample which rely on the ability of a CD1-presented antigen to bind either isolated CD1 or CD1 expressed on a cell surface. In one such method, a sample containing a CD1-presented antigen is incubated with either $CD1^+$ APCs or purified CD1 molecules. The resulting complexes of antigen:$CD1^+$ APC or antigen: CD1 molecule are then removed from the sample and subjected to conditions in which the CD1 molecule releases the bound CD1-presented antigen. The released CD1-presented antigen is then purified away from either the CD1+ APC or the purified CD1 molecule and may be further characterized using conventional immunological, biochemical and/or genetic methods. Purified CD1-presented antigens, or synthetic or genetically engineered derivatives thereof, are then tested for CD1-presented antigen activity using known procedures, or those disclosed herein, and may be used in the formulation of vaccines.

Utilizing the above procedures for isolating a CD1-presented antigen, the present invention further provides isolated CD1-presented antigens which have been prepared by the methods disclosed herein. The isolated CD1-presented antigens prepared by the disclosed methods can be used either in the characterization of the nature of CD1-presented antigens, in the development or formulation of vaccines, or in the development of autoimmune therapies.

The present invention is further based on the observation that CD1-mediated antigen presentation can serve as a basis for the development of autoimmune disease. Based on this observation, the present invention provides methods of and means for inhibiting CD1-mediated antigen presentation by a CD1+ APC. CD1-mediated antigen presentation can be inhibited by various compositions that are described herein or are isolated by the methods of the invention.

BRIEF DESCRIPTION OF THE FIGURES

FIGS. 1A–H show data for the expression of CD1a, CD1b and CD1c by monocytes cultured with GM-CSF and IL-4, and surface phenotype of CD1b-restricted T-cells specific for *Mycobacterium tuberculosis*. Flow cytometric analysis of peripheral blood monocytes cultured for 60 hours in medium containing GM-CSF and IL-4 showing expression of CD1a (FIG. 1A), CD1b (FIG. 1B), CD1c (FIG. 1C), and HLA (FIG. 1D). Cells were stained with control monoclonal antibody (mAb) (dotted line) or mAbs with the specificity indicated in each histogram box (solid lines). Monocytes cultured in the absence of cytokines or with interferon-γ did not express significant levels of CD1a, CD1b or CD1c (data not shown). Flow cytometric analysis of T-cell line DN1 showing its expression of α:β TCRs (FIG. 1E), non-expression of CD4 (FIG. 1F), and minimal or non-expression of CD8 (FIGS. 1G, 1H). Dotted and solid lines represent control and specific mAbs as in FIGS. 1a–1d.

FIG. 2A shows data for the proliferative responses (counts per minute (CPM)) of ³H-thymidine incorporated) of DN1 to *M. tuberculosis* (solid squares), *M. leprae* (solid circles), *Escherichia coli* (open circles) and tetanus toxoid (open squares). Antigen presenting cells were heterologous GM-CSF- and IL-4-treated CD1+ monocytes. Antigen concentration (based on protein content) is shown on the x-axis. FIG. 2B shows data for the proliferative response of T-cell line DN1 to *M. tuberculosis* (1 μg protein/ml) requires CD1+ antigen presenting cells (CD1+ APCs). APCs indicated by symbols as follow: no APCs, open square; GM-CSF and IL-4 treated monocytes (CD1+ APCs), closed circles; IFNγ treated monocytes (CD1+), open circles; freshly isolated monocytes (CD1+), open triangles. The number of APCs added to each culture is shown on the x-axis. FIG. 2C shows data indicated that APC's from all donors tested supported the proliferative response of T-cell line DN1 to *M. tuberculosis*. Open bars, T-cells plus APCs without *M. tuberculosis*; solid bars, T-cells plus APCs with *M. tuberculosis* (1 μg protein/ml). APCs were GM-CSF and IL-4 treated peripheral blood mononuclear cells from five unrelated donors. HLA typing confirmed that no allele of the HLA-A, -B, -C, -DR, -DP or -DQ loci was shared among all five donors (data not shown). FIGS. 2D, 2E show data indicating that anti-CD1b mAb specifically inhibited the proliferative response of DN1 (FIG. 2D) and DN1.C7 (FIG. 2E) to *M. tuberculosis* (1 μg protein/ml). APCs were GM-CSF- and IL-4-treated monocytes. Solid bars, proliferative response of T-cells to APCs with *M. tuberculosis* (1 μg protein/ml); dotted lines, response to APCs in the absence of *M. tuberculosis*; "nd," not determined. Monoclonal antibodies used were P3 (control IgG), OKT6 (anti-CD1a), WM-25 (anti-CD1b; Favaloro, E. J., et al., *Disease Markers* 4:261–270 (1986)), 10C3 (anti-CD1c), W6/32 (anti-MHC Class I), and IVA12 (anti-MHC Class II; Shaw, S., *Hum. Immun.* 12:191–211 (1985)).

FIG. 4A. shows for M. tb. CD1b-presented Ag-specific T-cell line DN1. FIG. 4B shows data for DN1 subclone DN1.C7. FIG. 4C shows data for CD1a autoreactive clone BK6. FIG. 4D shows data for CD1c autoreactive clone 3C8.

FIG. 5A shows data for lysis of CD1 T2 transfectants by T-cell line DN1. T2 cells transfected with vector DNA alone (mock transfectant) are indicated by circles, and T2 cells transfected with CD1b by triangles. Open symbols represent target-cells not preincubated with *M. tuberculosis*, and filled symbols represent target-cells preincubated for 12 hours with *M. tuberculosis* (10 ug protein/ml). Flow cytometric analysis showed that incubation of CD1b transfected T2 cells with *M. tuberculosis* had no effect on CD1b expression (data not shown). FIG. 5B shows data indicating that glutaraldehyde fixation of CD1b+ APCs prevents presentation of *M. tuberculosis* to line DN1. CD1b+ APCs (GM-CSF- and IL-4-treated peripheral blood mononuclear cells, PBMCs) were cultured for 12 hours in the presence of *M. tuberculosis* (1 μg protein/ml; "Pulsed APCs") or in medium alone ("Unpulsed APCs"), harvested and an aliquot of each cell suspension was fixed with 0.0125% glutaraldehyde for 30 seconds. The resulting APC preparations were tested for their ability to stimulate proliferation of line DN1 in the absence (open bars) or presence (solid bars) of soluble *M. tuberculosis* antigen (1 μg protein/ml). FIG. 5C shows data for inhibition of CD1b restricted presentation of *M. tuberculosis* by chloroquine. CD1b+ APCs from an HLA-DR7+ individual were pulsed with *M. tuberculosis* antigen for 60 minutes at 37° C. in the presence of the indicated concentration of chloroquine, fixed with glutaraldehyde, and used as APCs in proliferative assays with line DN1 (solid circles) or with the *M. tuberculosis* specific, HLA-DR7$^+$ restricted CD4$^+$ T-cell line DG.1 (open triangles). Results are expressed as percent inhibition of responses compared to fixed APCs pulsed with *M. tuberculosis* in the absence of chloroquine, and are representative of three similar experiments.

Figure 6:
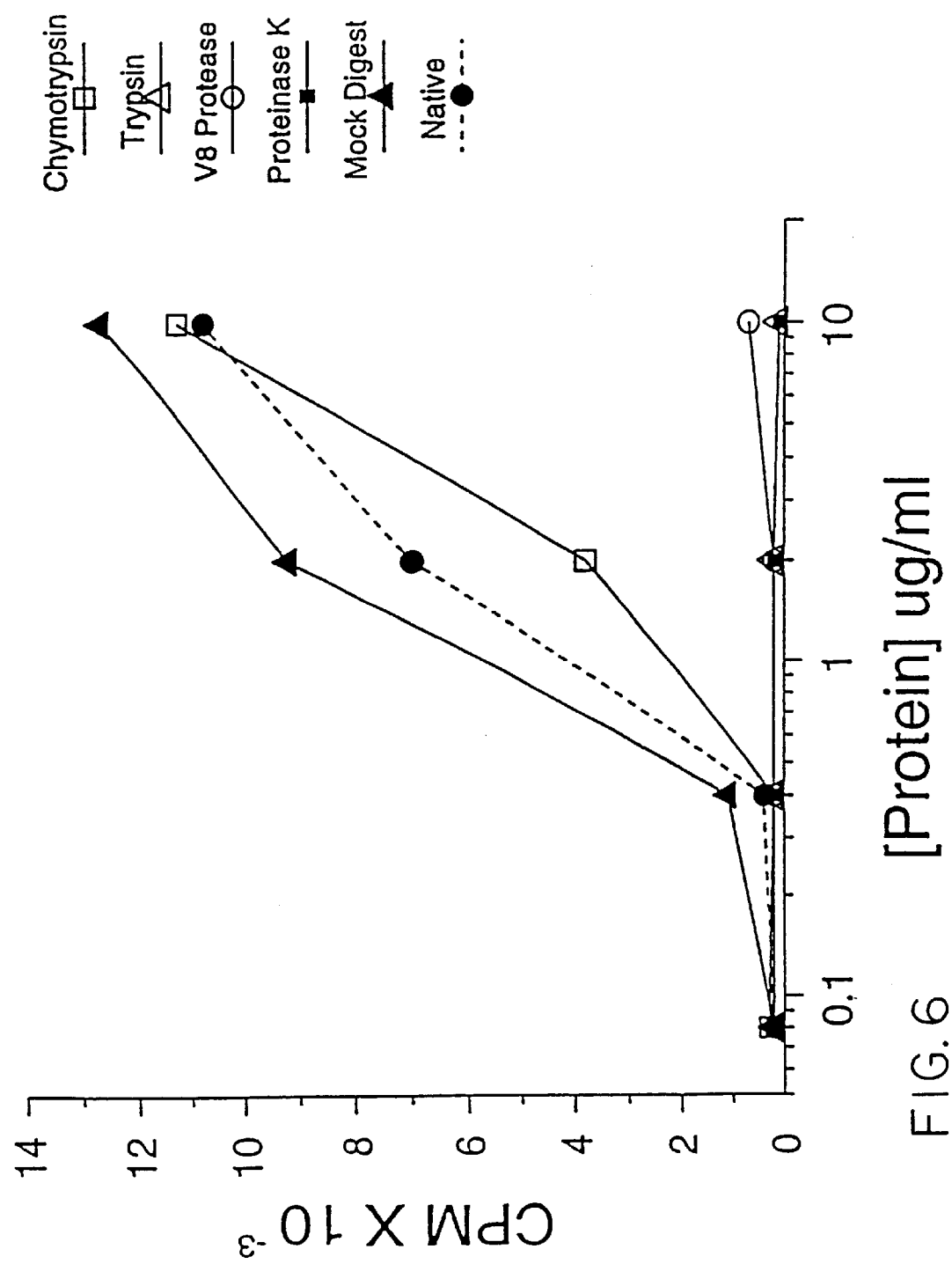

FIG. 6 shows data indicating the effect on the proliferative response of T-cell line DG.1 to *M. tuberculosis* antigen of digestion of antigen with the indicated proteases.

Figure 7:
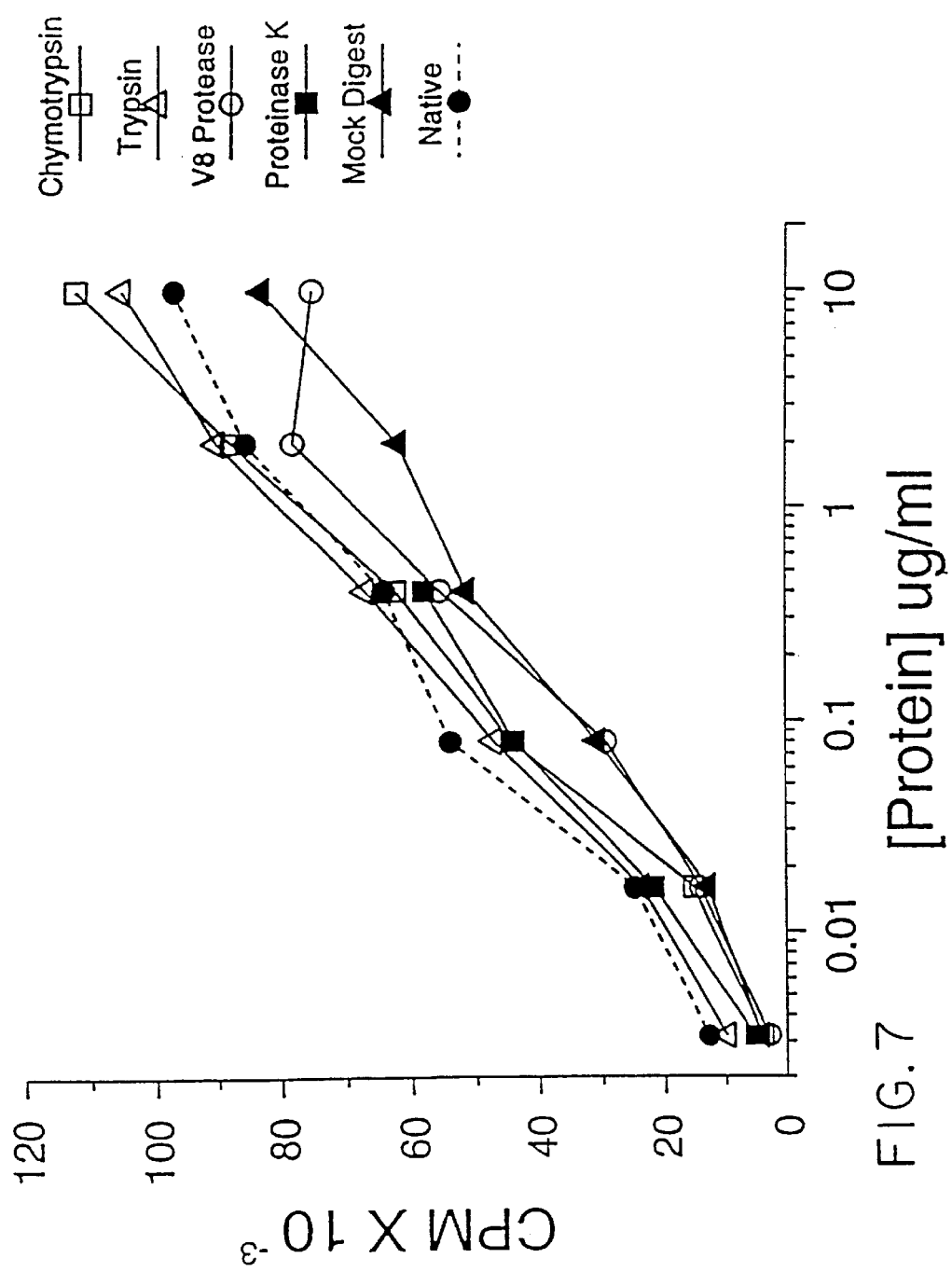

FIG. 7 shows data for the effect on the proliferative response of T-cell line DN1 to *M. tuberculosis* antigen of digestion of antigen with the indicated proteases.

Figure 8:
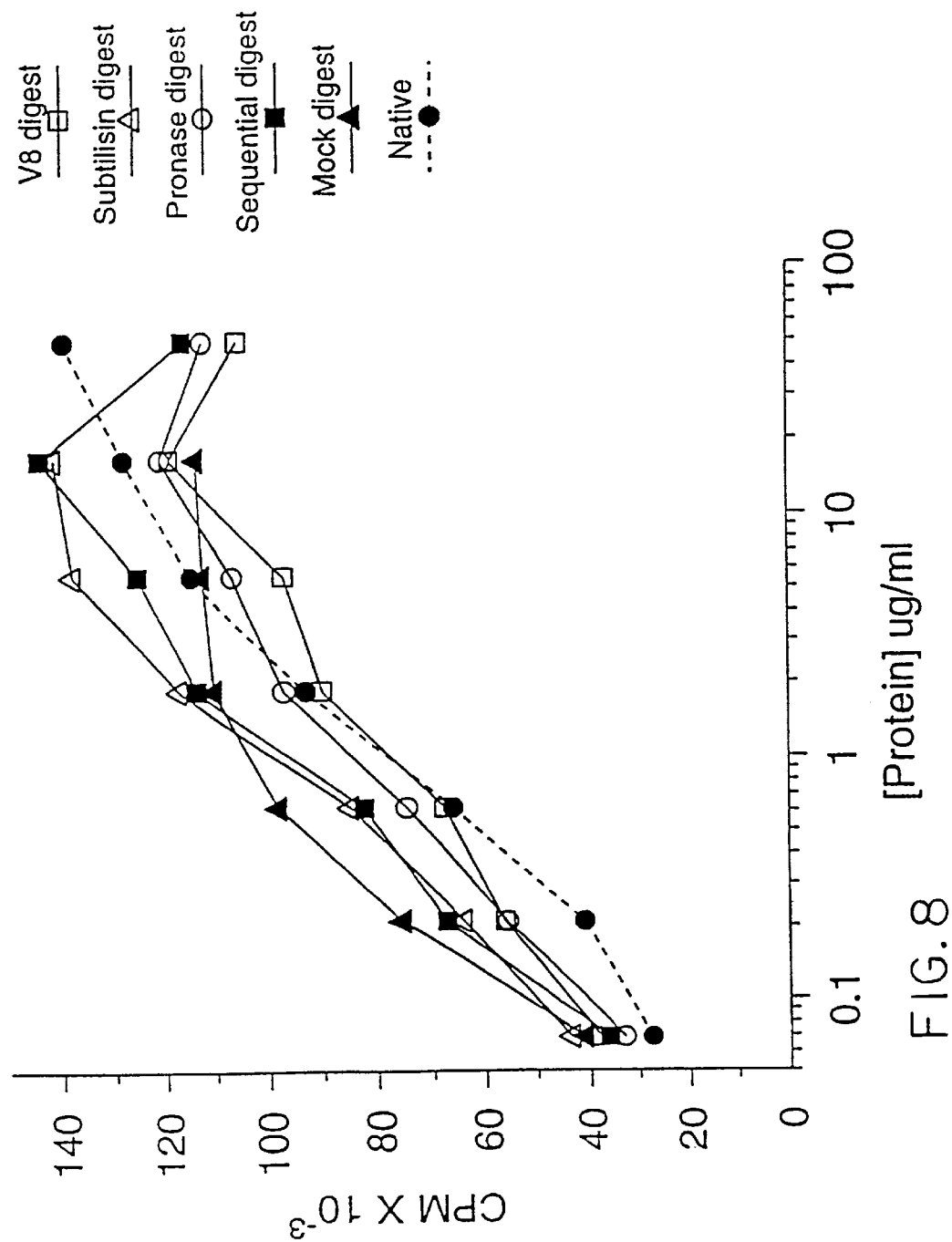

FIG. 8 shows data for the effect on the proliferative response of T-cell line DN1 to *M. fortuitum* antigen of digestion of antigen with the indicated proteases.

Figure 9A:
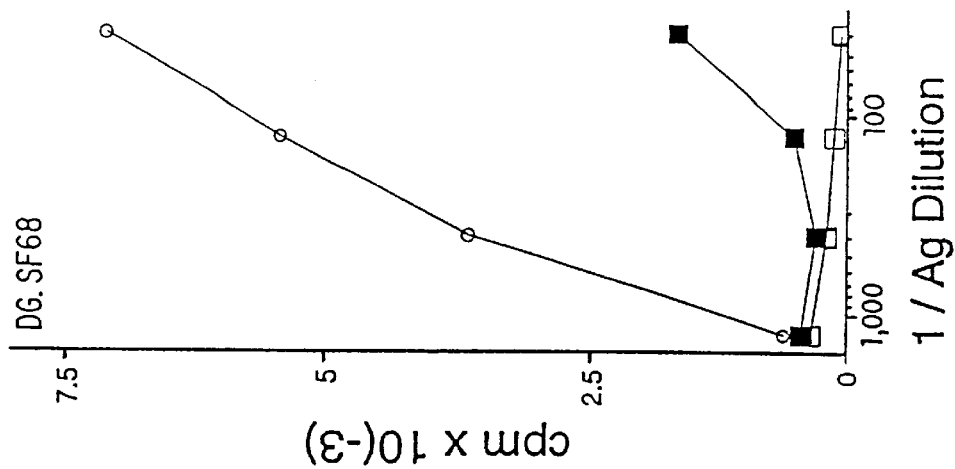
Figure 9B:
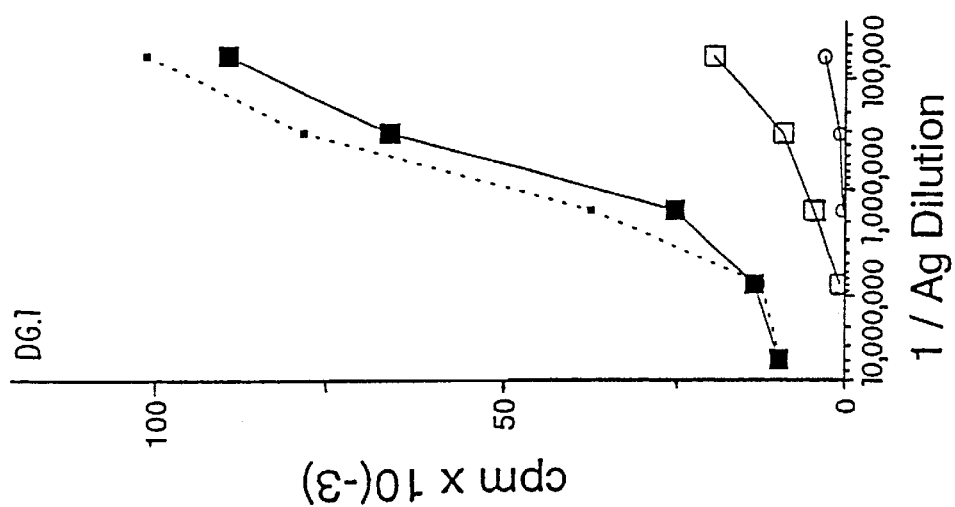
Figure 9C:
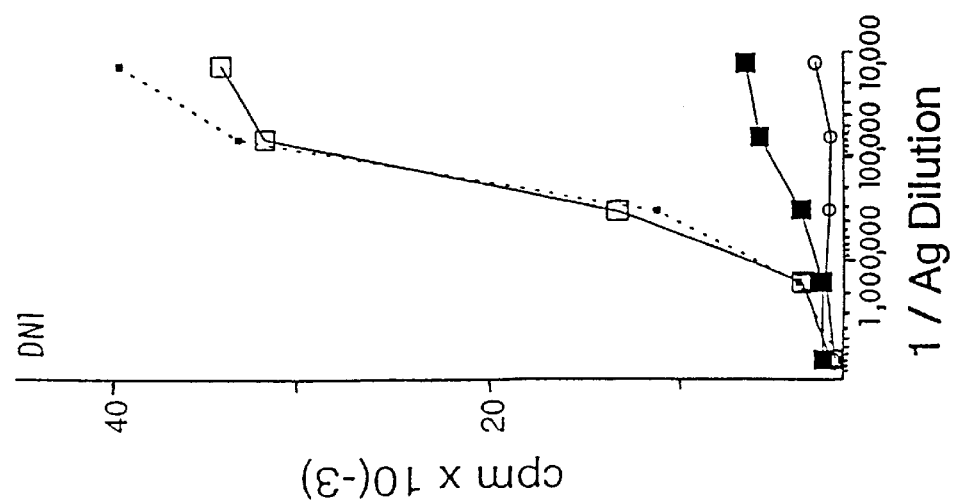

FIGS. 9A–C shows data indicating that a Mycobacterial antigen recognized by a DN α:β TCR$^+$ T-cell line quantitatively partitions into the organic phase after extraction with organic solvents and is CD1b restricted. Extraction with organic solvents differentiates the CD1b-restricted Mycobacterial antigen from Mycobacterial antigens recognized by a conventional MHC class II restricted CD4$^+$ α:β TCR$^+$ T-cell line and the small nonprotein Mycobacterial ligand recognized by DN γ:δ (Vγ2Vδ2) TCR$^+$ T-cells. Pfeffer, K., et al., *J. Immunology* 148:575–583 (1992). Total Mycobacterial sonicates were extracted with chloroform/methanol/H$_2$O and the resultant three phases were assayed by culturing T-cells with CD1$^+$ monocytes and the indicated dilutions of the various antigen preparations. FIG. 9A shows data for the proliferative response of the CD1b-restricted DN T-cell line DN1 to total mycobacterial sonicates (■, dashed line), organic phase (□, solid line), aqueous phase (○, solid line) or interface (■, solid line). Antigen concentration along the x axis is depicted as 1/dilution normalized to the standard total sonicate preparation. FIG. 9B shows data for the proliferative response of the HLA-DR7 (MHC) restricted Mycobacterial specific CD4$^+$ T-cell line DG.1 to Mycobacterial fractions after extraction with organic solvents. FIG. 9C shows data for the proliferative response of the Vγ2Vδ2 T-cell clone DG.SF68 to Mycobacterial fractions after extraction with organic solvents.

Figure 10:
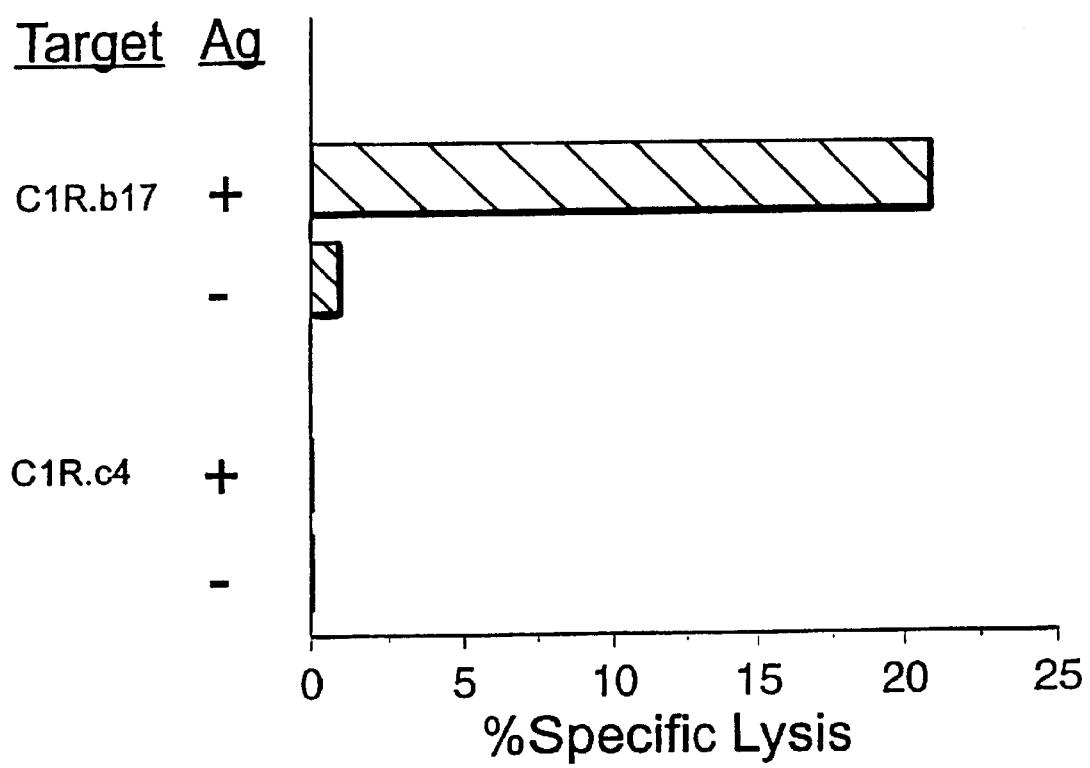

FIG. 10 shows the cytolytic response of the DN1 line to CD1 transfectants of C1R cells pulsed with Mycobacterial antigen preparations. CD1b or CD1c transfectants (Porcelli, S., et al., *Nature* 341:447–450 (1989)) of C1R lymphoblastoid cells were used as targets in a standard cytolytic assay pulsed either with *M. tuberculosis* antigen preparations after extraction with organic solvents (+) or media alone (–). Recognition by the T-cell line DN1 of C1R cells transfected with CD1b occurs only when pulsed with antigen. No antigen specific recognition occurs for CD1c$^+$ targets.

Figure 11:
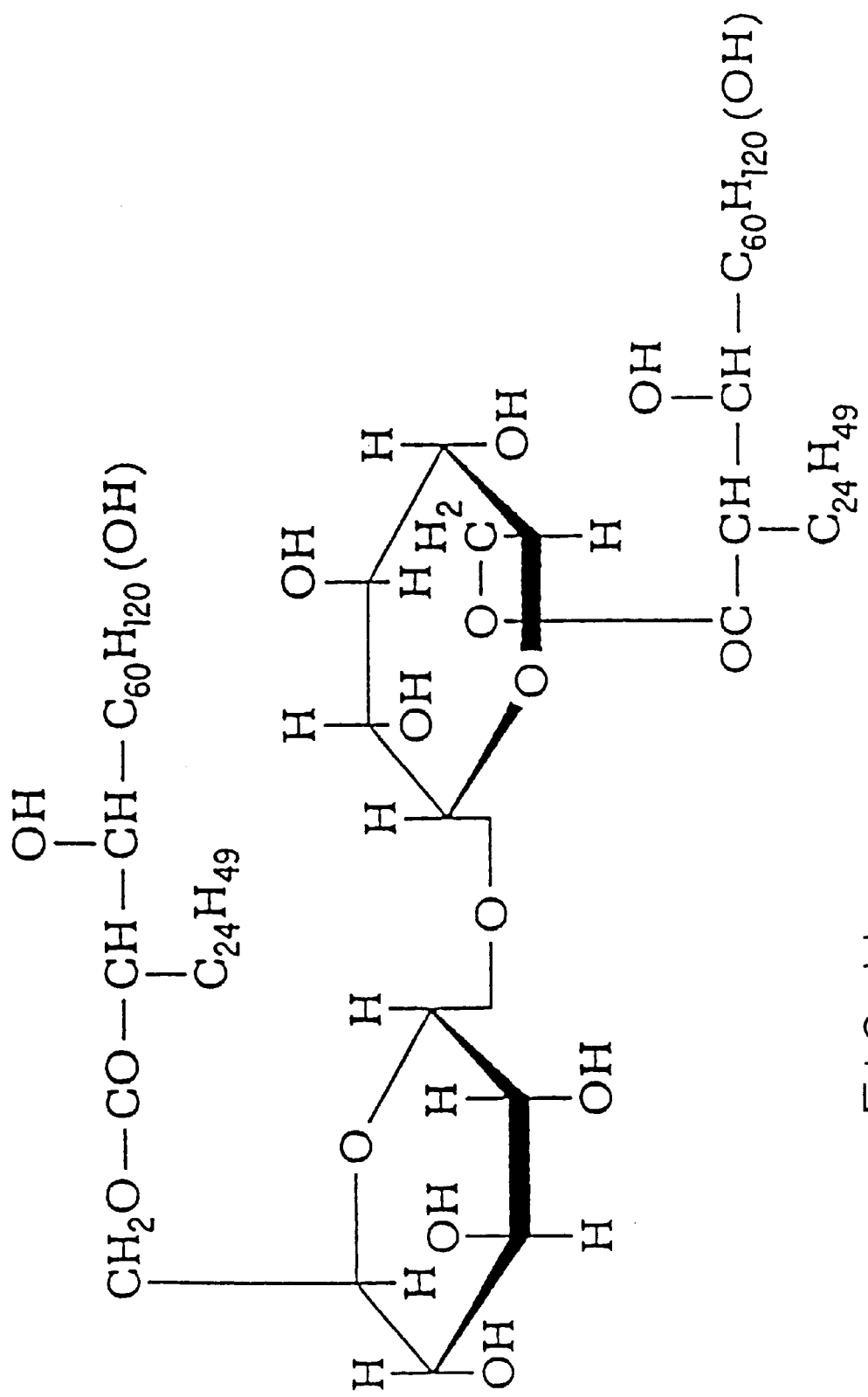

FIG. 11 shows the chemical structure of 6,6-trehalose dimycolate (cord factor).

Figure 12C:
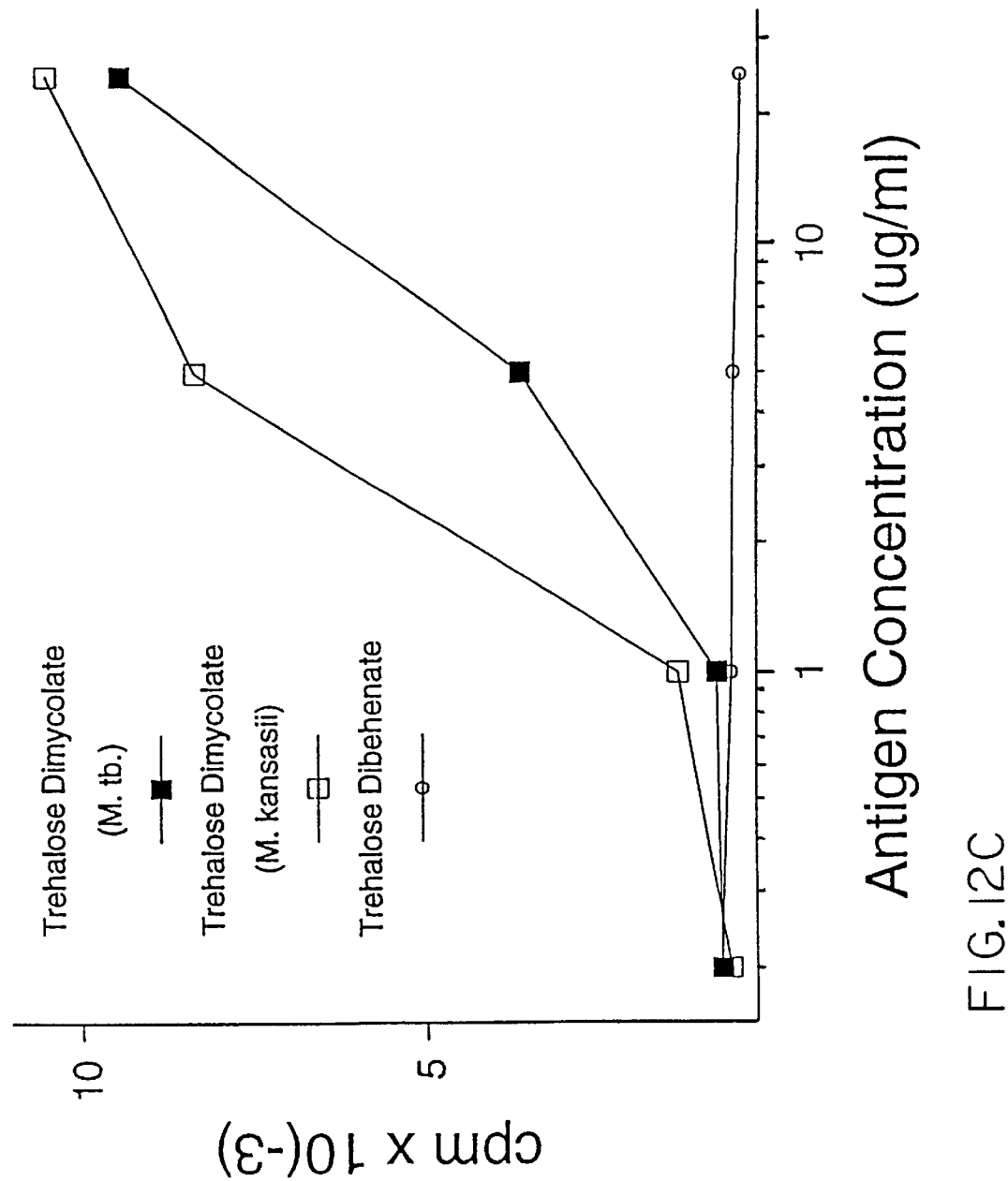

FIGS. 12A–E shows data indicating that the Mycobacterial antigen recognized by the CD1b-restricted T-cell line DN1 is mycolic acid. FIGS. 12A, 12B show data indicating that the proliferative response of the CD1b-restricted T-cell line DN1 correlates with mycolic acid peaks on reverse phase C18 HPLC. The purified Mycobacterial acyl chain fraction containing all the CD1b-restricted antigen was chromatographed using reverse phase HPLC and the resulting fractions assayed for the ability to stimulate a proliferative response by the T-cell line DN1. FIG. 12A shows data for display of the absorbance spectrum at 254 angstrom (expressed as optical density units, OD, x 10$^{-4}$) (solid line) of the eluted material and the corresponding methylene chloride concentration (dotted line) of the elution gradient. The large absorbance peak eluting between 2 to 6 minutes is free bromophenacyl bromide, the derivitizing agent. FIG. 12B shows data for the proliferative response of the T-cell line DN1 to each one minute fraction. The CD1b-restricted antigen response is seen as a broad peak correlating with mycolic acid. FIG. 12C shows data indicating that saponified 6,6-trehalose dimycolate (cord factor), but not saponified trehalose dibehenate, stimulates a proliferative response by the CD1b restricted T-cell line DN1. Mycolic acids were generated by saponification of purified trehalose dimycolate from either *M. tuberculosis* (H37Ra) or *M. kansasii*. Trehalose dibehenate (synthetic cord factor) was treated in an identical fashion. Antigen concentration is expressed in μg/ml of cord factor along the x axis. FIGS. 12D, 12E show data for the reversed phase HPLC analysis of purified trehalose dimycolate from *M. tuberculosis* (H37Ra) results in the stimulation of the CD1b-restricted T-cell line DN1 by fractions corresponding to mycolic acid peaks. The saponified trehalose dimycolate of *M. tuberculsis* was chromatographed as in the experiment shown in FIG. 12A (FIG. 12D), and fractions assayed for the ability to induce a proliferative response by the line DN1 (FIG. 12E). As in FIG. 12A, bioactivity correlates with early mycolic acid peaks.

Figure 13:
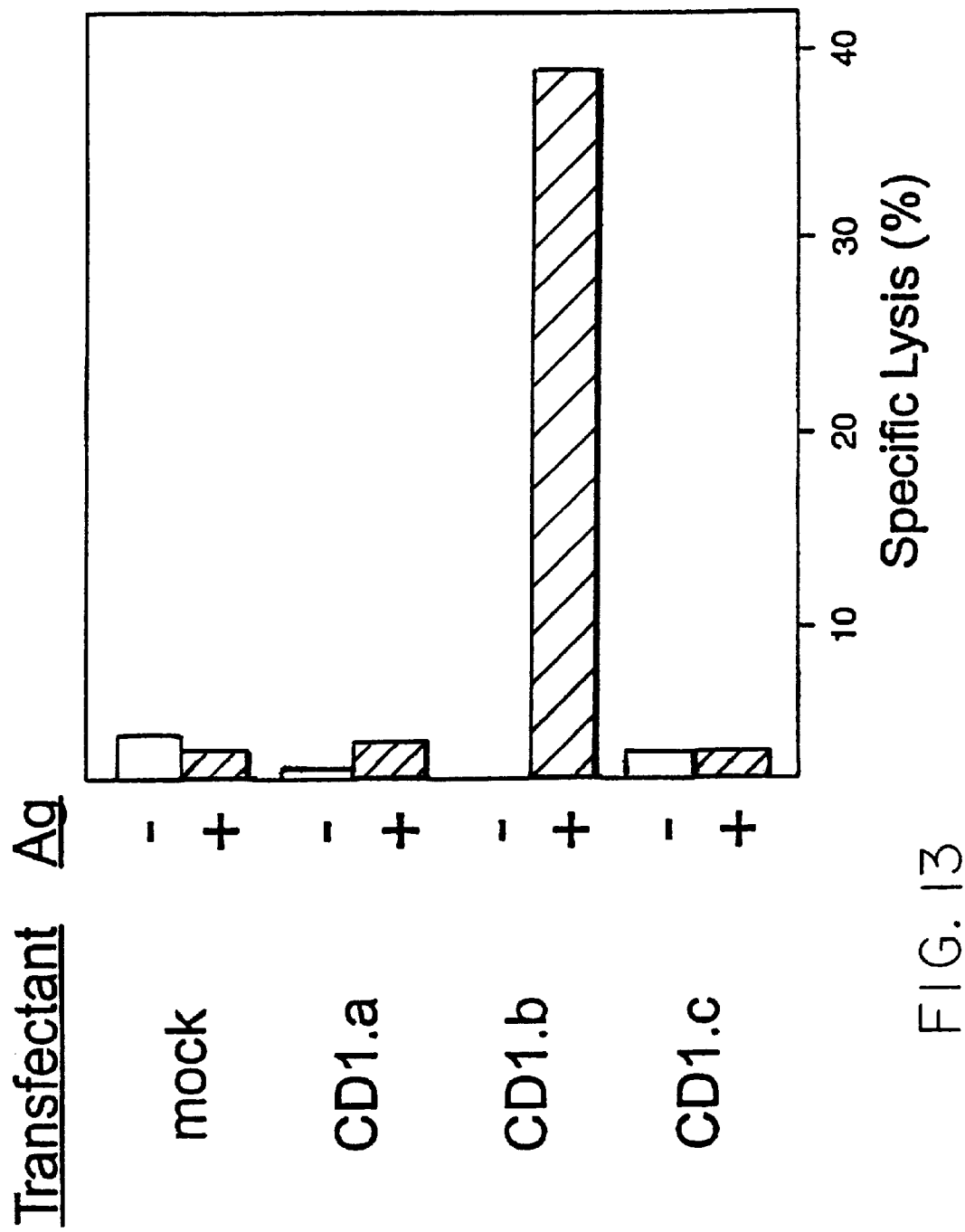

FIG. 13 shows data for the cytolytic response of the DN1 T-cell line to CD transfectants of C1R cells pulsed with mycolic acid prepared from M. tb. cord factor (Sigma) by saponification. CD1a, CD1b, CD1c or mock transfectants of C1R lymphoblastoid cells were pulsed with mycolic acids prepared from trehalose dimycolate (+) or media alone (–) and used as targets in cytolytic assays, the results of which are given as % specific lysis.

FIGS. 14A–C shows data indicating that mycolic acid is not mitogenic, but a specific antigen restricted by CD1b and recognized by the T-cell line DN1. Four T-cell lines specific for Mycobacteria and two additional T-cell lines were tested for the ability to respond to either total *M. tuberculosis* sonicates, mycolic acid preparations from purified cord factor or HPLC purified mycolic acids from either M. tb. sonicates or cord factor. The responses of three representative Mycobacterial specific T-cell lines are shown, DN1 (■) (DN, CD1b-restricted, α:δ TCR$^+$), DG.1 (□) (CD4$^+$, HLA-DR7 restricted, α:δ TCR$^+$) and DN6 (○) (DN, CD1c-restricted, α:δ TCR$^+$. APCs for all six T-cell lines tested were identically GM-CSF- and IL-4-treated (CD1$^+$) PBMCs from an HLA-DR7 positive individual. FIG. 14A (upper panel) shows data for the proliferative responses of three Mycobacterial specific T-cell lines to total sonicates of M. tb. (H37Ra, Sigma). Antigen concentration is displayed on the x axis as cpm x 10$^{-3}$. The three T-cell lines shown all respond to total Mycobacterial sonicates. FIG. 14B (middle panel) shows data for the proliferative response to HPLC-purified mycolic acids isolated from M. tb. sonicates. Only the CD1b-restricted T-cell line DN1 responds to purified mycolic acid. FIG. 14C (bottom panel) shows data for the proliferative responses to HPLC-purified mycolic acids generated from purified M. tb. cord factor (Sigma). Only the CD1b-restricted T-cell line DN1 proliferates in response to cord factor mycolic acids. Not shown are three additional T-cell lines tested in the same experiment, SP-F3 (Roncarlo, M. G., et al., *J. Exp. Medicine* 168:2139–2152 (1988)) (CD4$^+$ α:δ TCR$^+$, DR restricted, tetanus toxoid specific), CP.1.15 (Morita, C. T., et al., *Eur. J. Immunol.* 21:2999–3007 (1991)) (DN, Vγ2Vδ2 TCR$^+$, Mycobacterial specific), BK6 (Porcelli, S., *Nature* 341:447–450 (1989) (DN, α:δ TCR+, autoreactive to CD1a). All three did not respond to purified mycolic acids, but two proliferated in response to their specific antigen (tetanus toxoid—SP-F3,<1 kDa *M. tuberculosis* preparation—CP.1.15). BK6 exhibits cytolytic activity against CD1a, but is unable to proliferate in response to CD1a+ APCs of any type tested. Porcelli, S., *Nature* 341:447–450 (1989).

Figure 15A:
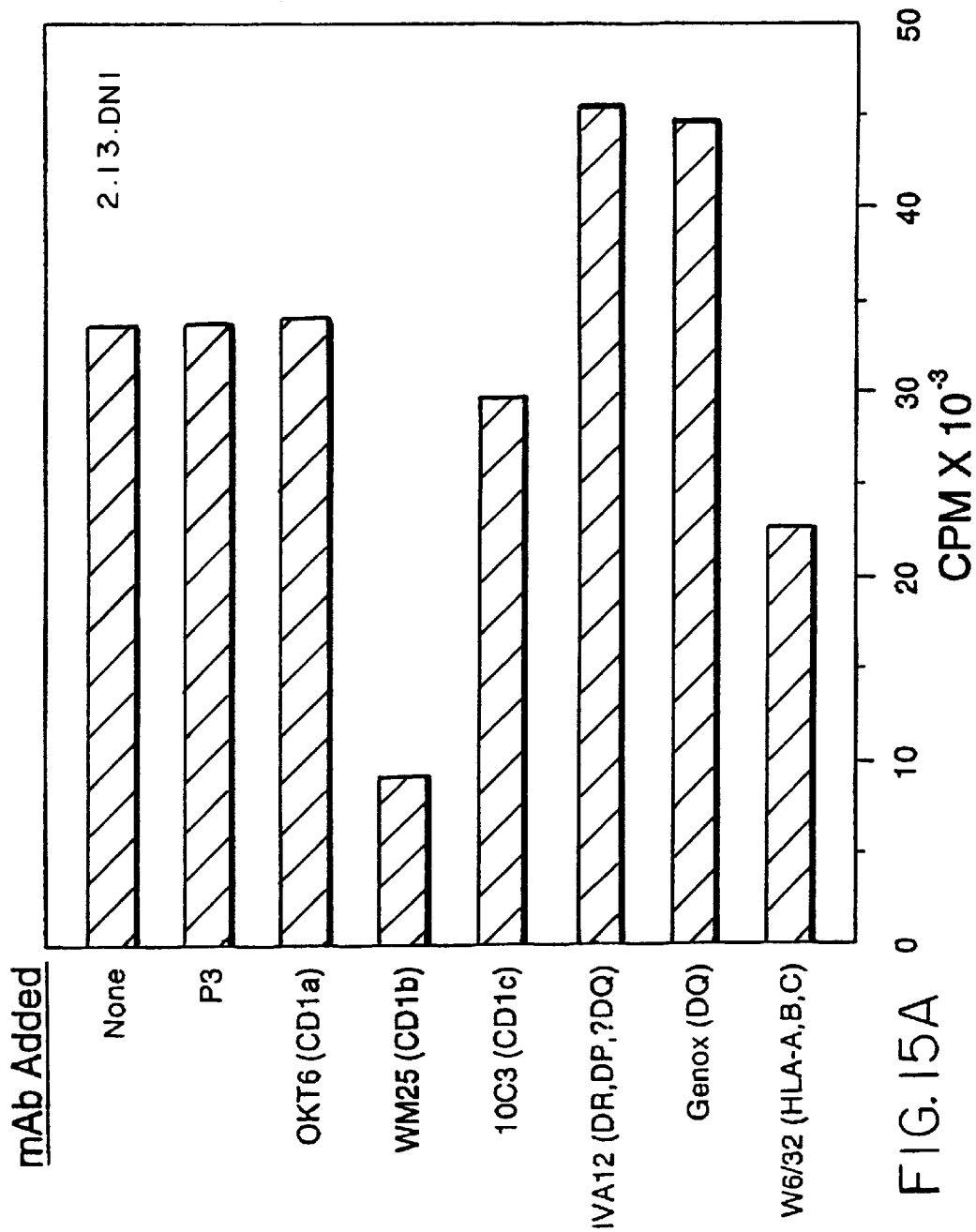
Figure 16A:
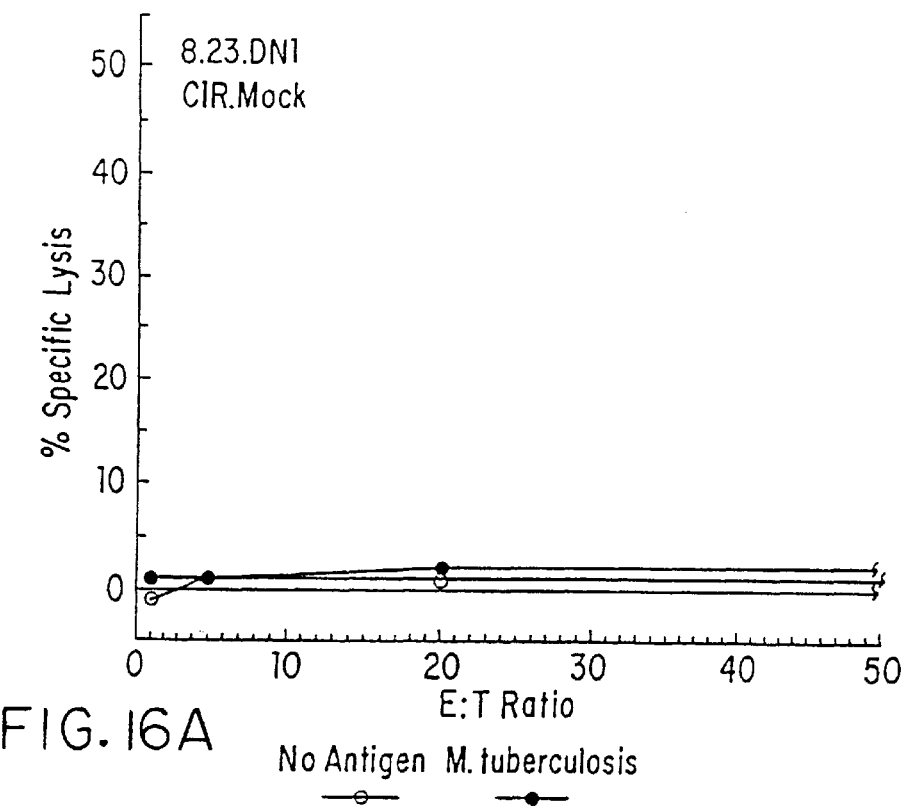
Figure 16B:
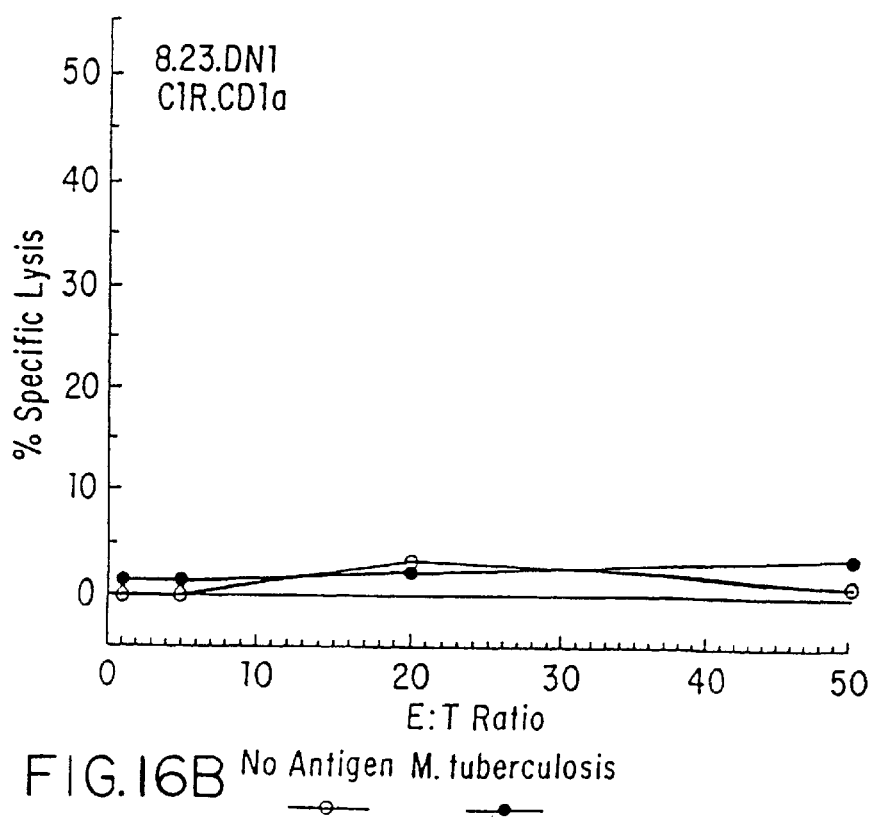
Figure 16C:
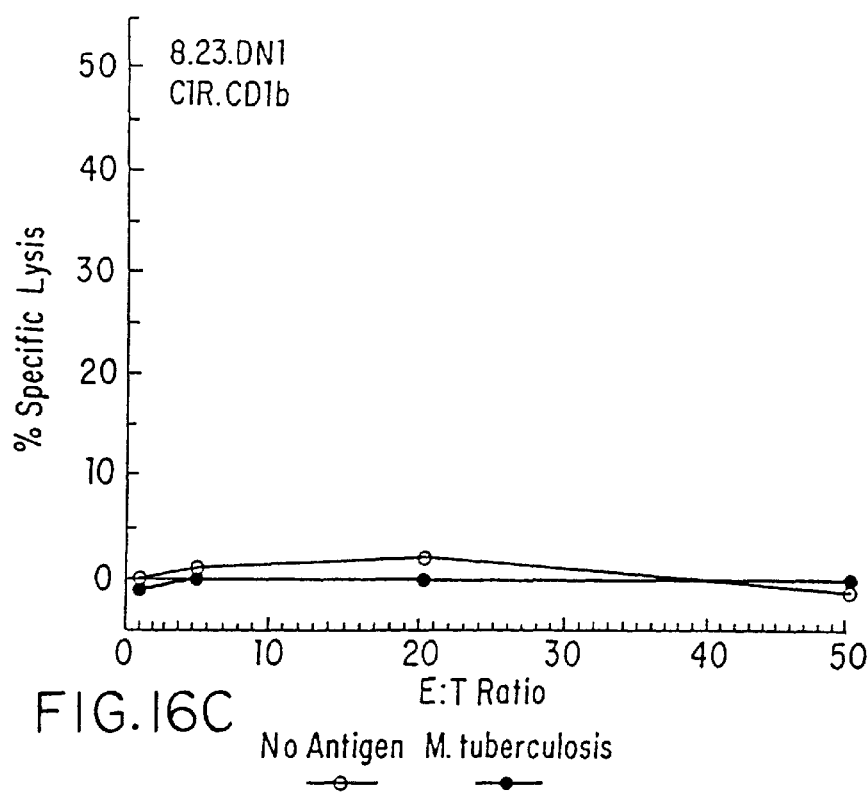
Figure 16D:
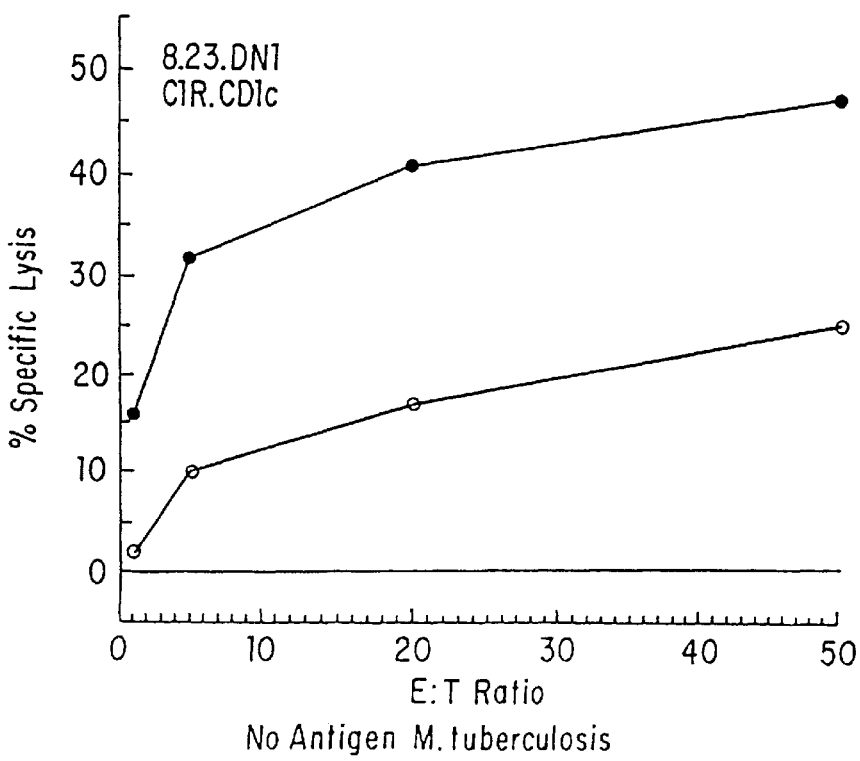
Figure 17D:
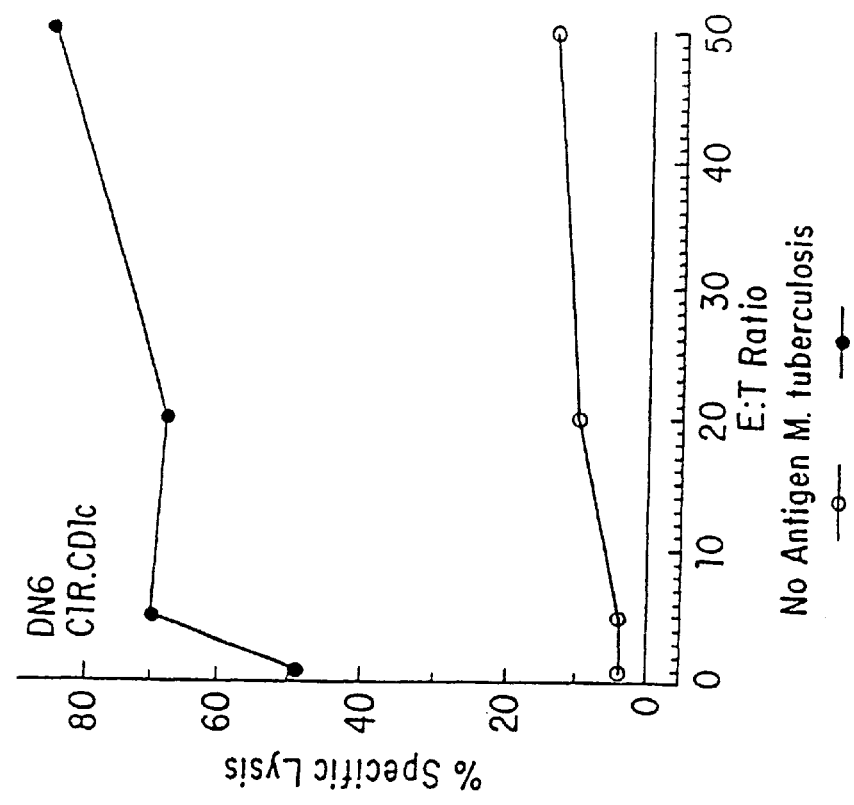
Figure 17C:
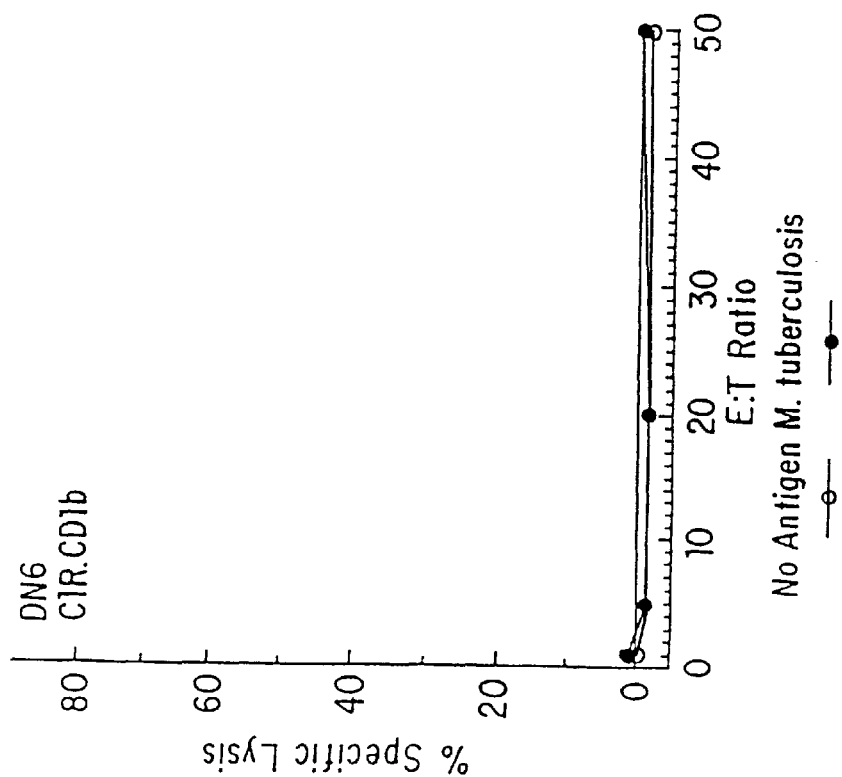

FIGS. 15A–B shows data indicating the effect of the indicated monoclonal antibodies on the proliferative response of T-cell line 2.13.DN1 (FIG. 15A) and 8.23.DN1 (FIG. 15B).

FIGS. 16A–D shows data for CD1c-restricted presentation of *M. tuberculosis* antigen to T-cell line DN2. The results of cytolytic assays of CR1 cells transfected with vector (mock, FIG. 16A) and with DNA molecules encoding the indicated CD1 protein (CD1a, CD1b and CD1c) (FIGS. 16B, 16C, 16D, respectively), wherein the transfected cells were either preincubated with (filled circles) or without (open circles) *M. tuberculosis*.

FIGS. 17A–D shows data for CD1c-restricted presentation of *M. tuberculosis* antigen to T-cell line DN6. The results of cytolytic assays of CR1 cells transfected with vector (mock, FIG. 17A) and with DNA molecules encoding the indicated CD1 protein (CD1a, CD1b and CD1c) (FIGS. 17B, 17C, 17D, respectively), wherein the transfected cells were either preincubated with (filled circles) or without (open circles) *M. tuberculosis*.

Figure 18:
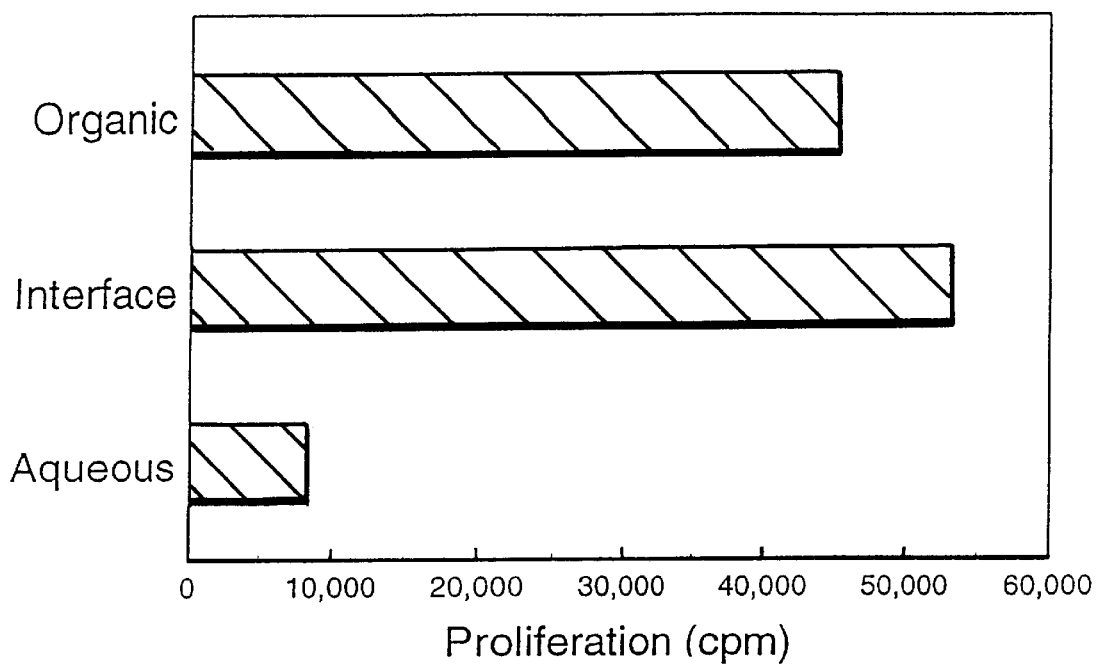

FIG. 18 shows data for the prliferative response of the CD1c-restricted cell line DN6 to M. tb. antigens in sonicates after extraction of the antigens with organic solvents. Proliferation is in cpm ($^3$H thymidine incorporation) displayed on the y axis. APCs were CD1 expressing monocytes. Antigens were titered over 6 logs and the results from a representative point (1:3,750 dilution of antigen) are shown. Background cpm (defined from a media alone control) were subtracted from all values.

Figure 19:
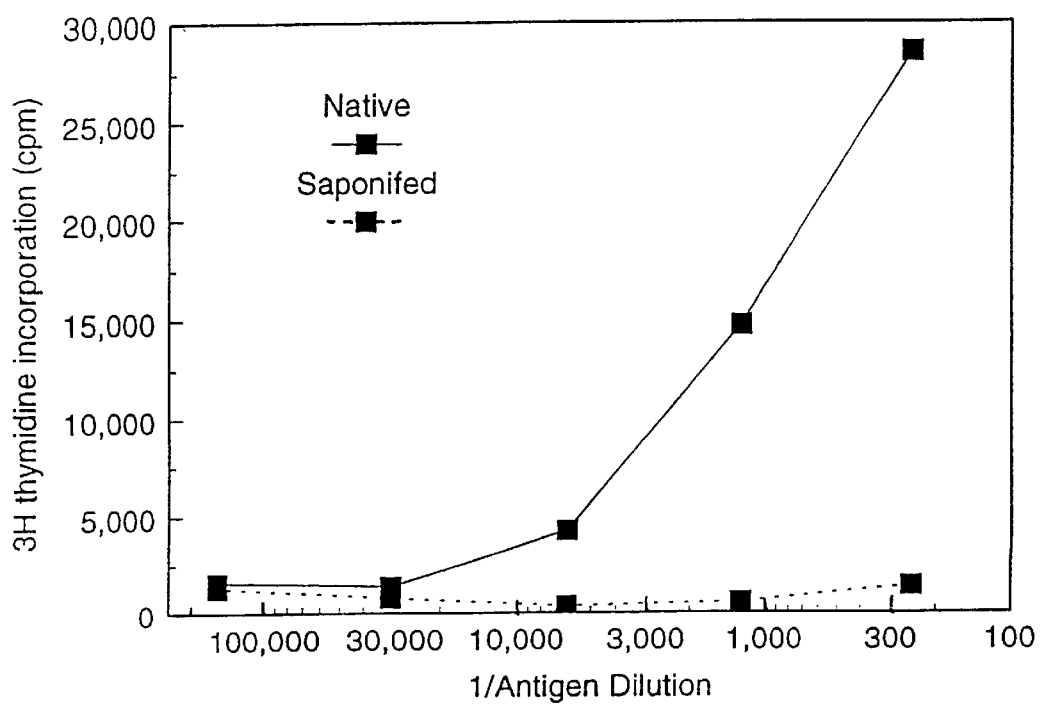

FIG. 19 shows data for the proliferative response of the CD1c-restricted cell line DN6 to M. tb. antigens in sonicates before and after saponification of the antigens. Proliferative response in cpm is displayed on the y axis and the concentration of antigen (shown as 1/dilution) is displayed on the x axis. The equivalent of 10 mg of M. tb. (strain H37Ra; Difco) was sonicated in PBS and was either used directly or first saponified. All antigen dilutions were normalized to the standard initial concentration of 200 mg lyophilized bacteria in 5 ml.

Figure 20A:
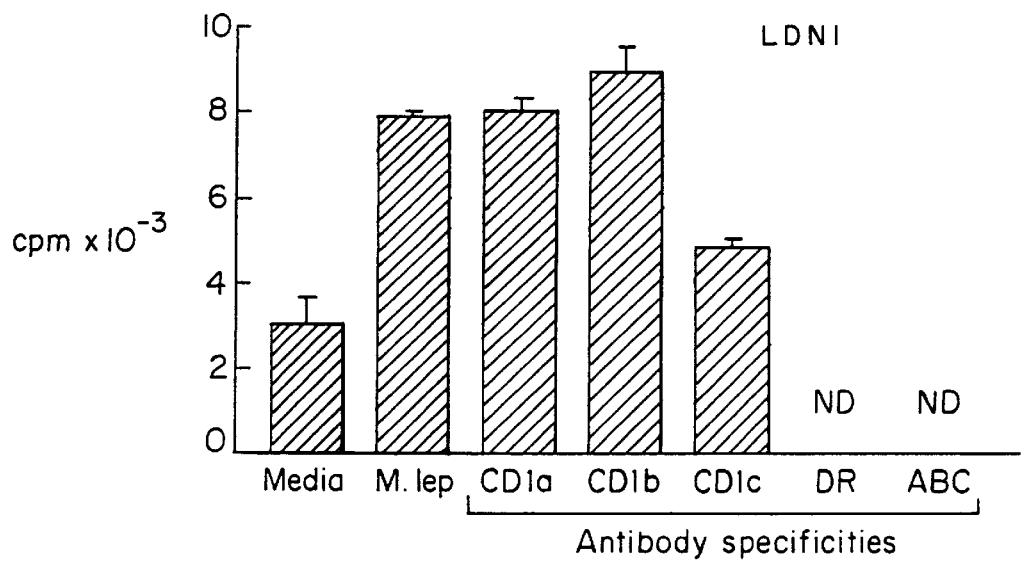
Figure 20B:
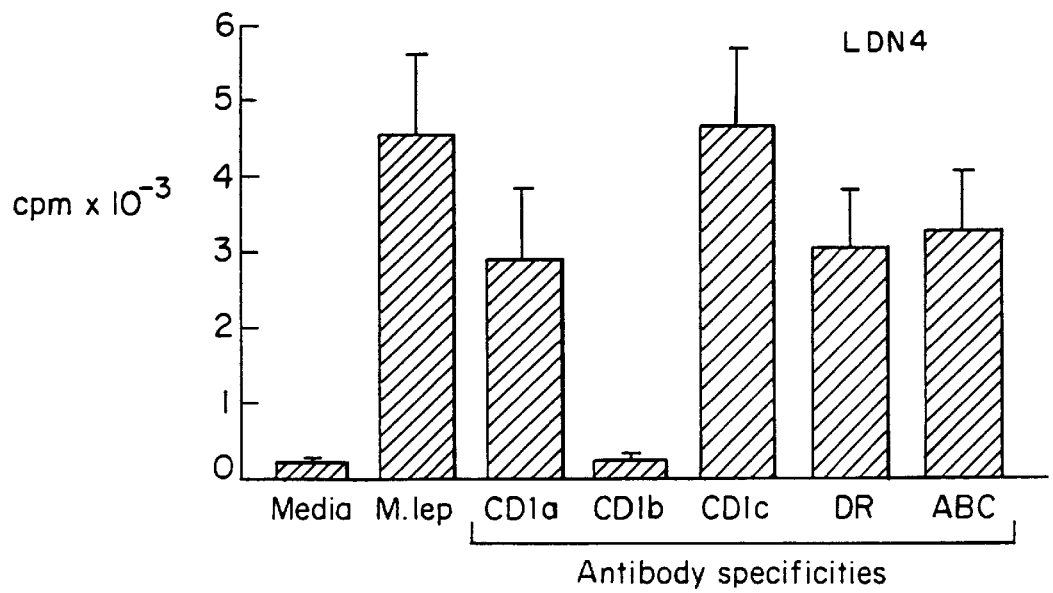

FIGS. 20A–B shows data indicating that DN α:β TCR+ T-cell lines from leprous skin lesions are CD1-restricted. FIG. 20A (upper panel) shows data indicating that anti-CD1c mAb specifically inhibited the proliferative response of T-cell line LDN1 to *M. leprae*. FIG. 20B (lower panel) shows data indicating that anti-CD1b mAb specifically inhibited the proliferative response of T-cell line LDN4 to *M. leprae*.

Figure 21:
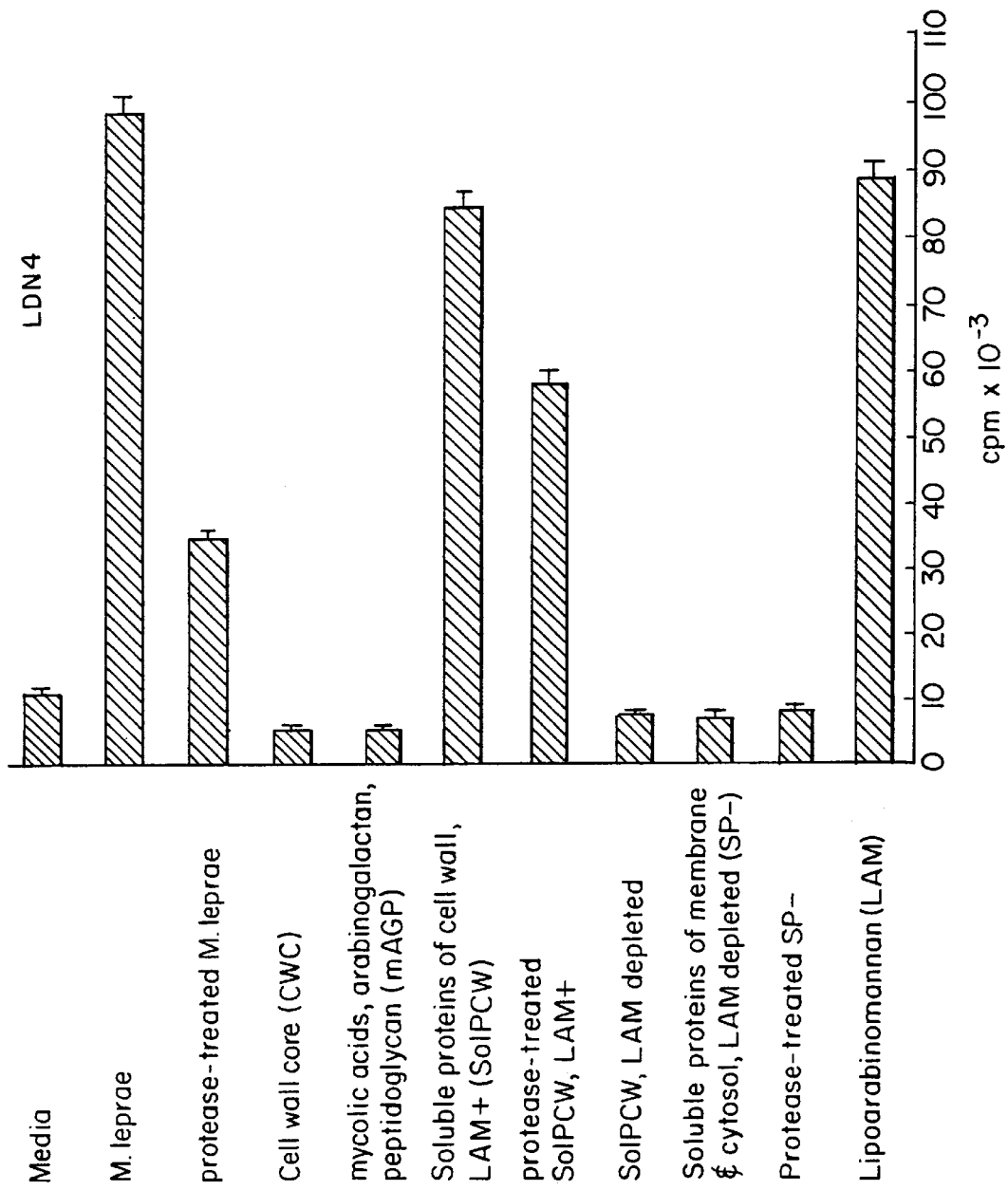

FIG. 21 shows data for the proliferative response of T-cell line LDN4 to the indicated cellular fractions of *M. leprae*.

Figure 22:
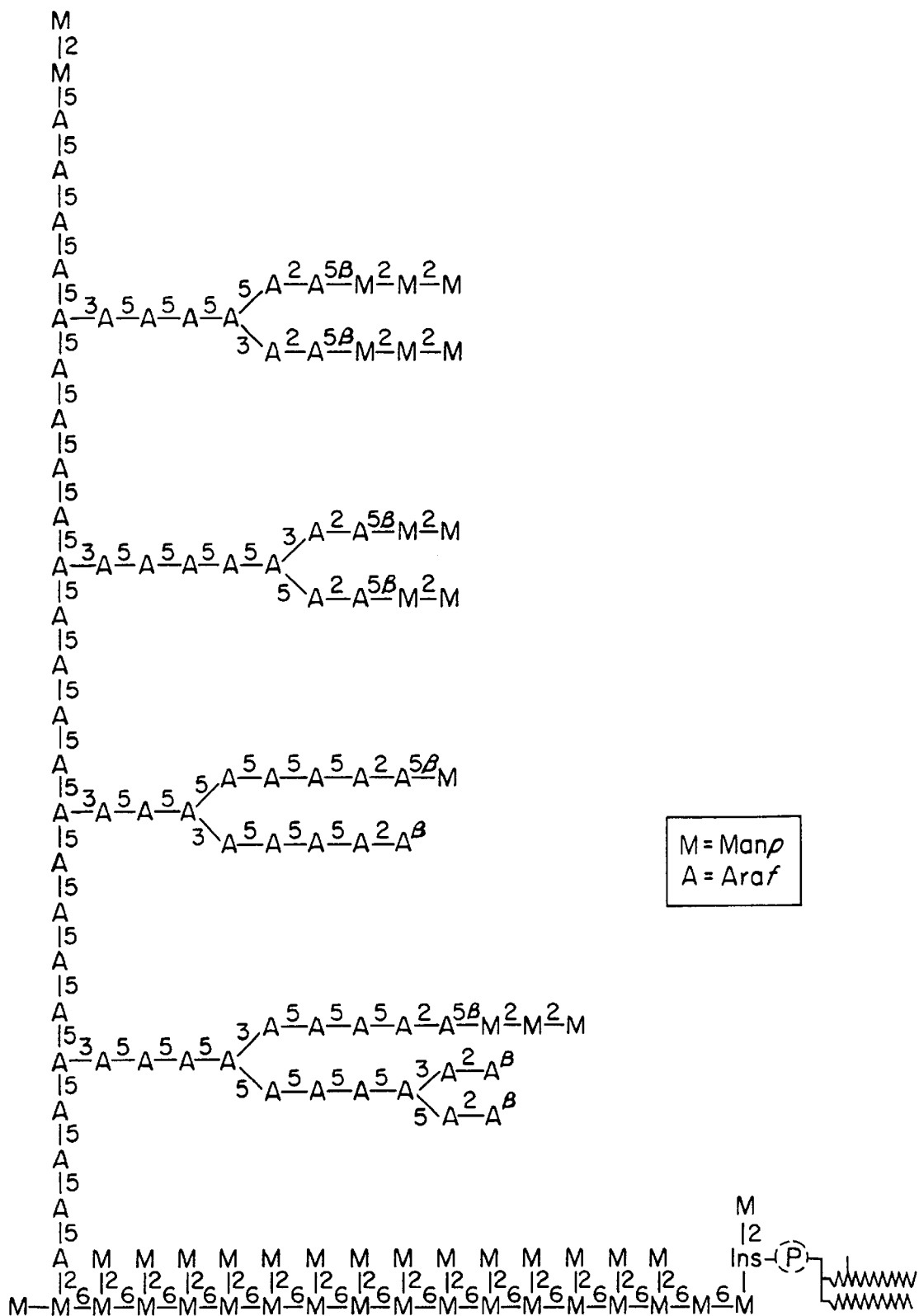

FIG. 22 shows the chemical structure of lipoarabinomannan (LAM). Abbreviations: Manp=mannopyranose; Araf=arabinofurnaose.

Figure 23:
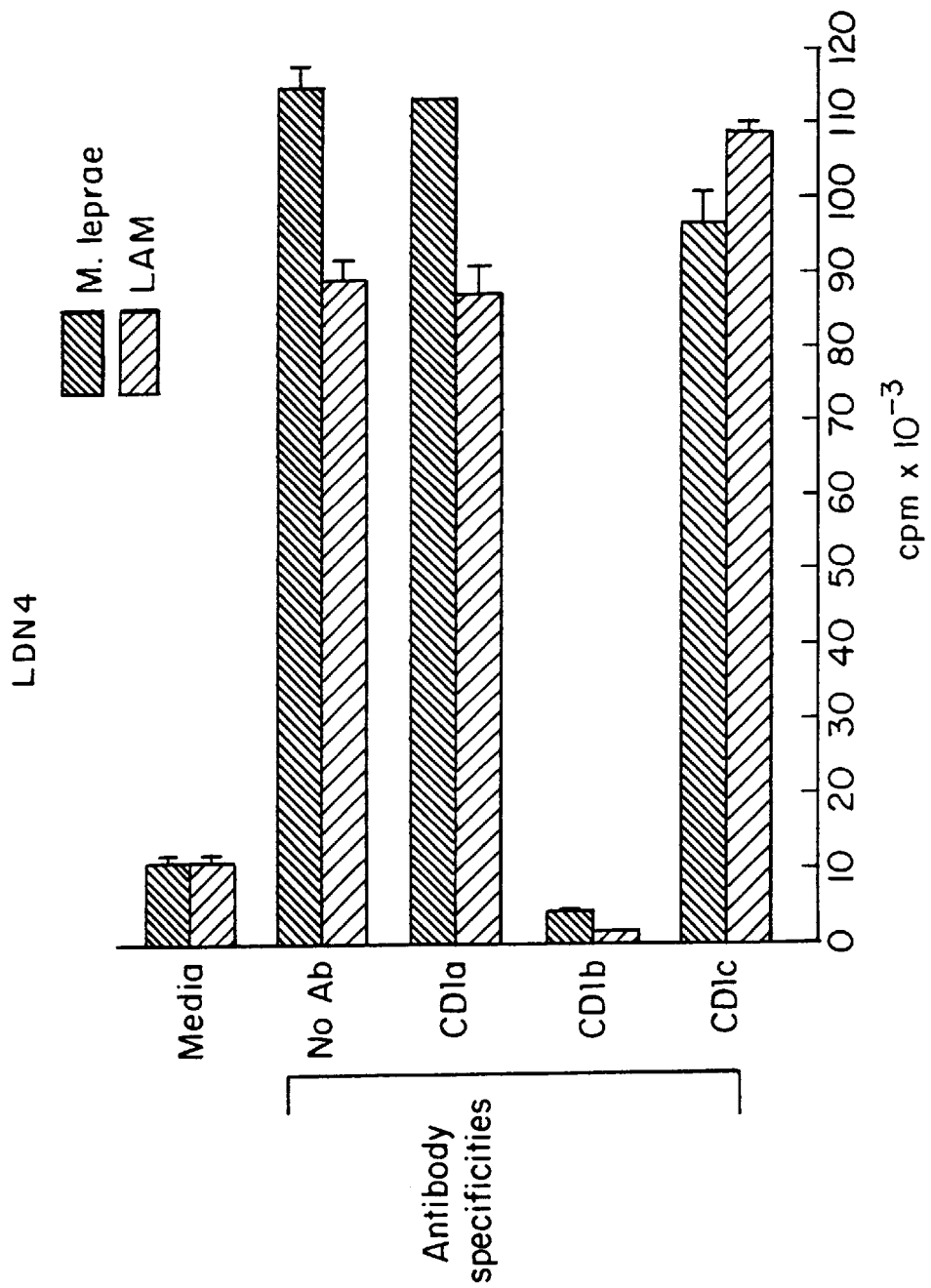

FIG. 23 shows data indicating that the T-cell line LDN4 responds to LAM in a CD1b-restricted manner.

Figure 24:
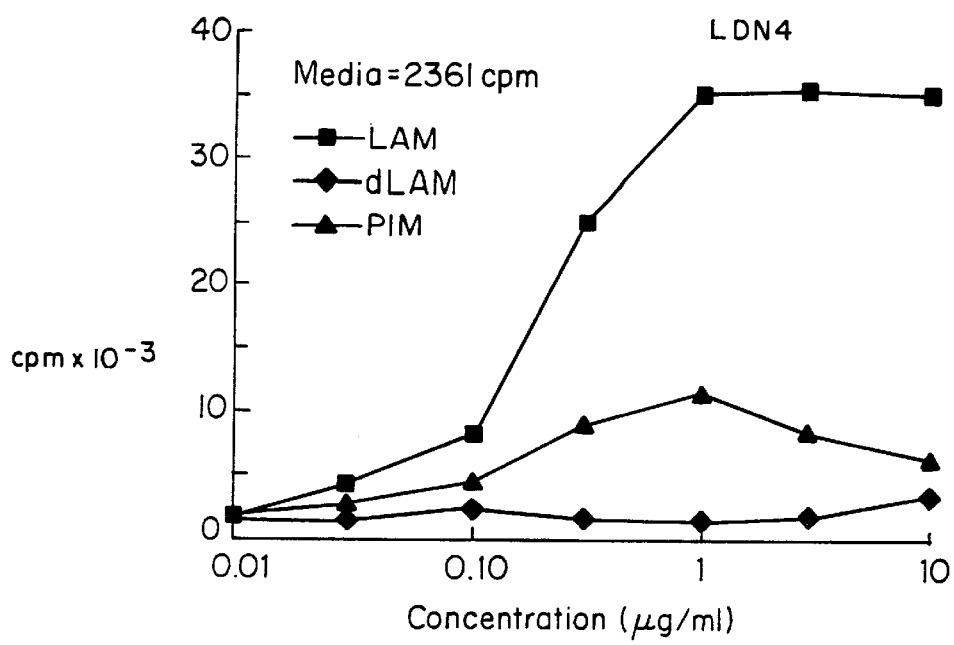

FIG. 24 shows data for the response of T-cell line LDN4 to LAM derivatives. Abbreviations: dLAM=dacylated LAM; PIM=phosphatidylinositol mannoside.

Figure 25:
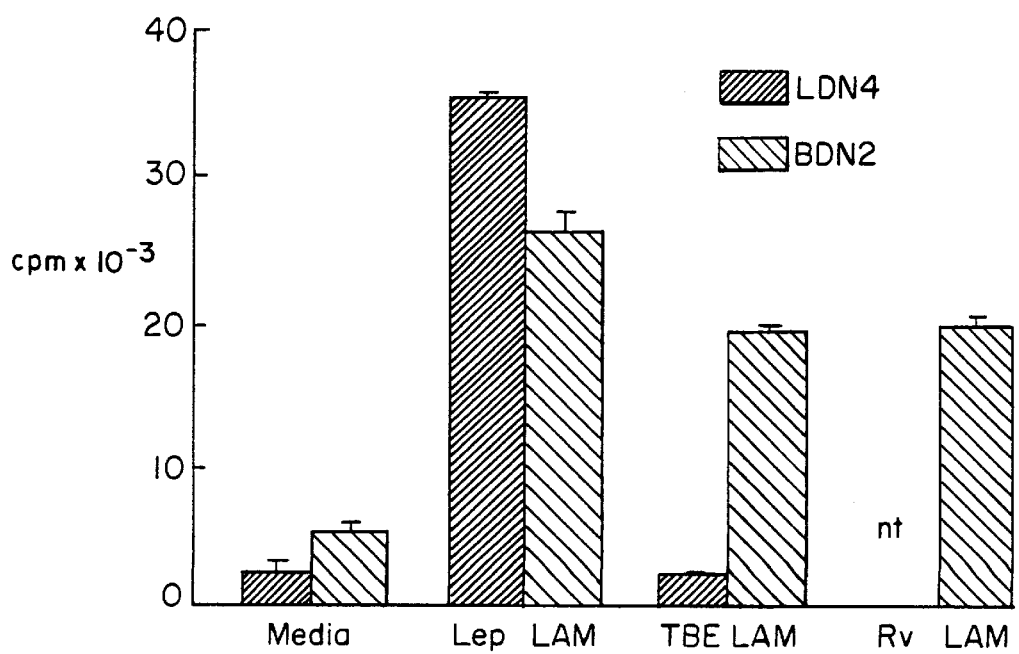

FIG. 25 shows data indicating that the T-cell line BDN2 responds to LAM from *M. leprae* (Lep LAM) as well as LAM from a clinical isolate of *M. tuberculosis* (TBE LAM) and a virulent laboratory strain of *M. tuberculosis* (Rv LAM).

Figure 26A:
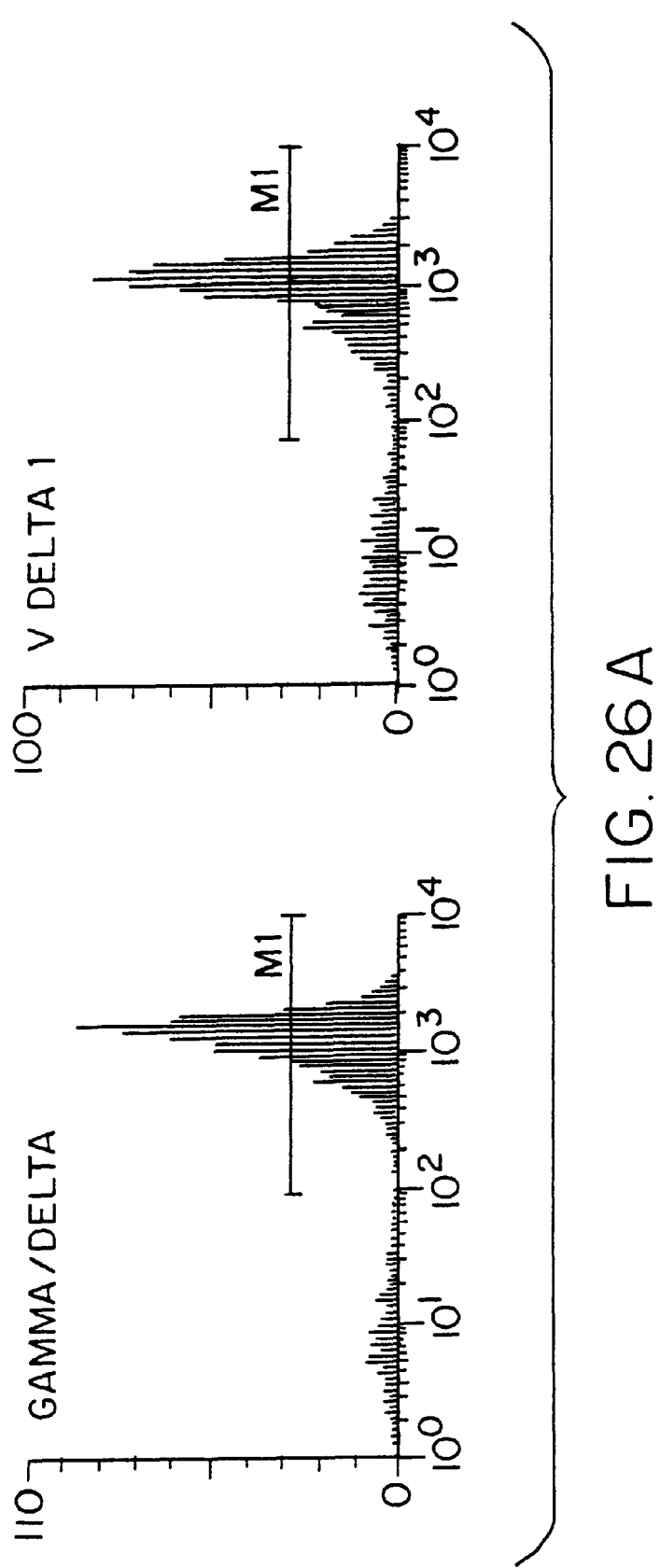
Figure 26B:
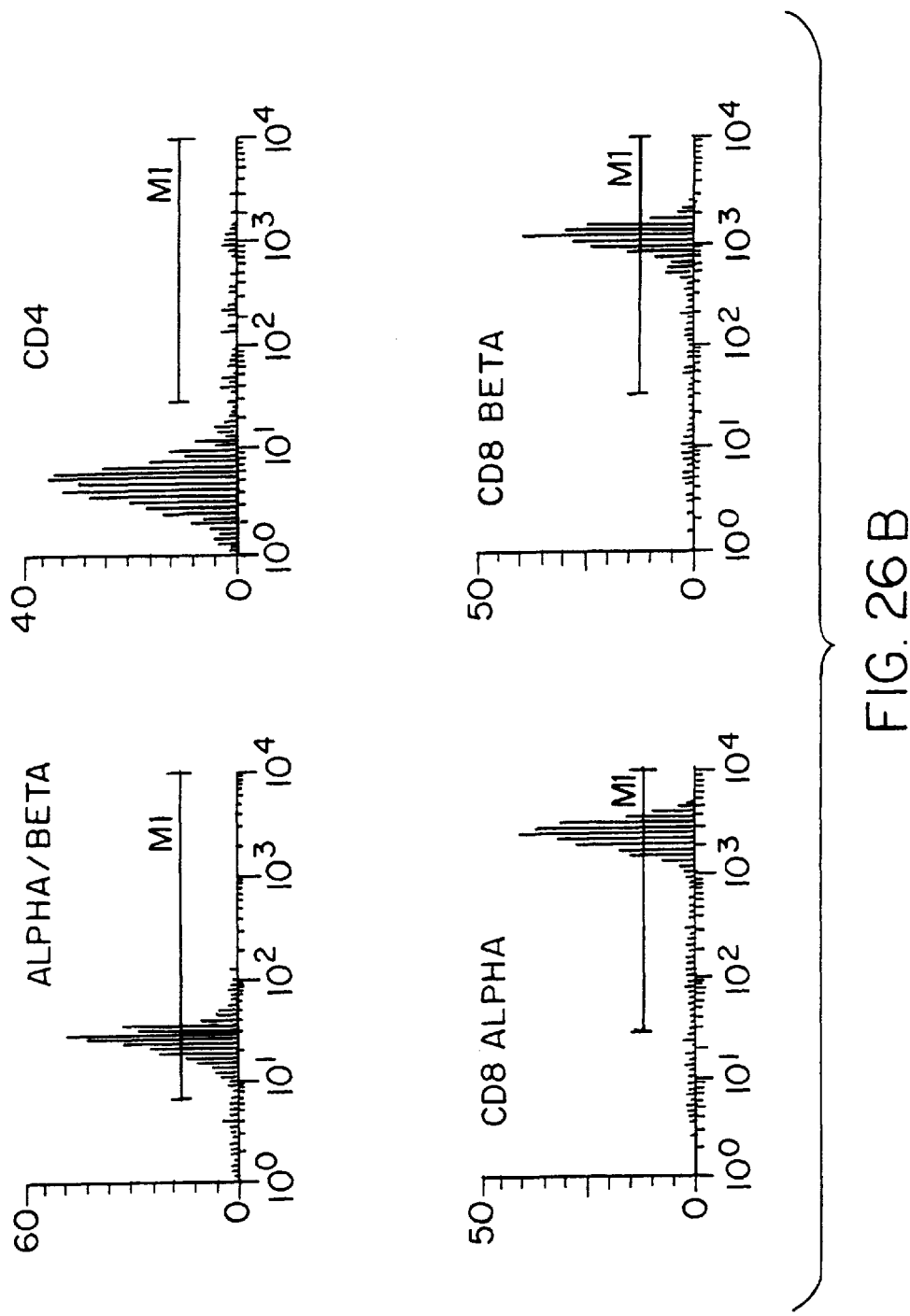

FIGS. 26A–B shows data for the flow cytometric analysis of OGD1 and OAB8 T-cell lines. OGD1 T-cells were stained with biotin-conjugated anti-γδ TCR monoclonal antibody TCRδ1 or anti-Vδ1 monoclonal antibody δTCS1 (revealed with PE-streptavidin), (FIG. 26A). OAB8 T-cells were labelled with anti-αβ TCR monoclonal antibody BMA031 (followed by PE-streptavidin), anti-CD4-FITC monoclonal antibody OKT4, anit-CD8-α-chain-FITC monoclonal antibody OKT8 or anti-CD8-β-chain-FITC 2ST8-5H7 (FIG. 26B).

Figure 27:
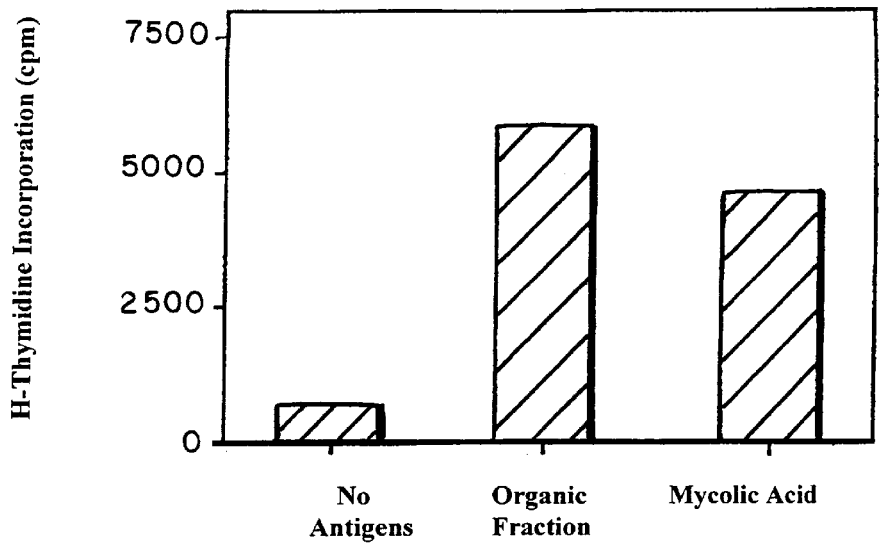

FIG. 27 shows data indicating that the TCRγδ+ T-cell line OGD1 responds to Mycobacterial antigens which partition in the organic phase of a chloroform/methanol extraction. For the organic fraction, whole PBS sonicates of *Mycobacteria tuberculosis* (DIFCO, Detroit, Mich.) (200 mg bacteria/5 ml PBS) were extracted (4:1, v/v organic to aqueous) with chloroform:methanol (2:1, v/v). Cord factor was obtained from SIGMA chemicals (St. Louis, Mo.). To prepare free mycolic acid, cord factor was saponified (25% KOH in methanol: $H_2O$ 1:1, 121° C., 1 hr.) and mycolic acids extracted into hexane. Preparations were dried with $NO_2$ and resuspended in media/fetal calf serum and tested at different dilutions in standard proliferation assay (50,000 activated monocytes with 50000 T-cells in a 3 day assay).

Figure 28:
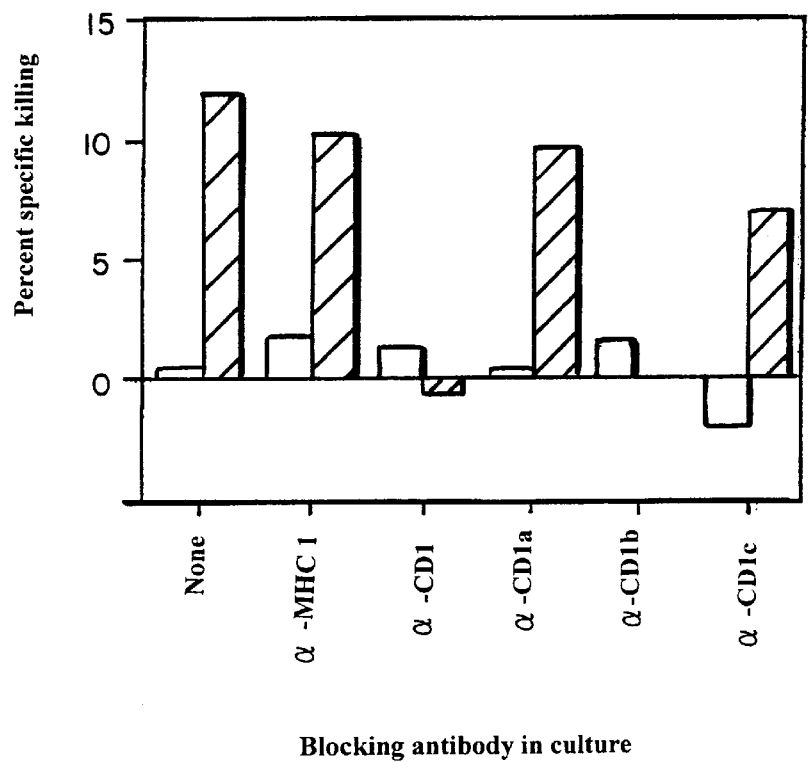

FIG. 28 shows data indicating that the TCRγδ+ T-cell line OGD1 is restricted by CD1b, as demonstrated by cytotoxic assays of the TCRγδ+ T-cell line on antigen pulsed activated monocytes. To prepare target cells, the monocytes were incubated overnight with no antigen (open boxes) or the organic fraction (filled boxes). Target cells were then labelled with $^{51}$Cr and T-cells were added to the target cells at a ratio of 10:1 with different blocking antibody (no monoclonal antibodies, anti-MHC I (BB7.7)), mixture of all anti-CD1 monoclonal antibodies, anti-CD1a (OKT6), anti-CD1b (WM25) or anti-CD1c (10C3)). The measurement of the cytotoxicity was calculated as in standard cytotoxic assays, i.e., specific cytolysis=(Experimental-Spontaneous)/(Maximum-Spontaneous)×100.

Figure 29:
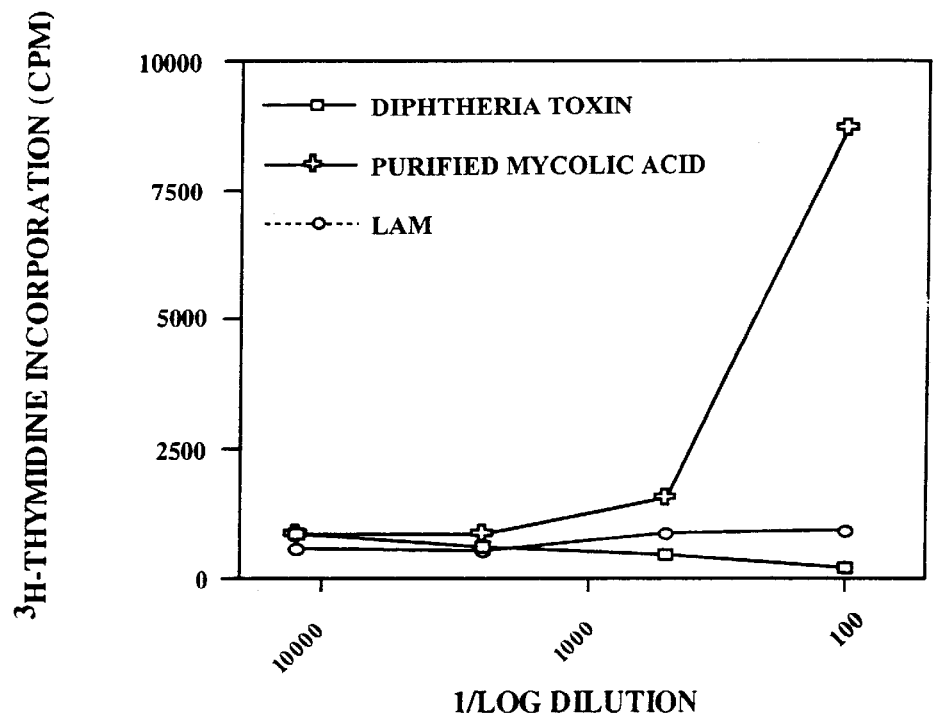

FIG. 29 shows data indicating that the CD8+ αβ+ T-cell line OAB8 responds to Mycobacterial mycolic acid. Mycolic acid was purified by HPLC from M. tb. (prepared as described in Example 4) and used at 1 μg/ml. Control antigens are Diphtheria toxoid (available from Dr. R. Finberg, Dana Farber Cancer Institute, Boston, used at 10 μg/ml) and M. tb. LAM (as in Example 8; 1 μg/ml). Fractions were resuspended in media/fetal calf serum and tested as described in FIG. 27.

Figure 30:
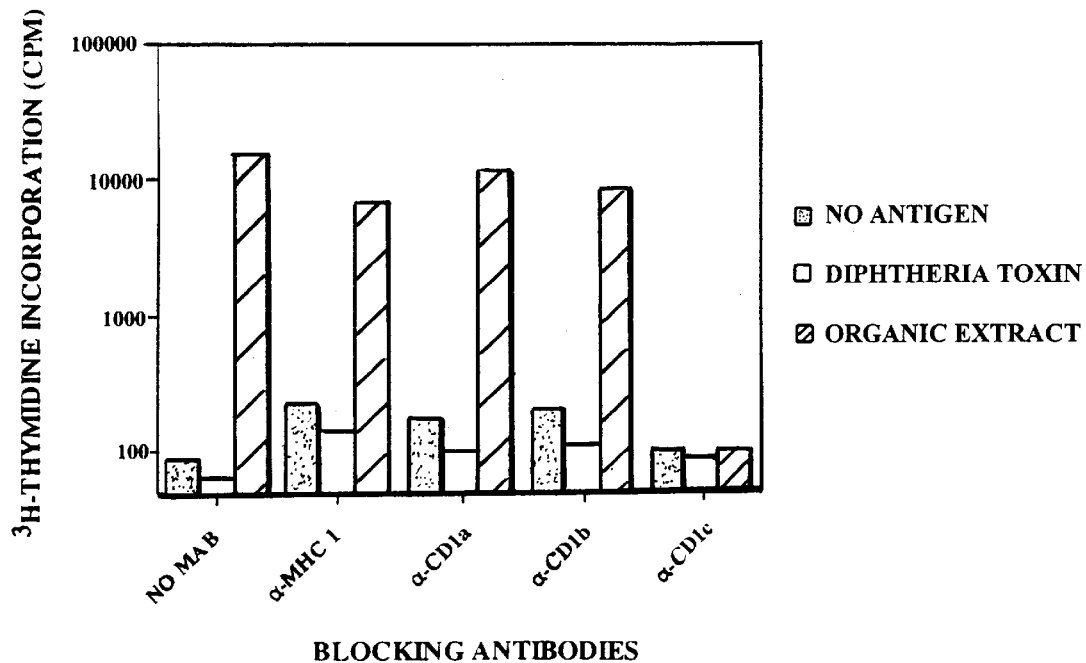

FIG. 30 shows data indicating that the CD8+ αβ+ T-cell line OAB8 is restricted by CD1c, as demonstrated by proliferation assays performed as in FIG. 27. Monoclonal antibodies were added to the culture at a 1/200 final dilution of ascites. Antigens are as described in FIG. 29 and antibodies are the same as in FIG. 28.

DESCRIPTION OF THE PREFERRED EMBODIMENTS

Glossary

Antigen: A molecule, compound or composition of matter which (1) induces an immune response in an animal, alone or in combination with an adjuvant; and (2) interacts specifically with one or more antigen-recognizing components of the animal's immune system.

Foreign antigen: An antigen which is not endogenous to a normal, healthy animal.

Autoimmune antigen: An endogenous molecule, compound or composition of matter in an animal which comprises an antigen in an autoimmune disease. This term is synonymous with "self antigen" and "autoantigen."

CD1-presented antigen: An antigen which is bound by a member of the CD1 family of proteins and displayed on the surface of an CD1$^+$ APC. CD1-presented antigens vary in their size and composition depending on their origin and the member of CD1 family that they are recognized by. As used herein, the term "CD1-presented antigen" includes those antigens identified herein and/or those antigens isolated using the known procedures or those disclosed herein. This term is synonymous with "CD1-restricted antigen." "CD1-bound antigen" designates a CD1-presented antigen that is bound to its appropriate CD1 molecule.

Hydrophobic antigen refers to any hydrophobic molecule or composition, containing amino acids, sugars or lipids, or any combination thereof, which contains some hydrophobic portion.

CD1 family of proteins: A collection of proteins which have been identified by their structure, immunologic cross-reactivity and/or distribution, as being related to known CD1 molecules. A specific CD1 protein may be referred to as a member of the CD1 family of proteins. Members of the CD1 family of proteins include, but are not limited to, CD1a, CD1b, CD1c, CD1d and CD1e (see, Porcelli, S., et al., *Immun. Rev.* 120:137–183 (1991)).

CD1 positive cell: A cell which expresses and displays one or more members of the CD1 family of proteins. This term is synonymous with "CD1$^+$ cell." One skilled in the art can use the procedures described herein, or known in the art, for determining whether a cell is expressing one or more members of the CD1 family of proteins (see Example 1 and Porcelli, S., *Immun. Rev.* 120:137–183 (1991)).

Antigen-presenting cell (APC): An APC includes any cell which displays antigen molecules on its surface via protein carriers and which presents antigen to T-cells. Antigen-binding protein carriers include MHC class I molecules, MHC class II molecules and CD1 molecules; corresponding APCs are designated MHC I$^+$ APCs, MHC II$^+$ APCs and CD1$^+$ APCs.

CD1-restricted T-cell: A mature TCR positive (TCR$^+$) T-cell which can recognize a CD1-bound CD1-presented antigen. CD1-restricted T-cells include any subset of T-cells which interact with a CD1-bound CD1-presented antigen.

CD4$^-$8$^-$ T-cell: A mature TCR$^+$ T-cell which does not express CD4 and CD8. This term is synonymous with "double negative T-cell" and "DN T-cell." Techniques for identifying CD4$^-$8$^-$ T-cells are well known in the art and can readily be employed in the present invention, for example using flow cytometry as described in Example 1, and/or in Panchomoorthy, G., et al., *J. Immuno.* 147:3360–3369 (1991)). Using such procedures, three CD4$^-$8$^-$ T-cell lines, designated DN1, DN2 and DN6, have been isolated and are described herein.

Adjuvant: A molecule, compound or composition of matter which, when introduced into an animal with an antigen, enhances one or more immune responses to that antigen.

Genetic engineering: This term refers to any human manipulation intended to introduce genetic change.

Sample: Any solution, emulsion, suspension, or extract which can be tested using known procedures, or those disclosed herein. A sample may be, but is not limited to, a soluble extract or an organic extract. Examples 1 and 2 provide various non-limiting types of samples derived from *Mycobacterium tuberculosis*.

Contacting: The process of incubating or placing in proximity one item with another. For example, when a cell is contacted with a sample, the cell is incubated with the sample.

Fractionating: Subjecting a sample to conditions or procedures which separate the components of the sample based on physical or chemical properties such as, but not limited to, size, charge, solubility, or composition. Examples of fractionation procedures include, but are not limited to, selective precipitation, organic extraction, size exclusion dialysis or chromatography, and ion exchange chromatography.

Expressing: The process of producing a product involving transcription of a DNA molecule to generate a corresponding mRNA molecule that is optionally translated into a polypeptide by ribosomes and associated cellular factors.

Displaying: The process of localizing a protein, or a protein:antigen complex, to the outermost surface of a cell where the protein or protein:antigen complex is accessible to a second cell or to molecules displayed by a second cell. A protein, or a protein-antigen complex, is said to be displayed by a cell when it is present on the outermost surface of the cell and is thus accessible to a second cell and/or to molecules displayed by a second cell.

Processing of antigen: The process by which an antigen is treated by cellular factors in order to be made competent for displaying.

CD1 blocking agent: A composition or compound which is capable of blocking the interaction of a CD1-presented antigen with CD1, or of blocking the interaction between CD1:antigen complexes and their cognate T-cell receptors. Blocking agents include (1) agents which bind to CD1, (2) agents which bind to a CD1-presented antigen, (3) agents which bind to a CD1:antigen complex, (4) agents which bind to a T-cell receptor that recognizes a CD1:antigen complex and (5) agents which prevent the processing of a CD1-presented antigen.

The Present Invention

The present invention is based on the unexpected observation that CD1 molecules function to present hydrophobic antigens to T-cells. The invention is further based on the observation that cells can be induced to express CD1, and therefore become competent to present antigens to T-cells. Such presentation can involve contacting the cells with cytokines such as, but not limited to, granulocyte/macrophage colony stimulating factor (GM-CSF) and interleukin-4 (IL-4).

Based on these two observations, the present invention comprises:

- methods for detecting the presence of a CD1-presented hydrophobic antigen in a sample;
- methods for isolating such CD1-presented antigens and the isolated antigens;
- vaccines containing CD1-presented antigens and vaccination methods;
- methods of blocking CD1 antigen presentation;
- methods of identifying and/or isolating CD1 blocking agents and the isolated CD1 blocking agents;
- methods of inducing CD1 expression; and
- T-cells for use in the methods disclosed herein.

In one embodiment, the present invention provides methods for determining whether a sample contains a CD1-presented antigen. In one such method, the presence of a CD1-presented antigen in a sample can be determined by: first, contacting the sample with a CD1 positive cell; second, contacting the cell of the first step with a T-cell; and third, measuring the proliferation of the T-cell.

Methods of characterizing classes of T-cells, and of isolating subpopulations of T-cells, are known. See, e.g., Wysocki, L. J., and Sato, V. L., *Proc. Natl. Acad. Sci. (USA)* 75:2844–2848 (1978); Wasik, M. A., and Morimoto, C., *J. Immunol.* 144:3334–3340 (1990); Harriman, G. R., et al., *J. Immunol.* 145:4206–2414 (1990); Koulova, L., et al., *J. Immunol.* 145:2035–2043 (1990); Steward, M., and Male, D., Chapter 25 in *Immunology,* 2d Ed., Roitt, I., et al., eds., Gower Medical Publishing, London, N.Y., 1989.

Methods of culturing T-cells in vitro, and of immortalizing T-cells via fusion to non-growth restricted cells such as myelomas, are also known. See, e.g., Paul, W. E., et al., *Nature* 294:697–699 (1981); Williams, N., *Nature* 296:605–606 (1982).

Techniques for identifying T-cells subsets that are reactive with CD1 presented antigens are also known in the art and can readily be employed in the present invention, for example using flow cytometry as described in the Examples and/or by known techniques such as those descibed in Panchomoorthy, G., et al., *J. Immuno.* 147:3360–3369 (1991)). The present invention advances these techniques by providing methods for enriching T-cell populations to obtain isolated T-cell clones which are reactive to CD1-presented antigens. For example, a population of T-cells is allowed to divide and a subpopulation of mixed T-cells is isolated based on proliferation in the presence of $CD1^+$ APCs and CD1-presented antigen, or on cytolytic activity against transfected cells expressing CD1 molecules in the presence of a CD1-presented antigen. Using such procedures, non-limiting examples of such CD1 reactive T-cell subsets have been identified, including $CD4^-8^-$ T-cell lines, $CD8^+$ TCR $\alpha\beta^+$ T-cell lines, and TCR $\gamma\delta^+$ T-cell lines.

The present invention further provides methods for inducing CD1 expression on a cell. In one such method, a cell can be induced to express CD1 by contacting the cell with one or more cytokines, as known in the art. The preferred cytokines for CD1 induction are granulocyte/macrophage colony stimulating factor (GM-CSF), GM-CSF in combination with interleukin-4 (IL-4), or interleukin-3 (IL-3). Example 1 discloses that monocytes can be induced to express various members of the CD1 family by contacting the monocyte with 100 units each of GM-CSF and IL-4 for 60 hours in RPMI-1640 supplemented with 10% fetal calf serum. Using the methods and materials disclosed herein, one skilled in the art can readily vary the contacting time, cytokine type, cytokine concentration, and contacting conditions to obtain favorable results so long as the contacting step is sufficient to induce CD1 expression.

Several procedures are known in the art for determining the proliferation of T-cells and can be used in the above methods. One skilled in the art can readily adapt such procedures for use in the present invention. One such procedure, described in Example 1, measures the rate of incorporation of $^3$H-thymidine via liquid scintillation and by methods described in Morita, C. T., et al., *Eur. J. Immunol.* 21:2999–3007 (1991)).

The present invention further provides methods for isolating a CD1-presented antigen from a sample. In one such method, a sample is first fractionated using conventional procedures. The fractions of the sample are then tested for the presence of a CD1-presented antigen as outlined above. Examples 2 and 3 describes fractionation procedures using organic extraction with chloroform:methanol and silicic acid chromatography to fractionate a sample containing an extract of *M. tuberculosis* to purify a CD1-presented antigen.

The present invention further provides methods for isolating a CD1-presented antigen which rely on the specificity of binding of CD1 to a CD1-presented antigen. In one such method, a sample containing a CD1-presented antigen is first contacted with either purified CD1, or a cell which expresses and displays CD1 (a "$CD1^+$ cell"). The resulting antigen:CD1 complex, or antigen:$CD1^+$ cell complex, is then separated from the sample. Using such a procedure, a purified antigen:CD1 complex or antigen:$CD1^+$ cell complex is obtained. To further purify the CD1-presented antigen, either type of complex is treated under appropriate conditions such that the CD1-bound antigen will be released from the CD1 molecule.

The above two isolation methods can be combined by the skilled artisan to derive other methods for isolating CD1-presented antigens. In one such combination, a sample is fractionated, as described above, prior to performing a purification method which relies on the binding of a CD1-presented antigen to CD1.

The present invention further provides CD1-presented antigens which are identified or isolated using known procedures, or those disclosed herein. Unlike MHC-presented antigens, CD1-presented antigens are not limited to polypeptides. One CD1-presented nonpeptide antigen, described in detail in Examples 2–4, is a lipid antigen isolated from *M. tuberculosis* that comprises mycolic acids. Another CD1-presented antigen from *M. tuberculosis,* described in Examples 5 and 6, is a more complex lipid. A CD1-presented antigen from *M. leprae* is lipoarabinomannan (LAM), described in Examples 7–9. CD1-presented antigens are hydrophobic and have use in vaccine formulation and development.

The CD1-presented antigens of the present invention, i.e., those identified or isolated using known procedures, or those disclosed herein, are readily usable as vaccines. A skilled artisan can employ routine formulation procedures in order to formulate an isolated CD1-presented antigen for use as a vaccine. In addition to the CD-1 presented antigen in such vaccines, the vaccine can further comprise at least one additional CD-1 molecule or at least one MHC-I or MHC-II presented antigen. See, e.g., *Remington's Pharmaceutical Sciences,* 18th Ed., Gennaro, A. R., ed., Mack, Easton, 1990; *The Pharmacologist Basis of Therapeutics,* 7th Ed., Gilman, A. G., et al., eds., MacMillian, New York, 1985; *Avery's Drug Treatment: Principles and Practice of Clinical Pharmacology and Therapeutics,* 3rd Edition, ADIS Press, Ltd., Williams and Wilkins, Baltimore, Md. (1987).

The CD1-presented antigens of the present invention can be purified as disclosed herein over a wide range of purities. A skilled artisan will know how to employ various purification strategies in order to obtain a CD1-presented antigen which has been purified to the extent required for an intended use.

The vaccines of the present invention can be formulated using a purified CD1-presented antigen or can be formulated using a CD1-bound antigen. Because CD1-restricted antigens are presented to T-cells as a complex of antigen and CD1, the use of an antigen:CD1 complex can, in some cases, provide superior immunization properties.

The present invention further provides methods for assaying for inhibitors of CD1-restricted antigen presentation to T-cells, i.e., CD1 blocking agents. In one such method, CD1 antigen presentation is inhibited by using a CD1 blocking agent to block the ability of a CD1-restricted antigen to bind to CD1. As used herein, a CD1 blocking agent is said to "inhibit CD1-restricted antigen presentation" when the CD1blocking agent decreases (1) the binding of a CD1-presented antigen to a CD1 molecule or (2) the binding of a CD1:CD1-presented antigen complex to its cognate T-cell receptors. Some CD1 blocking agents are able to block such binding to undetectable levels while other CD1 blocking agents only slightly decrease such binding. CD1 blocking agents include, but are not limited to, (1) agents which bind to CD1, (2) agents which bind to the CD1-presented antigen, (3) agents which bind to the CD1:antigen complex, and (4) agents which bind to the T-cell receptors that recognize the CD1:antigen complex. Respective examples of blocking agents include, but are not limited to, (1) polyclonal or monoclonal antibodies which bind to and block the portion of a CD1 molecule that binds a CD1-presented antigen, (2) polyclonal or monoclonal antibodies which bind to and block the portion of a CD1-presented antigen that binds CD1, (3) synthetic oligopeptides that are derived from the CD1:antigen-binding portion of a T-cell receptor and which bind to and block the portion of the CD1:antigen complex bound by intact T-cell receptors, and (4) synthetic compounds comprising a CD1-presented antigen chemically linked to a purified CD1 molecule or a synthetic derivative thereof.

In an alternative method for inhibiting antigen presentation of CD1-restricted antigens, a CD1 blocking agent can be employed which blocks the interaction of the antigen:CD1 complex with the TCR molecules on the T-cell. By inhibiting the presentation step, the activation of specific subsets of T-cells can be inhibited.

Pilot trials are currently underway of treatment of humans suffering from an autoimmune disease with peptides derived from TCR molecules. Oksenberg, J. R., et al., *J. Neurol. Sci.* 115 (Suppl.):S29–S37 (1993).

DNA molecules encoding TCR polypeptides displayed by T-cells that recognize the CD1-presented antigens of the invention are isolated according to methods known in the art. Oskenberg, J. R., et al., *Proc. Natl. Acad. Sci.* (*USA*) 86:988–992 (1989); Oksenberg, J. R., et al., *Nature* 345:344–346 (1990) and erratum, *Nature* 353:94 (1991); Uematsu, Y., et al., *Proc. Natl. Acad. Sci.* (*USA*) 88:534–538 (1991); Panzara, M. A., et al., *Biotechniques* 12:728–735 (1992); Uematsu, Y., *Immunogenet.* 34:174–178 (1991).

The DNA sequence is converted into a polypeptide sequence, and the portion of the polypeptide sequence that corresponds to the antigen-binding variable region of a TCR polypeptide is used to design synthetic oligopeptides that bind CD1:antigen complexes on APCs, thereby inhibiting antigen presentation.

Oligopeptides are chemically synthesized according to standard methods (Stewart and Young, *Solid Phase Peptide Synthesis,* Pierce Chemical Co., Rockland, Ill., 1985) and purified from reaction mixtures by reversed phase high pressure liquid chromatography (HPLC).

Additionally or alternatively, methods for generating anti-TCR antibodies and anti-TCR binding peptides are well known in the art with regard to MHC presentation and can readily be adapted to the herein disclosed CD1 presentation system. Strominger, J. L., *Cell* 57:895–898 (1989); Davis, M. M., and Bjorkman, P. J., *Nature* 334:395–404 (1989).

A skilled artisan can readily employ known methods of antibody generation, as well as rational blocking agent design in order to obtain the blocking agents of the present invention. Harlow, E., and Lane, D., *Antibodies: A Laboratory Manual,* Cold Spring Harbor Press, Cold Spring Harbor, 1988; *Synthetic Peptides: Answers Guide,* Freeman, W. H., New York, 1991; Kasprzak, A. A., *Biochemistry* 28:9230–9238 (1989). Additionally or alternatively, libraries of molecularly diverse molecules can be screened for individual member molecules which are CD1 blocking agents. Effective CD1 blocking agents are identified by their ability to inhibit CD1-mediated T-cell proliferative and/or cytolytic responses using the materials and methods described herein.

The embodiments of the invention described above can be used for the indicated purposes, alone or in combination with each other or other complementary methods and/or compositions.

The manner and method of carrying out the present invention may be more fully understood by those of skill by reference to the following examples, which examples are not intended in any matter to limit the scope of the present invention or of the claims directed thereto.

EXAMPLE 1

Antigen Presentation by CD1b

Methods

Flow cytometry was performed as described previously (Panchamoorthy, G., et al., *J. Immunology* 147:3360–3369 (1991)) using the following monoclonal antibodies (mAbs): P3 (IgG1 control; Panchamoorthy, G., et al., *J. Immunology* 147:3360–3369 (1991)), OKT6 (anti-CD1a; Reinherz, E., et al., *Proc. Natl. Acad. Sci.* (*USA*) 77:1588–1592 (1980)), 4A7.6 (anti-CD1b; Olive, D., et al., *Immunogenetics* 20:253–264 (1984)), 10C3 (anti-CD1c; Martin, L. H., et al., *Proc. Natl. Acad. Sci.* (*USA*) 84:9189–9193 (1987)), W6/32 (anti-HLA-A,B,C; Brodsky, F. M., and Parham, P. P., *J. Immunology* 128:129–135 (1982)), BMA031 (anti-$\alpha$:$\beta$ TCR; Lanier, L. L., et al., in *Leukocyte Typing III,* McMichael, A. J., ed., pp. 175–178, Oxford University Press, 1987), OKT4 (anti-CD4; Reinherz, E., et al., *Proc. Natl. Acad. Sci.* (*USA*) 77:1588–1592 (1980)), OKT8 (anti-CD8$\alpha$; Reinherz, E., et al., *Proc. Natl. Acad. Sci.* (*USA*) 77:1588–1592 (1980)) and 2ST8-5H7 (anti-CD8$\beta$; Shiue, L., et al., *J. Exp. Med.* 168:1993–2005 (1988)).

Monocytes were isolated from leukocyte concentrates of normal donors by plastic adherence (Anegon, I., et al., *J. Immunology* 147:3973–3980 (1991)), and detached by incubation at 37° C. in phosphate buffered saline (PBS) with 0.53 mM EDTA (PBS/EDTA). Adherent-cells were typically >90% $CD14^+$ and MHC class $II^+$, and negative for CD1a, CD1b and CD1c as determined by surface staining (data not shown). To induce CD1 expression, monocytes were cultured for 60 hours in RPMI-1640 (Gibco) containing 10% fetal calf serum (FCS, Hyclone) with 100 Units/ml each of GM-CSF and IL-4 (Genetics Research Institute). Cells were harvested using PBS/EDTA as above.

T-cell line DN1 was established from a random normal donor's peripheral blood. Nonadherent mononuclear cells were treated with mAbs OKT4 and OKT8 and rabbit complement, and the remaining viable cells were suspended in a mixture of OKT4 (anti-CD4), OKT8 (anti-CD8$\alpha$) and anti-TCR$\delta$1 (Porcelli, S., et al., *Immun. Rev.* 120:137–183 (1991)) mAbs for 1 hour, washed and incubated for 30 minutes at 4° C. with goat anti-mouse immunoglobulin coupled magnetic beads (Dynal). After magnetic separation and removal of $CD4^+$ and/or $CD8^+$ and/or $\delta$-TCR cells, the remaining $CD4^{31}$ $8^-$ $\alpha$:$\beta$ $TCR^+$ cells were cultured with equal numbers of autologous monocytes in complete medium (RPM-1640 with 10% FCS and additional supplements as previously described by Morita, C. T., et al. (*Eur. J. Immun.* 21:2999–3007 (1991)) with 100 U/ml each of GM-CSF and IL-4. *M. tuberculosis* soluble extract, produced by sonication of desiccated bacilli (strain H37Ra (Difco)) in PBS followed by centrifugation at 100,000 g to clarify (i.e., to remove insoluble material from) the sonicates, was added to a bacterial protein concentration of 10 $\mu$g/ml. More soluble antigenic (i.e., T-cell proliferative) activity is obtained from soluble aqueous sonicates of M. tb. by adding detergents such as CHAPS or octylglucoside during the sonication step; without addition of detergent, 90 to 95% of antigenic activity is lost during post-sonification clarification. Cultures were restimulated every 10 to 14 days with *M. tuberculosis* and heterologous CD1$^+$ monocytes (induced to express CD1 as described above) in complete medium, and were fed every three to four days with fresh medium containing 1 nM recombinant interleukin-2 (IL-2).

T-cell proliferation response assays were carried out in triplicate with 5×10$^4$ each of T-cells and irradiated (5,000 Rad) APCs in 200 µl complete medium in 96 well flat bottom microtiter plates (Linbro). *M. leprae* and *Escherichia coli* soluble extracts were produced as described for *M. tuberculosis*. Monoclonal antibodies were added as purified immunoglobulin to a final concentration of 25 µg/ml. Cultures were harvested on day five (day three for mAb blocking) after a six hour pulse with 1 µCi $^3$H-thymidine (6.7 Ci/mmol, New England Nuclear), and $^3$H incorporation determined by liquid scintillation counting. Results are expressed as the mean counts per minute (CPM) of $^3$H-thymidine incorporation of triplicate cultures. Isolated monocytes or whole peripheral blood mononuclear cells (PBMCs) were treated with recombinant GM-CSF and IL-4 as above, or with IFNγ 100 U/ml for 60 hours prior to combining them with T-cells for proliferation assays. T-cell clone DN1.C7 is representative of four extensively characterized subclones derived from DN1 by phytohemagglutinin (PHA) stimulation in limiting dilution culture and propagated using PHA stimulation and IL-2 as previously described. Morita, C. T., et al., *Eur. J. Immun.* 21:2999–3007 (1991). All clones derived from line DN1 had a surface phenotype indistinguishable from that shown in FIG.. 1*b*, i.e., α:β TCR expression, non-expression of CD4, and minimal or non-expression of CD8.

T-cell cytolytic response assays were carried out as follows. Methods of transfecting C1R cells and assaying specific cytolytic activity by $^{51}$Cr release have been described. Balk, S. P., et al., *Science* 253:1411–1415 (1991) and Morita, C. T., et al., *Eur. J. Immun.* 21:2999–3007 (1991), respectively. BK6, an α:β TCR cytotoxic T-cell clone that lyses cells displaying CD1a, was isolated from the blood of a patient with SLE as previously described (Porcelli, S., et al., *Nature* 341:447–450 (1989)), and clone 3C8, an α:β TCR cytotoxic T-cell clone that lyses cells displaying CD1c, was isolated from the blood of a normal donor using the same method. Transfected cells were labeled with $^{51}$Cr and used as target-cells in cytolytic assays with an effector (T-cell) to target (transfectant) ratio of about 50:1. Methods of assaying $^{51}$Cr release and calculating the % specific lysis have been described. Brenner, M. B., et al., *Nature* 325:689–694 (1987).

Stable transfectants of T2 cells were prepared using the method described for C1R cells. Balk, S. P., et al., *Science* 253:1411–1415 (1991). APCs for glutaraldehyde fixation and chloroquine experiments were GM-CSF- and IL-4treated PBMCs as described above, and glutaraldehyde fixation and chloroquine treatment of APCs were performed according to published methods. Chesnut, R. W., et al., *J. Immun.* 129:2382–2388 (1982); Roncarolo, M. G., et al., *J. Immunol.* 147:781–787 (1991). CD4$^+$ T-cell line DG.1 was derived from an HLA-DR7$^+$ rheumatoid arthritis patient by repeated stimulation of synovial fluid lymphocytes with autologous EBV-transformed B-cells and *M. tuberculosis* purified protein derivative (PPD, Statens Serum Institute; data not shown). Proliferative response assays were performed as above, except that 2×10$^5$ APCs were added per well and $^3$H-thymidine incorporation was determined after three days.

Results

Figure 1E:
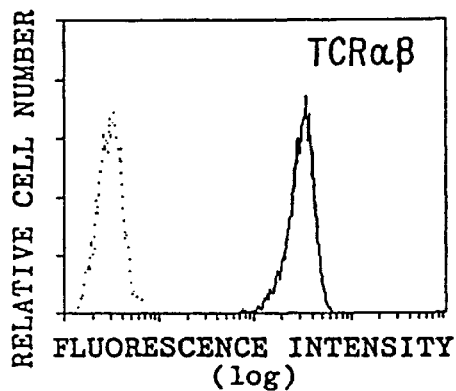
Figure 1F:
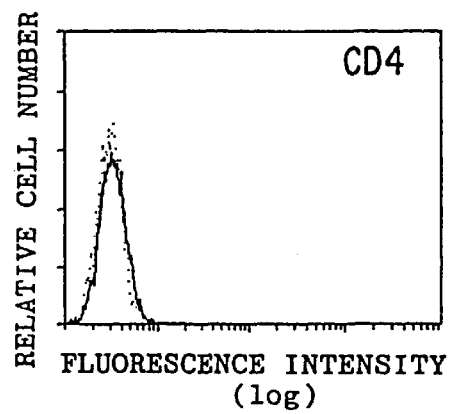
Figure 1G:
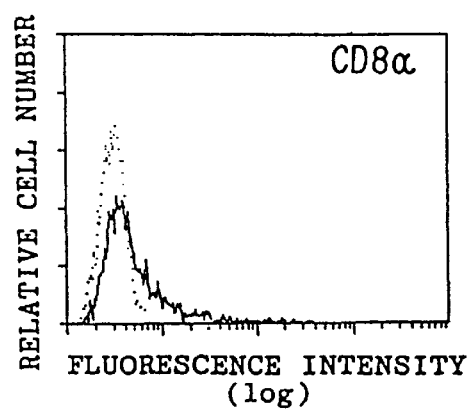
Figure 1H:
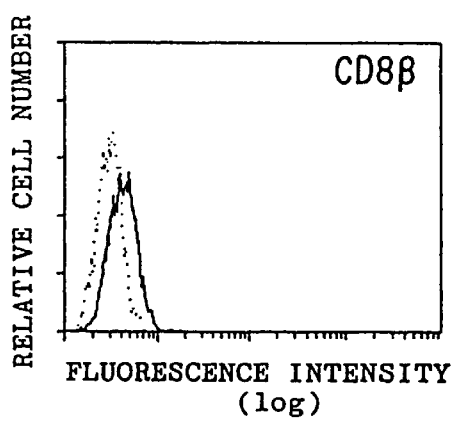

In order to develop a system to detect antigen presentation by CD1 molecules, the ability of various recombinant cytokines to induce expression of CD1a, CD1b and CD1c on peripheral blood monocytes, which normally do not express significant levels of these molecules, was assessed. *Leukocyte Typing IV,* Knapp, W., ed., Oxford University Press, Oxford, U.K., pp. 251–269, 1989. High levels of CD1a, CD1b and CD1c were consistently observed on monocytes cultured with a combination of granulocyte/monocyte colony stimulating factor (GM-CSF) and interleukin-4 (IL-4) (FIG. 1*a*). Alternatively, GM-CSF may be used alone, although the resultant level of CD1 expression is somewhat less than that resulting from combined GM-CSF and IL-4 treatment. Interleukin-3 (IL-3) may also be used, alone or in combination with other cytokines. Monocytes cultured in the absence of cytokines, or those cultured with interferon-γ, did not express significant levels of C1Da, CD1b, or CD1c (data not shown).

Because monocytes are efficient antigen presenting cells (APCs), we reasoned that CD1$^+$ monocytes might stimulate a CD1 restricted T-cell response to an exogenous antigen. Because most CD1 specific T-cells identified to date have a double negative (DN; CD4$^-$8$^-$) phenotype (Porcelli, S., et al., *Nature* 341:447–450 (1989); Faure, F., et al., *Eur. J. Immun.* 20:703–706 (1990)), we focused on this subset of cells and generated a T-cell line by repeated stimulation of peripheral blood of α:β TCR$^+$ CD4$^-$8$^-$ T-cells with a soluble extract of *M. tuberculosis* and heterologous CD1$^+$ monocytes (FIG. 1*b*).

Figure 2A:
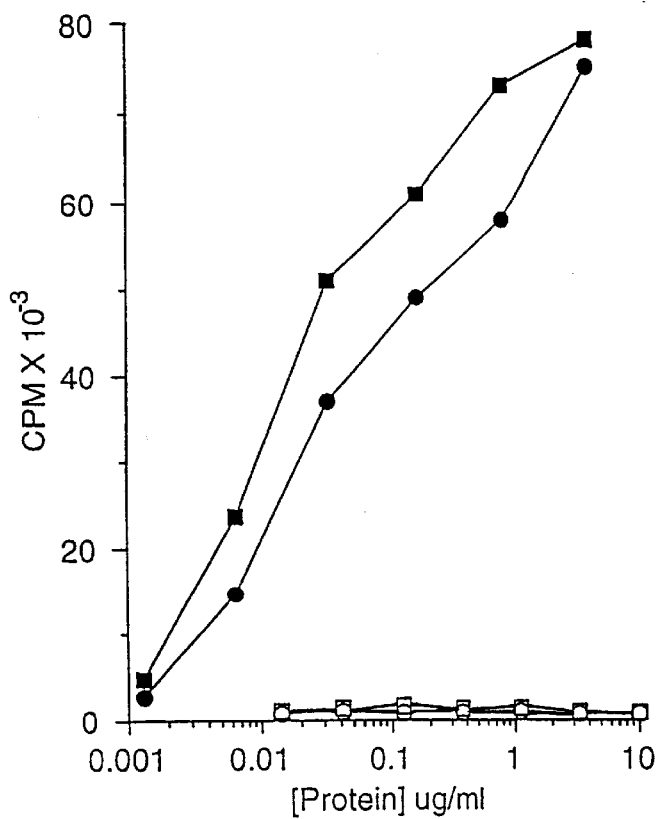
FIGS. 2A–E show data for antigen specificity and self restriction of proliferative responses of CD4⁻8⁻ T-cell line DN1 and its subclone DN1.C7.
Figure 2B:
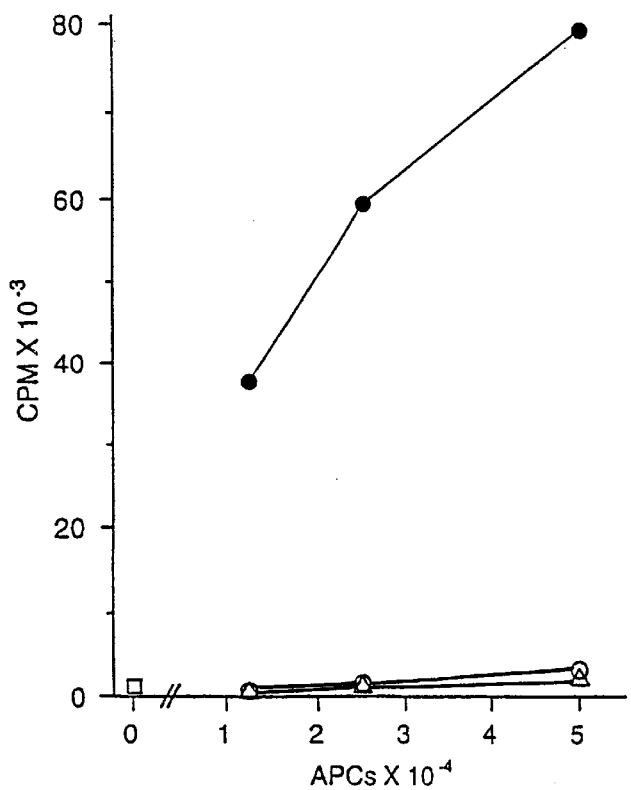
Figure 2C:
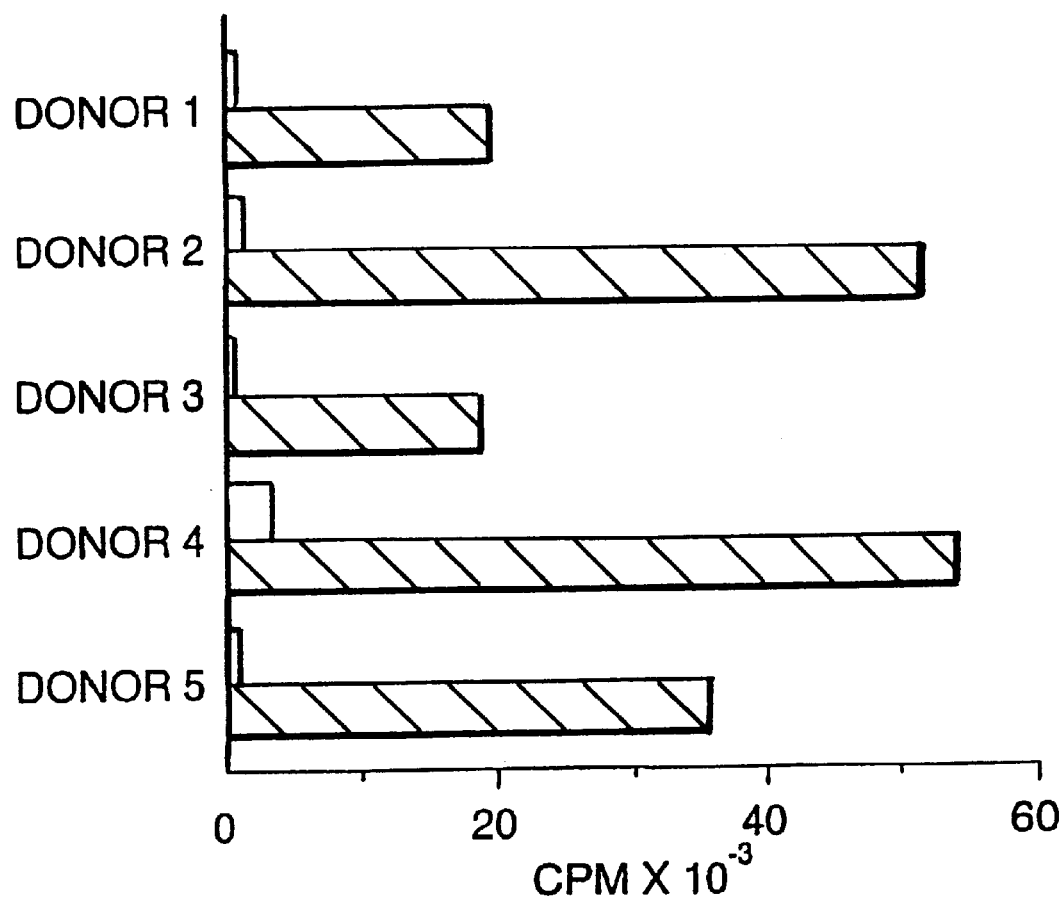
Figure 2E:
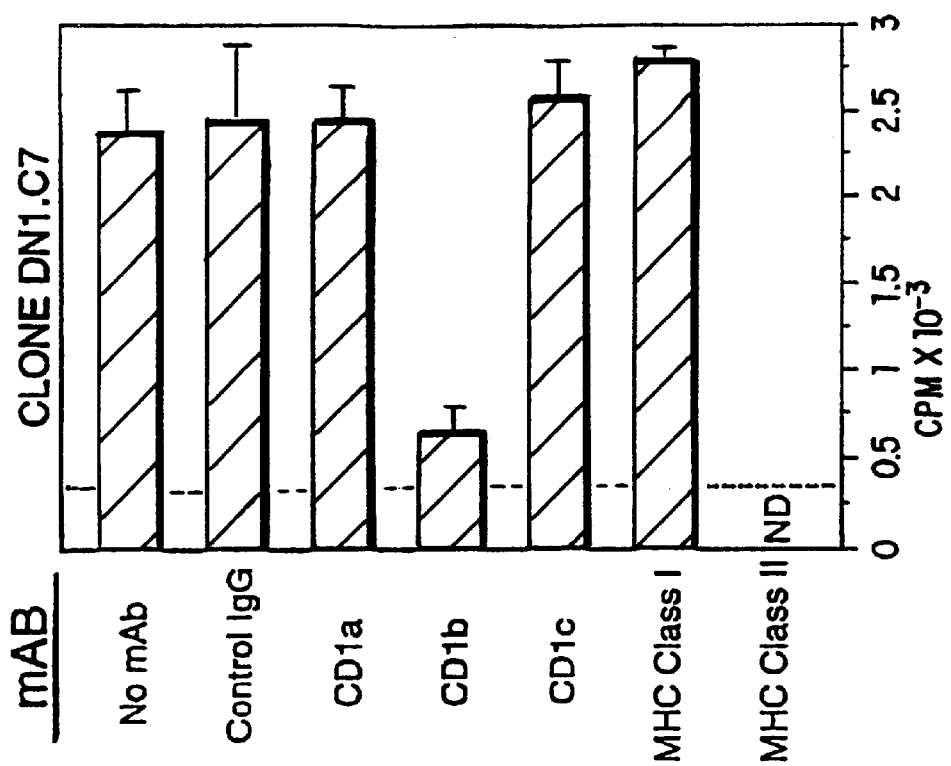
Figure 2D:
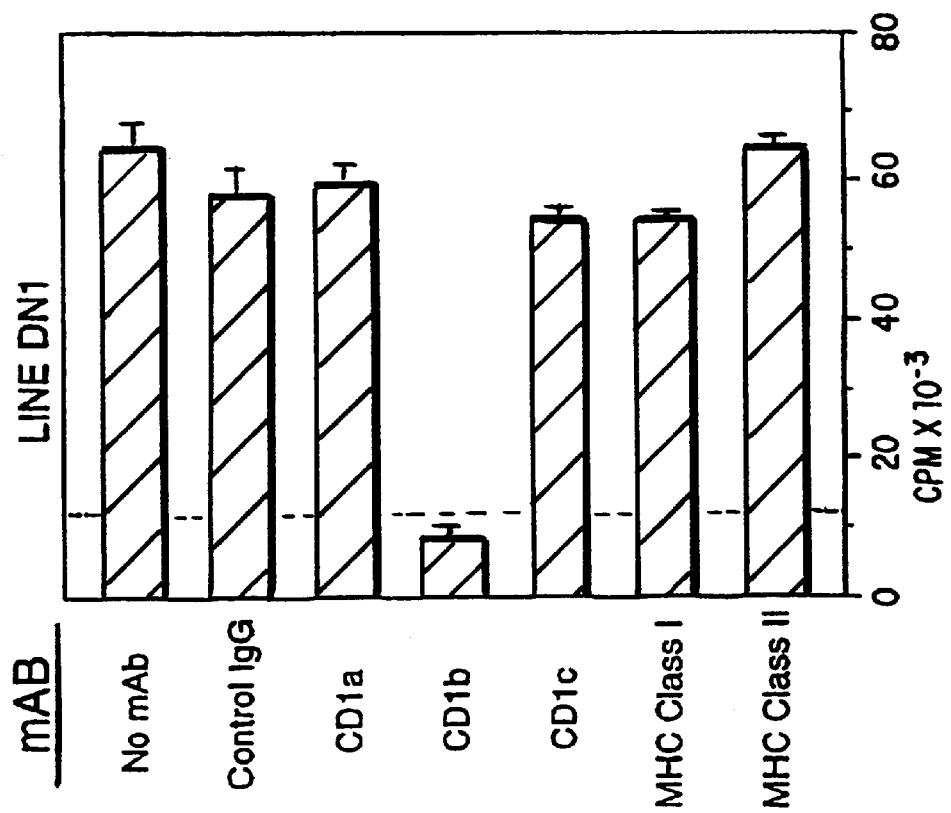
Figure 3:
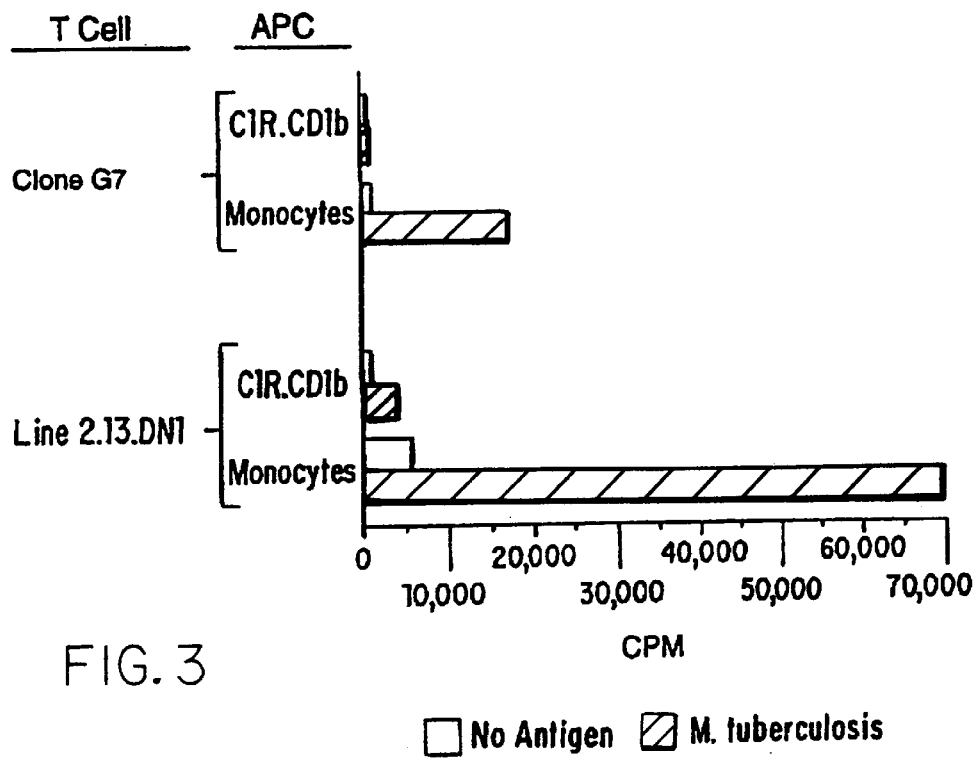
FIG. 3 show data for a comparison of the ability of antigen presenting cell lines CR1 and cytokine stimulated monocytes to stimulate growth of T-cell lines 2.13.DN1 and G7, clones derived from T-cell line DN1. Open bars, T-cells plus APCs without *M. tuberculosis*; solid bars, T-cells plus APCs with *M. tuberculosis* (1 μg protein/ml).

Functional studies of the resulting T-cell line (designated DN1) showed that these T-cells gave specific proliferative responses to antigens derived from *M. tuberculosis* and from closely related *M. leprae* bacilli, but not to unrelated bacterial antigens such as those from *E. coli* or tetanus toxoid (FIG. 2*a*). These responses were dependent on the monocytes being pretreated with GM-CSF and IL-4 (FIG. 2*b*), and were not restricted by polymorphic MHC determinants (FIG. 2*c*). This lack of MHC restriction was consistent with antigen presentation restriction by non-MHC molecules. In order to determine if CD1 molecules are required for *M. tuberculosis* antigen presentation, the effects of monoclonal antibodies (mAbs) specific for CD1 or MHC molecules on the *M. tuberculosis* induced proliferation of T-cell line DN1 and a representative subclone, DN1.C7, were determined. Only anti-CD1b mAb showed significant blocking of the *M. tuberculosis* induced proliferative response, and no consistent effects were observed with anti-CD1a or CD1c mAbs or with mAbs against monomorphic determinants of MHC class I or class II molecules (FIG. 2*d*).

Figure 4A:
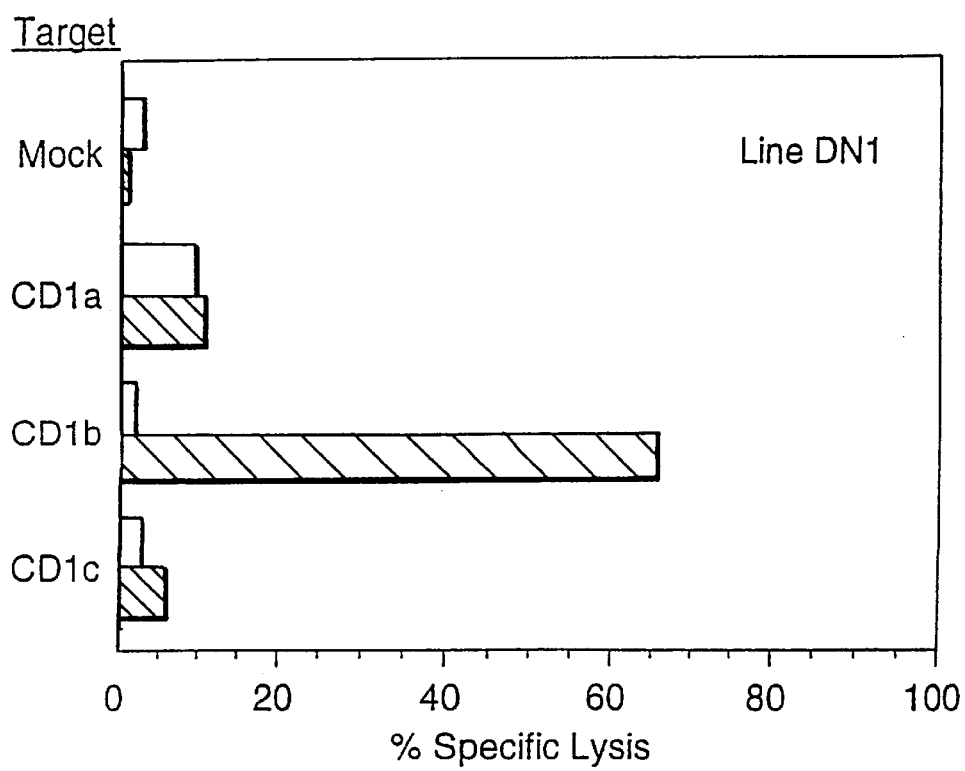
FIGS. 4A–D show data for the presentation of *M. tuberculosis* by CD1 transfectants of the lymphoblastoid cell line C1R. C1R cells stably transfected with vector pSRα-NEO DNA (mock) or with constructs of pSRα-NEO containing cDNAs encoding the indicated CD1 molecule (CD1a, CD1b and CD1c) were cultured for 12 hours in medium alone (open bars) or in medium containing *M. tuberculosis* (25 μg protein/ml, filled bars), labeled with $^{51}$Cr and used as target-cells for cytolytic assay with various effector T-cells. The effector T-cell to target-cell ratio was 50:1.
Figure 4B:
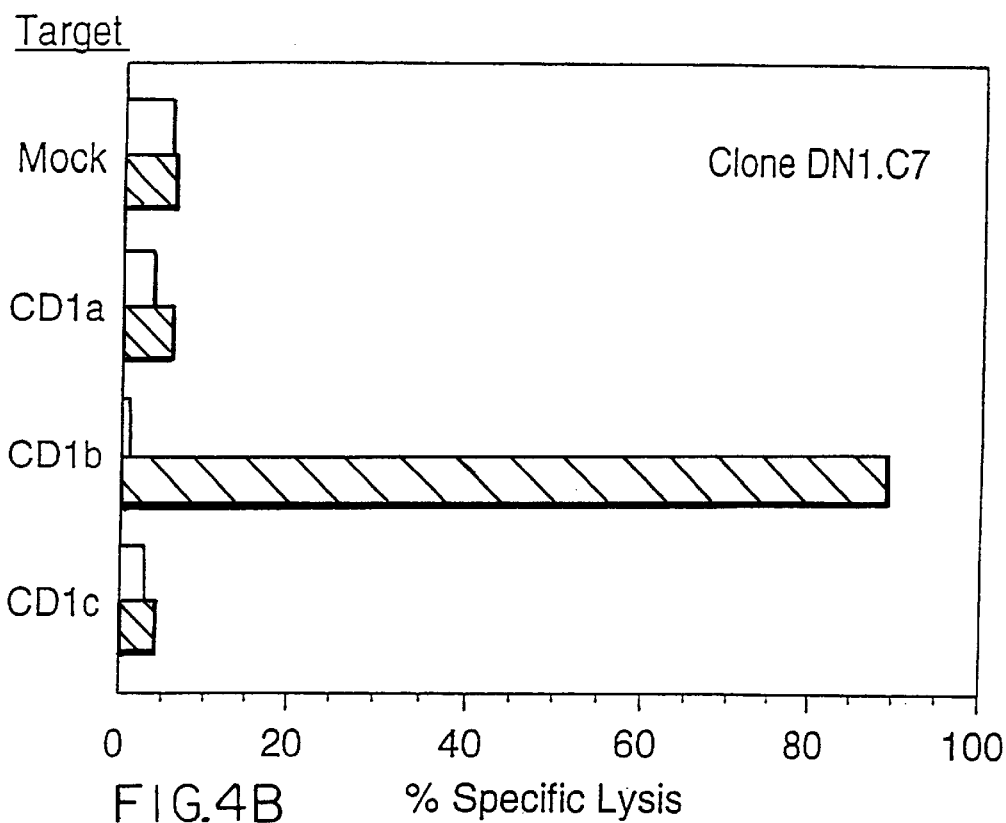
Figure 4C:
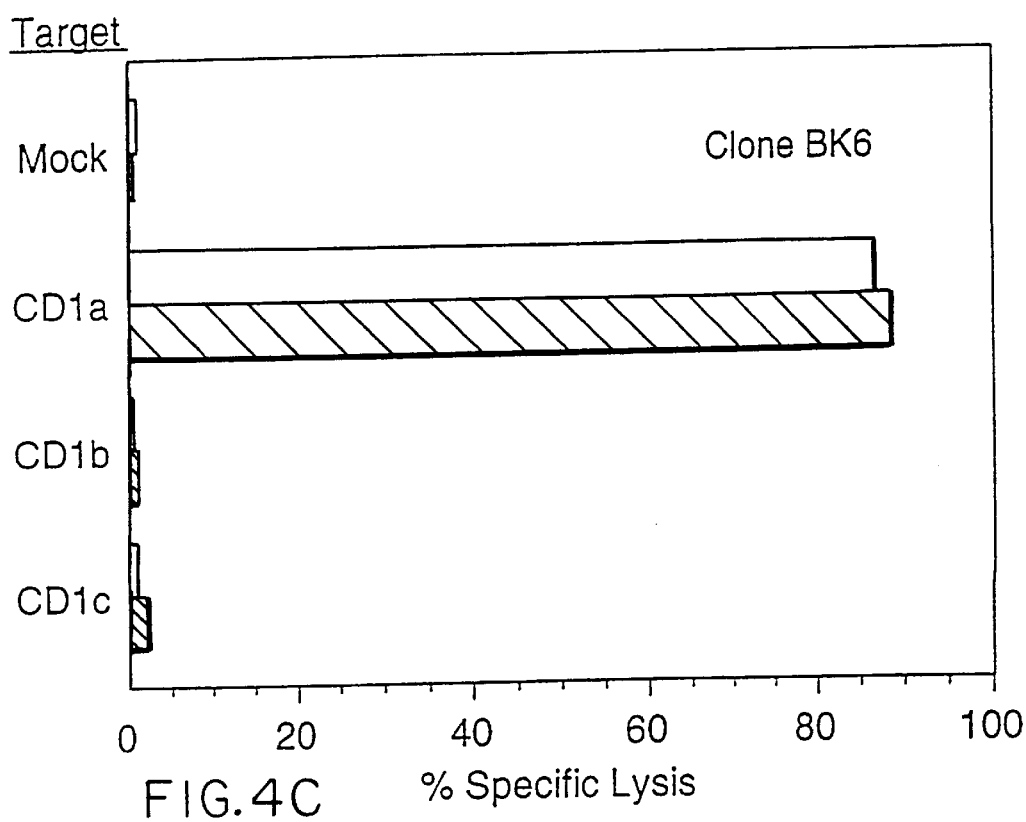
Figure 4D:
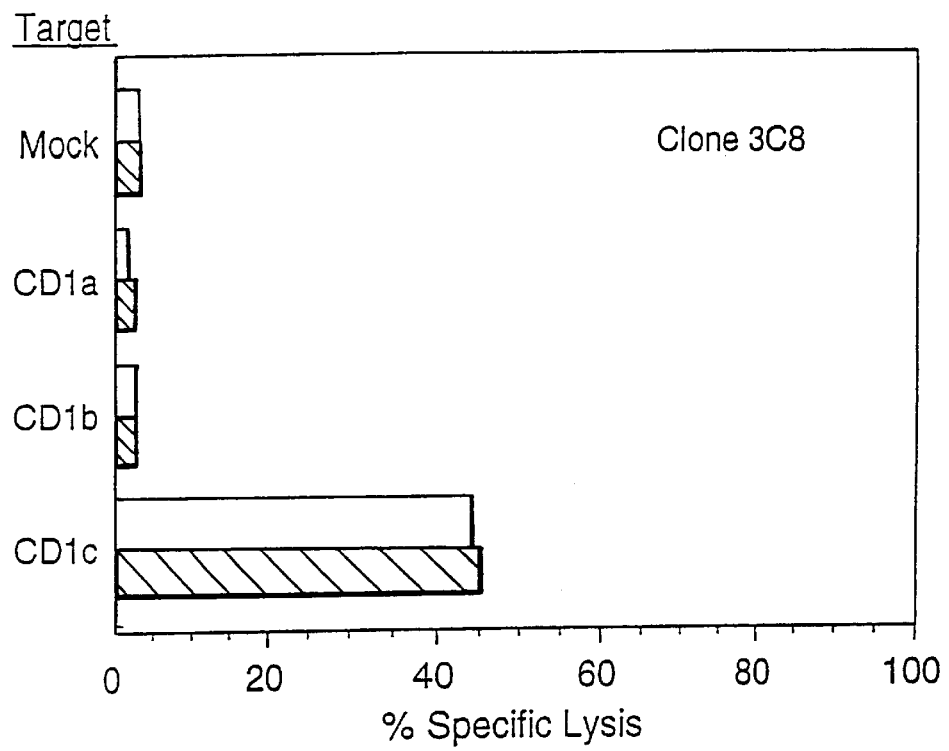

B-cell transfectants are effective targets for α:β TCR CD4$^-$8$^-$ cytolytic T-cell activity. Using the B lymphoblastoid cell line C1R (Zenmour, J., et al., *J. Immun.* 148:1941–1948 (1992)), stable transfectants expressing and displaying CD1a, CD1b or CD1c at comparable levels were generated and tested for their ability to present *M. tuberculosis* in a cytolytic assay. Only C1R cells transfected with DNA sequences encoding CD1b and incubated with *M. tuberculosis* prior to the assay were lysed by α:β TCR DN T-cell line DN1 and its subclone DN1.C7 (FIGS. 4*a* and *b*). The specificity of this CD1b restricted response was confirmed using two control CD4$^-$8$^-$ α:β TCR$^+$ T-cell clones, BK6 and 3C8, which were derived by mitogen stimulation without exposure to *M. tuberculosis* antigens. Previous studies show that BK6 and 3C8 lyse target-cell lines expressing CD1a and CD1c, respectively (data not shown). As for all other CD1 reactive T-cell clones described prior to this disclosure (Porcelli, S., et al., Nature 341:447–450 (1989); Faure, F., et al., Eur. J. Immun. 20:703–706 (1990); Balk, S. P., et al., Science 253:1411–1415 (1991)), these clones appear to be autoreactive and recognize their nonpolymorphic CD1 ligands in the absence of exogenous antigens. As expected, clones BK6 and 3C8 lysed only C1R transfectants expressing CD1a or CD1c respectively, and lysis was not significantly affected by prior incubation of the target-cells with M. tuberculosis (FIGS. 4c and d).

Figure 5A:
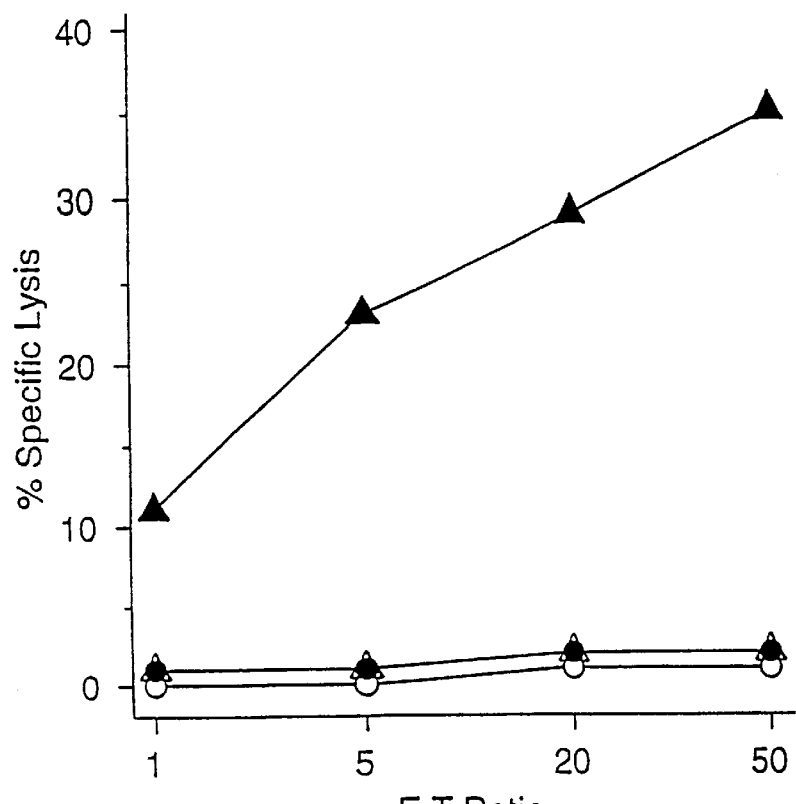
FIGS. 5A–C shows data indicating that CD1b restricted presentation of *M. tuberculosis* antigen does not require MHC Class II region encoded molecules, but does involve antigen processing by a chloroquine sensitive pathway.

The lack of MHC restriction demonstrated by the preceding experiments argued that MHC encoded antigen presenting molecules were not involved in the CD1b restricted presentation of M. tuberculosis antigens to line DN1. As a more stringent test of this hypothesis, CD1b transfectants of the T2 cell line, in which extensive chromosomal deletions in both MHC loci result in a complete lack of MHC class II molecule expression, were produced. Salter, R. D., et al., Immunogenetics 21:235–246 (1985); Erlich, H., et al., Hum. Immun. 16:205–219 (1986). The MHC linked transporter genes TAP-1 and TAP-2 (reviewed in Parham, P., Nature 357:193–194 (1992)) are also deleted from T2, resulting in defective expression and function of MHC class I molecules. Hosken, N. A., and Bevan, M., Science 248:367–370 (1990); Wei, M., and Cresswell, P., Nature 356:443–446 (1992). Nevertheless, transfection of CD1b into T2 led to expression of CD1b on the cell surface at a level similar to that seen on other transfected B-cell lines (data not shown) and generated a target-cell that presented M. tuberculosis to line DN1 (FIG. 5a).

Figure 5B:
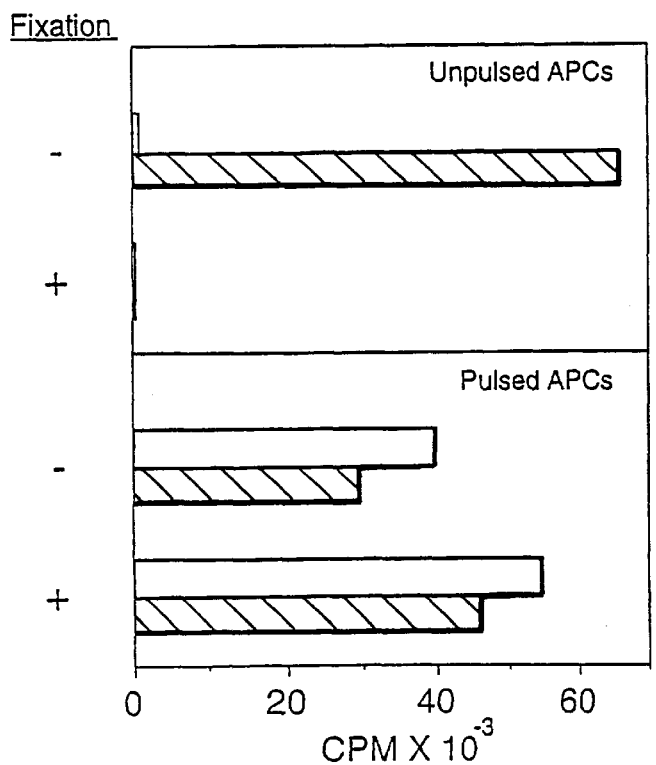
Figure 5C:
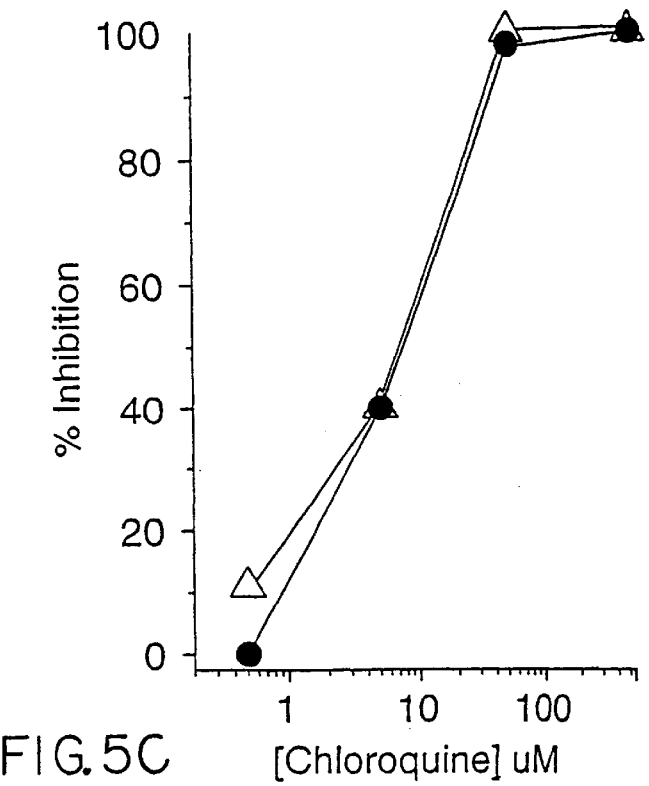

The presentation of exogenous antigens to T-cells generally requires uptake and processing of complex protein antigen molecules by antigen presenting cells, a process which is blocked by aldehyde fixation of the APC surface and by lysosomotropic amines such as chloroquine. Ziegler, H. K., and Unanue, E. R., Proc. Natl. Acad. Sci. USA 79:175–179 (1982); Chesnut, R. W., et al., J. Immun. 129:2382–2388 (1982). By these criteria, CD1b restricted presentation of M. tuberculosis also showed a requirement for antigen uptake and processing. Mild fixation of CD1b$^+$ APCs with glutaraldehyde completely abrogated their ability to stimulate line DN1 in the presence of M. tuberculosis soluble antigens, although the same APCs pulsed with M. tuberculosis prior to fixation retained their ability to stimulate a proliferative response (FIG. 5b). Furthermore, the presentation of M. tuberculosis antigens to line DN1 was strongly inhibited by chloroquine with a dose dependence virtually identical to that for the inhibition of MHC class II mediated presentation of mycobacterial antigens (FIG. 5c), indicating that processing of antigens for CD1b and MHC class II restricted responses may involve similar pathways or organelles, or that the pathways share one or more chloroquine-sensitive cellular factors. Interestingly, T2 cells have recently been shown to be defective in the processing of antigens presented by MHC class II molecules (Riberdy, J. M., and Cresswell, P., J. Immun. 148:2586–2590 (1992)) because T2 cells lack the DMA and DMB genes. Morris, P., et al., Nature 368:551–554 (1994); Fling, S. P., et al., Nature 368:554–558 (1994). Thus, our finding that CD1b transfected T2 cells can present M. tuberculosis to DN1 suggests that the antigen processing requirements for CD1b and MHC class II molecules, although similar with regard to chloroquine sensitivity, are not identical.

Several investigators have speculated that T-cells lacking expression of both CD4 and CD8 molecules may recognize antigens presented by cell surface molecules other than those encoded by classical MHC class I and II loci. Porcelli, S., et al., Immun. Rev. 120:137–183 (1991); Janeway, C. A. Jr., et al., Immun. Today 6:73–76 (1988); Bluestone, J. A., and Matis, L. A., J. Immun. 142:1785–1788 (1989). The above results show that one member of the CD1 family, CD1b, can restrict the specific response of MHC unrestricted CD4$^-$8$^-$ T-cells to an exogenous foreign antigen. Like other CD1 proteins, CD1b heavy chains associate noncovalently with $\beta_2$-microglobulin (Olive, D., et al., Immunogenetics 20:253–264 (1984)) and show limited but significant sequence homology to both MHC class I and class II molecules. Calabi, F., and Milstein, C., Nature 323:540–543 (1986); Balk, S. P., et al., Proc. Natl. Acad. Sci. USA 86:252–256 (1989). These structural features of CD1b, together with its critical role in antigen recognition (described above), support the conclusion that CD1b is a nonpolymorphic antigen presenting molecule encoded by a genetic locus unlinked to the MHC.

These results indicate a potential role for CD1 restricted T-cells in normal host defense against microbial disease. The above results suggest a functional parallel between CD1 and MHC class II molecules, since both mediate presentation of exogenous antigens processed through a chloroquine sensitive pathway, and both can also act as ligands for the TCRs of autoreactive T-cells. Porcelli, S., et al., Nature 341:447–450 (1989); Glimcher, L. H., and Shevach, E. M., J. Exp. Med. 156:640–645 (1982). The limited tissue distribution of CD1 molecules in vivo provides a further similarity with the MHC class II family since members of both families are prominently expressed on cell types involved in antigen presentation to T-cells, including Langerhans's cells, dendritic cells in lymphoid and many other tissues, 8 cells and possibly cytokine activated monocytes. Porcelli, S., et al., Immun. Rev. 120:137–183 (1991). In contrast, the lack of structural polymorphism of CD1 molecules, their unique cytokine regulation on monocytes, and the CD4$^-$8$^-$ phenotype of the CD1 restricted T-cells described herein are important differences that distinguish the CD1 and MHC antigen presenting systems. These differences point to a distinct role for CD1 restricted T-cells in cell-mediated immunity.

EXAMPLE 2

A Non-Peptide Antigen is Presented by CD1b

Methods

The CD1b-presented antigen is a nondialyzable macromolecule (data not shown). More antigenic (i.e., T-cell proliferative) activity could be obtained from soluble aqueous sonicates of M. tb. by adding detergents such as CHAPS or octylglucoside during the sonication (see above). This result suggests that the antigen is hydrophobic.

In order to characterize the chemical nature of the antigens presented by CD1, mycobacterial antigens were purified from the nonpathogenic M. tb. strain H37Ra (Difco) and M. fortuitum (a rapidly growing strain that also contains antigenic activity). Bacteria were either commercially available (M. tb. H37Ra, Difco) or grown and harvested (M. fortuitum), sonicated and subjected to sequential fractionation protocols and analyzed for biological activity. All fractions generated were tested for their ability to stimulate the DN T-cell line DN1 in a 5 day proliferation assay using irradiated, GM-CSF- and IL-4treated monocytes as APCs and measuring $^3$H-thymidine incorporation in a 6 hour pulse (Porcelli, S., et al., Nature 360:593–597 (1992)). Cell wall, cell membrane and cytoplasmic fractions were prepared from either M. tb. or M. fortuitum using a method adapted from published protocols. Hunter, S. W., et al., Journal of Biological Chemistry 265:14065–14068 (1990). Briefly, cells were lyophilized, resuspended in PBS/octylglucoside, sonicated for 20 minutes and subjected to differential ultracentrifugation to produce cytosolic, membrane, and cell wall fractions. The cell wall pellets were further purified by a differential sucrose gradient. Characteristic structural features of the three fractions were confirmed by negative staining with electron microscopy. The majority of the bioactivity for the DN1 cell line was present within the cell wall fraction (data not shown).

To directly assess whether the CD1b-restricted antigen is a protein, a series of protease digestions of the antigen were performed. Using a variety of endopeptidases with either limited amino acid specificity (chymotrypsin (hydrophobic residues), trypsin (lys, arg), and V-8 (acidic)), or broad amino acid recognition (subtilisin, proteinase K, pronase), sonicates of either M. tb. or *M. fortuitum* were digested and then assayed for the ability to induce T-cell proliferative responses. As a control, a DR7 restricted, CD4$^+$ T-cell clone DG.1, derived in this laboratory which recognizes a determinant in mycobacterial PPD (purified protein derivative) was also tested. Analysis by SDS-PAGE and subsequent silver stain demonstrated that digestion with V8 protease, proteinase K, pronase E or subtilisin degrades the proteins contained in mycobacterial antigen preparations (data not shown).

Results

The *M. tuberculosis* antigen recognized by DG.1, a representative CD4+ MHC Class II restricted T-cell line, is rendered ineffective by treatment with V8 protease, proteinase K, or trypsin (FIG. 6). As shown in FIG. 6, DG.1 cells proliferated strongly in response to the mock digest of the mycobacterial sonicate, but with the exception of chymotrypsin, all of the other protease treatments completely abrogated the proliferative response.

In contrast, the *M. tuberculosis* and *M. fortuitum* antigens presented to line DN1 by CD1b is unaffected by these broadly reactive proteases (FIGS. 7 and 8, respectively). The mycobacterial antigen presented by CD1b is fundamentally different than that presented by MHC Class I and II antigen presenting molecules. It is well established that MHC molecules bind and present peptide antigens of about 8–9 amino acids for class I and 13–25 amino acids for class II. Because this CD1b-presented antigen is a macromolecule which is protease resistant, it is unlikely to be a peptide. Thus, the CD1 system is the first known antigen presentation system which present foreign substances other than peptides to $\alpha$:$\beta$ TCR$^+$ T-cells.

EXAMPLE 3
Purification of a CD1b-Presented Antigen from *M. tuberculosis*

Methods

*M. fortuitum* bacteria were grown in liquid culture to stationary phase and collected by centrifugation, sterilized by stream autoclaving (250° C., 18 p.s.i.) and lyophilized. Desiccated M. tb. (strain H37Ra, Difco) or *M. fortuitum* bacteria were suspended in phosphate buffered saline (200 mg bacteria per 5 ml PBS), and the bacterial suspension was sonicated with a probe sonicator to disrupt the cells. The resulting sonicate was extracted with organic solvents using a Folch based 2 phase extraction system (chloroform/methanol/water) which quantitatively extracts mycobacterial lipids into an organic phase. Goren, M. B., and Brennan, P. J., *Mycobacterial Lipids: Chemistry and Biologic Activities in Tuberculosis,* 1979. The sonicate was combined with three volumes of a chloroform:methanol (2:1 v/v) solution in a glass container, and the mixture was vigorously shaken at room temperature for 24 hours. The phases of the mixture were separated by centrifugation at 800 g, and the organic phase was collected and transferred into a glass boiling flask. Each fraction was then dried by rotary evaporation (organic phase) or lyophilized (aqueous phase and interface). After evaporation, the organic phase left a thin film of waxy material on the surface of the flask. In order to prepare material to be tested in T-cell proliferation assays, aliquots of fractions were reconstituted as liposomes by the addition of water (20 ml per 200 mg of bacteria in original sonicate) followed by sonication in a water bath sonicator. The resulting crude suspension was then forced repeatedly through a 0.1 nm filter membrane in order to create a liposome suspension of uniform size. Alternatively, T-cell media with 10% fetal calf serum was added to the dried fraction and sonicated without additional preparation.

For further purification, the material extracted from *M. tuberculosis* as described above was dissolved in hexane and applied to a column of Silicic Acid. Eluting with organic solvents of increasing polarity over silica columns achieves separation of lipids based on their polarity. The most polar lipids such as phospholipids bind the strongest to the silica column and elute last, while glycolipids generally bind less tightly and elute earlier. Neutral lipids such as triglycerides or sterols bind the weakest and therefore elute first.

Small open solid phase extraction (SPE) columns (BakerBond, J. T. Baker) were preferred because of the ability to process many samples simultaneously. A silica based "bonded" column (covalently linked) with cyano (CN) functional groups was used to fractionate the organic extracts of M. tb. The organic phase of the choloroform/methanol extract of bacteria was dried and resuspended in hexane. The equivalent of 5.3 mg of desiccated bacteria in 200 µl hexane was loaded onto a 0.5 gram CN SPE column. The column was washed with hexane and then with 25% (v/v) chloroform in hexane. Next, the bioactive fraction was eluted with 85% (v/v) chloroform in hexane with over 100% recovery of bioactivity. Analyzing the active fraction on silica based TLC plates, according to the method of Kupke and Zeugner (Christie, W. W., *Lipid Analysis,* p. 117, Pergamon Press, Oxford, U.K., 1982)), only two major species of lipid were visualized with cupric acetate, corresponding to free fatty acids and mycolic acids (data not shown). This result reflects a marked purification from the starting organic material.

Proliferation assays were harvested on day 2 (DG.SF68), day 3 (DG.1) or day 5 (DN1). DG.SF68 is a V$\gamma$2V$\delta$2 T-cell clone derived in this lab (PNAS in press, CM). APCs were GM-CSF- and IL-4-treated monocytes (DN1) or PBMC (DR7$^+$) (DG.1), or untreated PBMC (DG.SF68). Cytolytic assays are displayed as % specific lysis and were performed as described. Porcelli, S., et al., *Nature* 341:447–450 (1989). Data shown (FIG. 9) are with an effector to target ratio of 50:1 and with *M. tuberculosis* antigen at a dilution of 1:20.

Results

The relevant antigen of *M. tuberculosis* is isolated from a commercial preparation of strain H37Ra (Difco) by extraction into a mixture of chloroform and methanol as described above. Although the interface contains greater than 95% of the proteins, 100% of the CD1b-restricted antigenic activity (i.e., ability to induce an $\alpha$:$\beta$ TCR DN T-cell proliferative response) of the mycobacterium extracts into the organic phase (FIG. 9a). This strongly supports the original conclusion of the nonpeptide nature of the relevant bacterial antigen. In contrast, a conventional MHC class II restricted antigen recognized by DN $\gamma$:$\delta$ TCR$^+$ T-cells was located in the phase interface between the aqueous and organic phases (FIG. 9b). In contrast, in four independent antigen preparations, the CD1b-restricted antigen quantitatively partitioned into the organic phase. Results of transfectant cytolytic assays of the phases confirmed that the CD1b-presented antigen is present in the organic phase (FIG. 10).

Under these conditions, 100% of the mycobacterial CD1-presented antigenic activity was quantitatively recovered after CN SPE chromatography. In addition, the organic phase extraction served as an excellent purification step and the organic phase was used as a starting material for subsequent chromatography. An alternative and somewhat more general procedure to purify the antigen for subsequent chromatography is to saponify whole or sonicated bacteria and extract with an acidified solution of hexanes. Further purification of the antigen is obtained using Silicic Acid chromatography as described above.

EXAMPLE 4

Mycolic Acid is a Mycobacterial CD1b-Presented Antigen

Given the above results, and other preliminary data suggesting that the T-cell stimulatory activity co-chromatographed on CN modified silica HPLC columns with preparations of free fatty acid acyl chains (data not shown), it seemed plausible that the CD1b-presented antigen is a unique mycobacterial lipid, possibly a mycolic acid.

Mycobacteria contain an extraordinary proportion of lipids, amounting to 40% of the dry weight of bacillus and 60% of the cell wall; the mycolic acids are perhaps the most numerous and diverse members of mycobacterial lipids. Goren, M. B., and Brennan, P. J., *Mycobacterial Lipids: Chemistry and Biologic Activities in Tuberculosis*, 1979. Mycolic acids are α-branched, β-hydroxy fatty acids forming a unique set of structures that are found in mycobacteria and related bacterial species. Wolinsky, E., "Mycobacteria," Chapter 37 in *Microbiology: Including Immunology and Molecular Genetics*, 3rd Ed., Davis, B. H., ed., Harper & Row, Philadelphia, 1980.

Mycolic acids are principally found in the cell wall, esterified to arabinogalactan polymers linked to the core peptidoglycan (McNeil, M. R., and Brennan, P. J., *Res. Microbiol.* 142:451–563 (1991); Besra, G. S., *Biochemistry* 30:7772–7777 (1991); McNeil, M., et al., *Journal of Biological Chemistry* 266:13217–13223 (1991)) and can be released by either alkaline or acid hydrolysis (saponification). Minnikin, D. E., "Mycolic acids" in *CRC Handbook of Chromatography: Analysis of Lipids*, Murhergee, K. D., and Weber, N., eds., CRC Press, 1993. Mycolic acids are the major component of the lipid coat surrounding the organism, giving the organism its hydrophobic surface and characteristic acid fast staining. Goren, M. B., and Brennan, P. J., *Mycobacterial Lipids: Chemistry and Biologic Activities in Tuberculosis*, 1979.

Unlike eukaryotic and bacterial fatty acids, which range in size from $C_{12}$–$C_{24}$, mycolic acids of Mycobacteria range in size from $C_{60}$–$C_{90}$. Minnikin, D. E., "Lipids: Complex Lipids, their Chemistry, Biosynthesis and Roles" in *The Biology of Mycobacteria*, Vol. 1, Ratledge, C., and Sanford, J., eds., Academic Press, London, 1982. Mycolic acids, in contrast to the straight chain fatty acids, have a branched alkyl group at the α carbon and a hydroxyl group at the β carbon. Goren, M. B., and Brennan, P. J., *Mycobacterial Lipids: Chemistry and Biologic Activities in Tuberculosis*, 1979; Minnikin, D. E., "Lipids: Complex Lipids, their Chemistry, Biosynthesis and Roles" in *The Biology of Mycobacteria*, Vol. 1, Ratledge, C., and Sanford, J., eds., Academic Press, London, 1982; Takayama, K., and Qureshi, N., "Structure and Synthesis of Lipids" in *The Mycobacteria: A Sourcebook*, Part A, Kubica, G. P., and Wayne, L. G., eds., Marcel Dekker, New York & Basel, 1984. The main long alkyl chain of the mycolic acid (the so-called mero group) is heterogenous both in length and in attached functional groups. In addition to alkene groups (double bonds), the functional groups of mycolic acids include methoxyl, keto, lone methyl barances, ethylenic and cyclopropanoid groups. Minnikin, D. E., "Lipids: Complex Lipids, their Chemistry, Biosynthesis and Roles" in *The Biology of Mycobacteria*, Vol. 1, Ratledge, C., and Sanford, J., eds., Academic Press, London, 1982. The large array of functional groups available to mycolic acids, their variable chain length, and their heterogeneity among strains, allow mycolic acids to achieve a potentially large degree of antigenic variation similar to that provided by peptides with heterogeneity among amino acid side chains. Thus, these lipid molecules may have an immunological relevance not previously appreciated. For each mycobacterial species a distinguishable fingerprint exists based on the patterns of mycolic acid molecules present. Such patterns have been determined for individual species by thin layer chromatography (TLC). Minnikin, D. E., "Lipids: Complex Lipids, their Chemistry, Biosynthesis and Roles" in *The Biology of Mycobacteria*, Vol. 1, Ratledge, C., and Sanford, J., eds., Academic Press, London, 1982; Dobson, G., et al., *Chemical Methods in Bacterial Systematics*, Academic Press, 1985; Valero-Guillen, P. L., et al., *Journal of Applied Bacteriology* 59:113–126 (1985)), gas chromatography (GC) (Valero-Guillen, P. L., et al., *Journal of Applied Bacteriology* 59:113–126 (1985); Athalye, M., et al., *Journal of Applied Bacteriology* 58:507–512 (1985); Luquin, M., et al., *Journal of Clinical Microbiology* 29:120–130 (1991)) and by high pressure liquid chromatography (HPLC). Qureshi, N., et al., *Journal of Biological Chemistry* 253:5411–5417 (1978); Qureshi, N., et al., *Journal of Biological Chemistry* 255:182–189 (1980); Butler, W. R., et al., *Journal of Clinical Microbiology* 29:2468–2472 (1991); Butler, W. R., and Kilburn, J. O., *Journal of Clinical Microbiology* 28:2094–2098 (1990).

Methods

In order to determine if the CD1-presented antigen described above is a mycolic acid, an HPLC method that separates mycolic acids on C18 reverse phase column chromatography was used to prepare mycolic acids. Butler, W. R., et al., *Journal of Clinical Microbiology* 23:182–185 (1986); Butler, W. R., et al., *Journal of Clinical Microbiology* 26:50–53 (1988); Floyd, M. M., et al., *Journal of Clinical Microbiology* 30:1327–1330 (1992). Reversed phase chromatography separates acyl chains primarily on the basis of the length of the acyl chain or "carbon number," thus it is relatively easy to achieve good separation between free fatty acids and mycolic acids which are much larger.

This HPLC method requires an initial saponification of the sample, followed by derivitization of the fatty acids or mycolic acids with the ultraviolet ($OD_{254}$) absorbing compound p-bromophenacylbromide, which attaches to the carboxyl terminus of an acyl chain. In preliminary experiments, we determined that the process of derivatizing the bacterial fraction with p-phenacylbromide destroyed bioactivity. However, the CD1b-restricted antigenic activity could then be recovered by saponification with methanolic KOH, a process which frees the carboxyl end of the acyl chain by cleaving off the phenacylbromide group (as assayed by $OD_{254}$ on HPLC). This result indicates that the acyl chain must be cleaved in order to achieve a form which is presentable by CD1 positive APCs and/or that a free carboxyl group is critical for presentation of the CD1b-restricted antigen. This is additional evidence that the antigen comprises an acyl chain.

The SPE CN column purified preparation (Example 3) was used as a starting material for the C18 chromatography.

Samples were saponified with methanolic KOH and derivatized with the UV absorbing group bromophenacyl bromide. The active fraction was run on a C18 column (Alltech Nucleosil C18 5 μm, 25 cm×4.6 mm) using a linear gradient of 30 to 90% methylene chloride in methanol over 50 minutes at 1 ml/min. Using as a reference a $C_{90}$ internal standard (Ribi), the resulting chromatogram (FIG. 12, panel a, upper portion) has a pattern comparable to published results. Floyd, M. M., et al., *Journal of Clinical Microbiology* 30:1327–1330 (1992). Fractions were resuspended in complete media with 10% FCS and tested at a 1:17 dilution relative to the original sonicate volume.

Results

Bioactivity, assayed by the T-cell proliferative response assay, was found to comigrate with early peaks in the region of the mycolic acids (FIG. 12a). To confirm that mycolic acid is presented by CD1b, an alternative source of mycolic acids, purified cord factor (trehalose dimycolate; FIG. 11) was tested. Upon saponification, purified trehalose dimycolate from either M. tb. (from Sigma) or *M. kansasii* (gift of Patrick Brennan) stimulated the proliferation of the T-cell line DN1 (FIG. 12b). However, no stimulation was achieved by material prepared from saponified trehalose dibehanate, a synthetic derivative of cord factor which contains two $C_{22}$ fatty acid chains, rather than mycolic acids, that are liberated by saponification. This strongly argues that mycolic acid, not trehalose (which is present in each of the samples) nor fatty acids, is the antigen presented by CD1b to the double negative α:β TCR T-cell line DN1. A HPLC analysis of the saponified Sigma cord factor was then performed, and again the bioactivity was located in fractions corresponding to the early mycolic acid peaks (FIG. 12c). Together, the above data demonstrate that the CD1b restricted mycobacterial antigen recognized by the T-cell line DN1 is a species of mycolic acid.

Mycobacteria are known to be highly effective adjuvants. Aldovini, A., and Young, R. A., *Nature* 351:479–482 (1991). One source of the CD1b-presented antigen, mycolic acid, used herein is trehalose dimycolate (i.e., Mycobacterial cord factor), which has been shown to enhance antibody formation (Bekierkunst, A., et al., *J. Bacteriol.* 100:95–102 (1969); Bekierkunst, A., et al., *Infection and Immunity* 4:245–255 (1971); Bekierkunst, A., et al., *Infection and Immunity* 4:256–263 (1971)) and to stimulate nonspecific immunity to bacterial infections (Parant, M., et al., *Infect. Immun.* 20:12–19 (1978)) and tumors (Bekierkunst, A., et al., *Infection and Immunity* 10:1044–1050 (1974).

In order to ensure that the purified antigenic activity contains a bona fide antigen and not a nonspecific mitogen, we looked at the specificity of the T-cell proliferative response to crude M. tb. preparations and HPLC-purified mycolic acid from M. tb. and saponified cord factor. Total sonicates of M. tb. (FIG. 14, upper panel) contain antigen recognized by the MHC class II restricted $CD4^+$ α:β $TCR^+$ T-cell line DG.1, as well as an antigen recognized by the CD1b-restricted T-cell line DN1 and the CD1c-restricted T-cell line DN6 (see Example 5, below). However, HPLC-purified mycolic acid from either M. tb. (FIG. 14, middle panel) or from saponified cord factor (FIG. 14, lower panel) contains antigens recognized only by CD1b-restricted DN1 T-cells. This specificity is also demonstrated in the transfectant cytolytic assay (FIG. 13). The CD1b-restricted response of DN1 was blocked by anti-CD1b antibodies, but was not affected by antibodies to MHC class I or II (FIG. 15, upper panel).

EXAMPLE 5

Antigen Presentation by CD1c

In addition to the presentation of antigens by CD1b disclosed in Example 1, CD1c molecules also present antigens. A separate $CD4^-8^-$ α:β $TCR^+$ T-cell line, derived by repeated stimulation with monocytes treated with GM-CSF and IL-4 (to induce CD1 expression) and *M. tuberculosis* antigens was isolated and named DN2 (also referred to as 8.23.DN1). Proliferation of DN2 is completely inhibited by the addition of mAbs to CD1c, but is not affected by mAbs to CD1b (FIG. 15, lower panel). A cytolytic assay confirms this result: C1R cells transfected with vector only or with vector encoding CD1a, CD1b or CD1c were preincubated with or without *M. tuberculosis* sonicate and used as targets in a cytolytic assay. Only $CD1c^+$ C1R cells are recognized (FIG. 16); recognition is enhanced by preincubation with the sonicate. Therefore, CD1c molecules present *M. tuberculosis* antigens to DN2 T-cells.

A second CD1c-restricted $CD4^-8^-$ α:β $TCR^+$ T-cell line, derived by repeated stimulation with monocytes treated with GM-CSF and IL-4 (to induce CD1 expression) and *M. tuberculosis* antigens was isolated and named DN6. Cytolytic assays (FIG. 17) indicate that DN6 lyses $CD1c^+$ cells in the presence of M. tb. antigen.

EXAMPLE 6

Characterization of a CD1c-Presented Antigen from *M. tuberculosis*

The antigen presented to DN6 T-cells by CD1c is not mycolic acid (FIG. 14, middle panel). However, chemical characterization of the antigen recognized by DN6 indicates that the antigen is a complex lipid. When M. tb. sonicates are extracted with chloroform:methanol (as described in Example 3), the antigenic activity is found substantially in both the phase interface and the organic phase (FIG. 18). Antigen recovered from the organic phase can be bound to CN SPE columns and eluted (as described in Example 3). These studies demonstrate that the antigen is hydrophobic and has the chromatographic properties of a lipid.

However, unlike the CD1b-restricted mycobacterial antigen, results of additional experiments indicate that the DN6recognized CD1c-presented antigen is a complex lipid and not a free acyl chain. Saponification of M. tb. sonicates eliminates the proliferative response of DN6 (FIG. 20). Because saponification breaks ester linkages that connect acyl chains to carbohydrate backbones, this result suggests that the antigen recognized by DN6 T-cells is a, or comprises an additional, moiety other than a free acyl chain. Saponification presumably destroys or removes the additional moiety which may be, e.g., a polysaccharide backbone or branch point. Thus, in contrast to the recognition of free mycolic acid by the DN1 T-cell line, the DN6 T-cell line recognizes a more complex lipid structure.

It is noteworthy that the CD1-presented antigens recognized by T-cell lines DN1 and DN6 are not unique to *M. tuberculosis*. Rather, the DN1- and DN6-recognized CD1-presented antigens are cross-reactive to antigens found in many Mycobacterial species tested to date (*M. fortuitum, M. avium, M. bovis* (BCG) and *M. leprae*). In the case of CD1c-restricted recognition by DN6 T-cells, an antigen is recognized in Corynebacteria (data not shown), a separate but related genera of bacteria which produce mycolic acids. Takayama, K., and Qureshi, N., "Structure and Synthesis of Lipids" in *The Mycobacteria: A Sourcebook*, Part A, Kubica, G. P., and Wayne, L. G., eds., Marcel Dekker, New York & Basel, 1984. Thus, CD1-presented antigens include at least several bacterial lipid antigens; in the case of autoimmunity, CD1-presented antigens include endogenous lipid antigens.

EXAMPLE 7
CD1-Presented Antigens from *M. leprae*

In order to derive DN α:β TCR$^+$ T-cell lines from leprous lesions, T-cells from such lesions or PBMC were stimulated by culture with CD1$^+$ APCs and *M. leprae*. Immunomagnetic depletion removed CD4$^+$, CD8$^+$ and γ:δ-TCR$^+$ T-cells. The ability of remaining CD4$^-$8$^-$ α:β TCR$^+$ T-cells to respond to *M. leprae* antigens was assessed by $^3$H-thymidine incorporation using allogenic CD1+ monocytes as APCs.

Four of six DN α:β TCR$^+$ T-cell lines isolated in the above manner proliferated strongly in the presence of *M. leprae* and allogenic CD1+ APCs, whereas little or no stimulation of growth was detected in the presence of the allogenic CD1+ APCs alone, and no proliferation in reponse to *M. leprae* was detected in the presence of APCs not expressing CD1 proteins. Thus, the four DN α:β TCR$^+$ T-cell lines respond to, and proliferate in the presence of, CD1-presented antigen from *M. leprae*.

Two DN α:β TCR$^+$ T-cell lines, isolated from leprous lesions and designated LDN1 and LDN4, were subjected to further analyses. To determine which CD1 molecules (i.e., CD1a, CD1b, Cd1c, etc.) were specifically responsible for *M. leprae* antigen presentation, two sets of experiments were performed. First, proliferation studies were performed in which CD1+ APCs were incubated with antibodies to CD1a, CD1b or CD1c. Second, C1R cells were transformed with genes encoding different CD1 molecules and used as target cells in cytolytic assays.

*M. leprae*-induced proliferation of the LDN1 T-cell line was inhibited by greater than 63% by anti-CD1c, but anti-CD1a, anti-CD1b and an isotype-matched non-CD1-reactive antibody had no effect on the proliferative response to *M. leprae* (FIG. 20, upper panel). Similarly, LND1 cells lysed CD1c-transformed C1R cells in an *M. leprae* antigen specific manner, but did not lyse cells transfected with CD1a or CD1b or mock transfected C1R cells.

A second *M. leprae* antigen reactive DN α:β TCR$^+$ T-cell line derived from a leprous lesion, LND4, was found to be Cd1b restricted. The ability of this T-cell line to proliferate in the presence of *M. leprae* was completely inhibited by the addition of anti-CD1b monoclonal antibodies (MAbs) (FIG. 20, lower panel). Similarly, LND4 lysed CD1b-transfected C1R cells in an antigen specific manner, but did not lyse CD1a or CD1c transfectants. Furthermore, the ability of LND4 to lyse antigen-pulsed CD1b targets was blocked by anti-CD1b MAbs. In all DN α:β TCR$^+$ T-cell lines tested, antibodies to MHC class I and class II molecules had no effect on proliferation in response to *M. leprae*.

The presence of CD 1-bearing cells in leprous lesions was examined by immunohistological examination of tissue sections using MAbs to CD1 (data not shown). These analyses reveal that CD1a+, CD1b+ and CD1c+ cells occur in in tuberculoid granulomas to a greater extent than in lepromatous granulomas. Although CD1a was expressed in the epidermis as well as the dermal granulomas of tuberculoid leprous lesions, CD1b and CD1c were only expressed in dermal granulomas. Furthermore, Il-10, which is strongly expressed in lepromatous lesions (Yamamura, M., et al., *Science* 254:277–279 (1991)) could inhibit the expression of CD1 on monocytes (data not shown). The correlation of CD1 expression with resistance in leprosy suggests a role for CD1-mediated restriction in the generation of cell-mediated immunity.

The functional role of DN α:β TCR$^+$ T-cells was examined by studying their cytokine secretion patterns. Anti-CD3 stimulation of DN α:β TCR$^+$ T-cells resulted in the release of interferon-γ (IFN-γ) (median=647 pg/ml) in four of the five DN α:β TCR$^+$ T-cell lines, but produced little or no IL-4 (median <20 pg/ml), although one T-cell line produced IL-4 (99 pg/ml) but no detectable IFN-γ (<20 pg/ml). IL-5, IL-6 and IL-10 were not detected in the superantants of anti-CD3-stimulated DN T-cells. These data suggest that the majority of *M. leprae*-reactive DN α:β TCR$^+$ T-cells secrete the type 1 cytokine pattern.

EXAMPLE 8
LAM is a CD1b-Presented Antigen from *M. leprae*

In order to elucidate the biochemical nature of the antigens recognized by CD1-restricted T-cells, purified cell wall constituents of *M. leprae* were prepared and assayed for biological activity. LDN4, in the presence of CD1 expressing antigen presenting cells, proliferated in response to lipid-containing fractions derived from the cell wall (SolPCW), but not to protein-enriched fractions from the membrane and cytosol that have been depleted of lipids (SP-) (FIG. 21). No response was observed to insoluble fractions of the cell wall (CWC) or to mycolic acid-arabinogalactan-peptidoglycan (mAGP). These data indicate that DN αβ T-cells recognize non-peptide antigens of *M. leprae* in a CD1-restricted manner.

The reactivities of LDN4 correlated with the presence of lipoarabinomannan (LAM; FIG. 22), and we subsequently found that this line proliferated to purified LAM. The ability of LDN4 to respond to LAM was blocked by anti-CD1b antibody (FIG. 23). BDN2, an α:β double negative T-cell line which responds to *M. leprae* in a CD1c restricted manner, also responded to LAM. The ability of BDN2 to respond to LAM was blocked by anti-CD1c antibody (data not shown).

EXAMPLE 9
Derivatives and Analogs of LAM, and CD1-Dependent Uses Thereof

LAM is a nonprotein molecule, one of a class known as "amphiphiles," possessing both hydrophobic and hydrophilic components (FIG. 22). Hunter, S. W., et al., *J. Biol. Chem.* 261:12345–12531 (1986); Hunter, S. W., et al., *J. Biol. Chem.* 265:9272–9279 (1990). The hydrophobic domain is a phosphatidyl inositol linked to a hydrophilic heteropolysaccharide composed of a mannan core and branched arabinan side chains with short mannose oligosaccharide "caps." Chatterjee, D., et al., *J. Biol. Chem.* 267:6228–6233 (1992); Chatterjee, D., et al., *J. Biol. Chem.* 267:6234–6239 (1992). Protocols for the purification of LAM have been described. Hunter, S. W., et al., *J. Biol. Chem.* 261:12345–12531 (1986). Fast Atom Bombardment-Mass Spectrometry analysis indicates the virtually complete purity of the *M. leprae* LAM (>99.9%).

Previously, *M. leprae* and *M. tuberculosis* LAM have been shown to have distinct structures which result in different B-cell epitopes. Prinzis, S., et al., *J. Gen. Microbiol.* 139:2649–2658 (1993). Therefore, it is conceivable that LAM from different mycobacterial species may possess distinct T-cell epitopes. It is also noteworthy that gram positive bacteria contain structurally related lipomannans and lipoteichoic acids, so that recognition of these molecules by T-cells may be a part of the immune response directed generally to bacterial pathogens.

To determine the domain(s) of LAM responsible for stimulating DN α:β T-cells, chemical derivatives of LAM were tested for their ability to stimulate DN α:β T-cells. Mild alkaline hydrolysis releases the fatty acid moieties of LAM, while leaving the carbohydrate intact. This deacylated LAM (dLAM) loses the ability to stimulate LDN4 at concentrations where the native LAM caused striking T-cell proliferation (FIG. 24). In contrast to deacylated LAM, phosphatidylinositol mannoside (PIM) stimulated LDN4 ten-fold more than media alone (FIG. 24). These data suggest that the lipid domain of LAM is required for T-cell stimulation, but that the repeating mannan-arabinan backbone of LAM may not be required.

Finally, the cross-recognition of LAMs from other mycobacteria was investigated with regard to two DN α:β T-cell lines (FIG. 25). The leprosy-derived T-cell line LDN4 was stimulated by *M. leprae* LAM (Lep LAM), but not by LAM from a clinical isolate of *M. tuberculosis* (TBE-LAM) or LAM from a virulent laboratory strain of *M. tuberculosis* (Rv LAM). These results demonstrate a species specificity of LDN4 for *M. leprae* LAM. In contrast, T-cell line BDN2 responded to *M. tuberculosis* LAM (TBE LAM and Rv LAM) as well as to *M. leprae* LAM (Lep LAM). Taken together, these results demonstrate that both species-specific and cross-reactive determinants of LAM are recognized by DN α:β T-cells.

EXAMPLE 10

Vaccines Comprising CD1-Presented Antigens

Prior to the present disclosure, lipids were not known to possess potentially potent specific T-cell-mediated immunogenicity. The CD1-presented lipid antigens described herein may be used as essential components of compositions designed to function as vaccines to mycobacterial pathogens. Vaccines comprising CD1-presented antigens may be administered directly by injection. Alternatively, due to the presence of CD1 on cells found in the gastrointestinal epithelium (Bleicher, P. A., et al., *Science* 250:679–682 (1990)), oral administration of vaccines comprising CD1-presented antigens may be employed to introduce such vaccines into an animal in need of a vaccine comprising a CD1-presented antigen.

Vaccines comprising the CD1-presented antigens of the present invention are formulated according to known methods. *Remington's Pharmaceutical Sciences*, 18th Ed., Gennaro, A. R., ed., Mack, Easton, 1990; *The Pharmacologist Basis of Therapeutics*, 7th Ed., Gilman, A. G., et al., eds., MacMillian, New York, 1985. Pharmaceutically acceptable lipid-stabilizing and -solubilizing agents known to those of skill in the art may be added to vaccines comprising CD1-presented antigens to enhance their effectiveness. Teng, N., et al., PCT published patent application WO 91/01750 (Feb. 21, 1991). Nunberg, J. H., U.S. Pat. No. 4,789,702 (Dec. 6, 1988).

EXAMPLE 11

Means and Methods for Inhibiting CD1-Restricted Antigen Presentation

The disclosure of CD1 antigen presentation system allows for various means and methods of inhibiting CD1-restricted antigen presentation. Any composition which inhibits the processing of CD1-presented antigens, which interferes with the binding of antigen to a CD1 molecule, or which interferes with the binding of the CD1:antigen complex to a TCR molecule, will inhibit CD1-restricted presentation of antigen. Such compositions, called CD1 blocking agents, are useful for controlling undesired T-cell-mediated immunity which occurs, e.g., in autoimmune diseases. Oksenberg, J. R., et al., *J. Neurol. Sci.* 115 (Suppl.):S29–S37 (1993).

CD1 blocking agents include, but are not limited to, (1) a purified CD1 molecule, or a synthetic derivative thereof, capable of binding a CD1-presented antigen and preventing the antigen's interaction with CD1 displayed on APCs; (2) a purified TCR polypeptide, or a synthetic derivative thereof, capable of binding to a CD1-antigen complex on a CD1$^+$ APC and preventing the complex's interaction with T-cell receptors; (3) an antigen antagonist comprising a chemically-modified CD1-presented antigen, or a synthetic derivative of a CD1-presented antigen; (4) a purified CD1-antigen complex, or a synthetic derivative thereof, capable of binding to a T-cell receptor that recognizes a CD1-antigen complex on a CD1$^+$ APC and preventing the T-cell receptor's interaction with CD1-antigen complexes; (5) an antibody which binds a CD1 molecule and thus prevents the interaction of the CD1 molecule and a CD1-presented antigen; (6) a polyclonal or monoclonal antibody which binds a CD1:antigen complex and thus prevents the interaction of the CD1:antigen complex and its cognate TCR; (7) a polyclonal or monoclonal antibody which binds a TCR that recognizes a CD1-presented antigen and thus prevents the interaction of the TCR with its cognate CD1:antigen complex; and (8) a composition which blocks an essential step in the pathway by which CD1-presented antigens are processed prior to being displayed.

The preceding Examples contain exemplars of CD1 blocking agents as follows.

CD1 blocking agents of type (5) are represented by monoclonal antibody WM25 to CD1b, which specifically inhibits CD1b-restricted antigen presentation (FIG. 15, upper panel) and monoclonal antibody 10C3 to CD1c, which specifically inhibits CD1c-restricted antigen presentation (FIG. 15, lower panel). A skilled artisan can used the methods described herein to isolate antibodies which act as CD1 blocking agents of type (6) or (7), and those of skill in the art know how to formulate antibodies for therapeutic purposes. *A Critical Analysis of Antibody Therapy in Transplantation,* Burlington, W. J., ed., CRC Press, Boca Raton, 1992.

CD1 blocking agents of type (8) are represented by chloroquine (FIG. 5c), which inhibits a step in the processing of CD1b-restricted antigens. Methods of formulating and administering chloroquine are known to those of skill in the art. Webster, L. T., "Drugs Used in the Chemotherapy of Protozoal Infections," Chapters 41 and 42 in *Goodman and Gilman's The Pharmacological Basis of Therapeutics,* 8th Ed., Gilman, A. G., et al., eds., Pergamon Press, New York, 1990. Although chloroquine also inhibits MHC-restricted antigen presentation, those skilled in the art can, using the methods disclosed herein, identify and/or isolate compositions which specifically inhibit processing of CD1-restricted antigens.

Blocking agents of type (3), i.e., antigen antagonists, may be derived from CD1-restricted antigens isolated by the methods of the invention. Variants of MHC-restricted peptide antigens, binding with weaker affinities than the original peptide antigen, act as antagonists for mature T-cells in MHC-restricted antigen presentation. Wraith, D. C., et al., *Cell* 59:247–255 (1989); Smilek, D. E., et al., *Proc. Natl. Acad. Sci.* (*USA*) 88:9633–9637 (1991). In like fashion, CD1-presented antigens are isolated by the methods of the invention and are chemically modified, according to standard techniques, in order to generate non-antigenic or weakly antigenic CD1-presented antigen derivatives. For example, mycolic acid derivatized with p-bromophenacylbromide is non-antigenic (Example 4). Antigen antagonists are identified as CD1-presented antigen derivatives which inhibit or prevent the T-cell proliferative or CD1 transfectant cytolytic responses which occur when only the original, unmodified CD1-presented antigen is present (Example 1).

Blocking agents of type (2), i.e., TCR derivatives which block the interaction of the antigen:CD1 complex with the TCR molecules on T-cells, may be prepared from the disclosure by those skilled in the art. DNA molecules encoding TCR polypeptides displayed by a T-cell line that recognizes a CD1-presented antigen of the invention are isolated according to methods known in the art. Oskenberg, J. R., et al., *Proc. Natl. Acad. Sci. (USA)* 86:988–992 (1989); Oksenberg, J. R., et al., *Nature* 345:344–346 (1990) and erratum, *Nature* 353:94 (1991); Uematsu, Y., et al., *Proc. Natl. Acad. Sci. (USA)* 88:534–538 (1991); Panzara, M. A., et al., *Biotechniques* 12:728–735 (1992); Uematsu, Y., *Immunogenet.* 34:174–178 (1991). The DNA sequence is converted into a polypeptide sequence, and the portion of the polypeptide sequence that corresponds to the antigen-binding variable region of a TCR polypeptide is used to design synthetic oligopeptides that bind CD1:antigen complexes on APCs, thereby inhibiting antigen presentation. Oligopeptides are chemically synthesized according to standard methods (Stewart and Young, *Solid Phase Peptide Synthesis*, Pierce Chemical Co., Rockland, Ill., 1985) and purified from reaction mixtures by reversed phase high pressure liquid chromatography (HPLC). Pilot trials of treatment of humans suffering from an autoimmune disease, MS, with peptides derived from MHC-restricted $\alpha$:$\beta$ TCR molecules is currently underway. Oksenberg, J. R., et al., *J. Neurol. Sci.* 115 (Suppl.):S29–S37 (1993). TCR-derived peptides which function as CD1 blocking agents are identified as TCR-derived peptides which inhibit or prevent the T-cell proliferative or CD1 transfectant cytolytic responses which occur in the presence of CD1-presented antigen (Example 1).

The assays for CD1-presented antigens described herein may be used to screen molecular libraries for CD1 blocking agents. Libraries of molecularly diverse compositions are prepared by chemical, biochemical and/or biotechnological means. Such libraries include combinatorial libraries of synthetic peptides (Houghten, R. A., et al., *BioTechniques* 13:412–421 (1992)) and fusion protein libraries prepared by recombinant DNA technology, e.g., phage display libraries. Koivunen, E., et al., *J. Biol. Chem.* 268:20205–20210 (1993). The libraries are screened for the presence of members which inhibit or prevent the DN T-cell proliferative and/or CD1 cytolytic responses described herein. CD1 blocking members are isolated from the library according to techniques known in the art and appropriate for the type of library employed. Lowman, H. B., et al., *Biochemistry* 30:10832–10838 (1991); Felicia, F., et al., *J. Mol. Biol.* 22:301–310 (1991); Dandekar, T., et al., *Neurochem. Int.* 7:247–253 (1985); Owens, R. A., et al., *Biophys. Res. Commun.* 181:402–408 (1991).

In order to detect a CD1 blocking agent in a sample, assays for CD1-presented antigen are performed in duplicate. The first (control) assay is a T-cell proliferative or cytolytic assay performed essentially as described in Example 1. The second assay is substantially the same as the first assay except that the second assay additionally contains a sample suspected of containing a CD1 blocking agent. The presence of CD1 blocking agents in the sample correlates with a T-cell proliferative or cytolytic response in the second assay that is significantly less than that measured in the first assay.

EXAMPLE 12

T-Cell Reactivity to CD1-Presented Antigens

As described in Example 1, T-cell reactivity to CD1-restricted antigens was initially found among a subset of T-cells, i.e., CD4⁻8⁻ TCR $\alpha\beta^+$ T-cells. However, additional examples of CD1-restricted foreign antigen recognition of microbial antigens is also found in CD8⁺ TCR $\alpha\beta^{30}$ T-cells, as well as among TCR $\gamma\delta^+$ T-cells.

CD1 Restricts the Response of TCR $\gamma\delta^+$ T-cells to an Antigen

Human peripheral mononuclear cells were obtained from a leukopak. After depletion of the monocyte population by plastic adherence, TCR $\gamma\delta^+$ T-cells were isolated using magnetic cell sorting (MACS) as previously described ((Schittek, B. and Rajewsky, K., *Nature* 346:749–751 (1990)). Briefly, PBMC were labelled with biotinylated anti-$\gamma\delta$ TCR monoclonal antibody (TCR$\delta$1), followed by staining with FITC-Avidin (CALTAG) and biotinylated beads (Miltenyi Biotec, Sunnyvale, Calif.). Cells were then positively selected in a strong magnetic field through a high capacity ($3 \times 10^7$ cells) column (Miltenyi Biotec, Sunnyvale, Calif.). The purity of the cells was assessed by FACS immediately after purification. Starting from $2 \times 10^9$ PBMC, this procedure typically allows one to obtain $2 \times 10^7$ TCR $\gamma\delta^+$ T-cells with >98% purity.

After three days in vitro without specific stimulation, the purified TCR $\gamma\delta^+$ T-cells were cultured with autologous GM-CSF- and IL-4-treated CD1⁺ monocytes at a 1:1 ratio in 24 well plates (Costar, Cambridge, Mass.) (plating $2 \times 10^6$ T-cells per well). The antigen used to stimulate the cells was an organic extract of *Mycobacterium tuberculosis* (as described in Examples 2 and 3) at a 1/3,750 dilution. Briefly, a chloroform/methanol extraction based on Folch's method, which partitions most lipids into the organic phase and protein into the aqueous phase and interface, was used. Recombinant Interleukin-2 (rIL-2) was added (0.3 nM) after 4 days of culture and the cells were restimulated with antigen every 12 days.

Three rounds of stimulation led to the isolation of the CD1b-restricted TCR $\gamma\delta^+$ T-cell line called OGD1. Although the purified TCR $\gamma\delta^+$ T-cell population from which this T-cell line was isolated predominantly expressed the V$\delta$2 gene product (90%), FACS analysis of OGD1 with the monoclonal antibody TCR $\delta$1 ($\gamma\delta$TCR), $\delta$TCS1 (V$\delta$1 gene product) and BB3 (V$\delta$2 gene product) (available from T Cell Diagnostics, Cambridge, Mass.) demonstrated that the isolated T-cells expressed predominantly the V$\delta$1 gene product (FIG. 26A). This result suggests that this CD1 mediated stimulation is different than all previous demonstrated examples of stimulation of TCR $\gamma\delta^+$ T-cells by bacterial antigens, which invariably involve expansion of V$\gamma$2V$\delta$2 T-cells.

The restriction of the OGD1 cell line by CD1b was confirmed using anti-CD1b monoclonal antibody which blocked cytotoxicity of antigen pulsed CD1⁺ monocytes (FIG. 27) and also blocked specific proliferation of the OGD1 cell line to mycobacterial antigens present in the organic phase of chloroform/methanol extracted mycobacteria (FIG. 28). Further analysis of the fine specificity of this cell line demonstrated that OGD1 recognized saponified cord factor (SIGMA, St. Louis, Mo.) (i.e., mycolic acid, a lipid component of the mycobacterial cell wall) (FIG. 28).

CD8⁺ TCR $\alpha\beta^+$ T-cells Recognize Antigens Presented by the CD1 Molecule In order to determine if the CD1 molecule could serve as an antigen presenting molecule for CD8⁺ TCR $\gamma\delta^+$ bearing T-cells, experiments similar to those described above were performed using purified peripheral blood CD8⁺ T-cells instead of TCR $\gamma\delta^+$ T-cells. T-cells were purified with magnetic beads conjugated with anti-CD8 monoclonal antibody (Miltenyi Biotec, Sunnyvale, Calif.) and purity was assessed by FACS after subsequent staining with FITC conjugated monoclonal antibody OKT8 (anti-CD8$\alpha$). The culture protocol was similar to that for TCR $\gamma\delta^+$ T-cells. After three stimulations of these CD8⁺ T-cells with CD1⁺ monocytes pulsed with the organic extract of *Mycobacterium tuberculosis*, a cell line was obtained which was named OAB8. FACS analysis with FITC-conjugated anti-CD8 $\alpha$-chain (OKT8) and anti-CD8 $\beta$-chain (2ST8-5H7) monoclonal antibodies showed that the cell line was homogeneously positive for expression of the CD8 αβ. heterodimer. Staining with TCR αβ-specific monoclonal antibody BMA031 showed that cell line OAB8 was homogenously positive for TCR αβ. Proliferation assays confirmed the specificity of the OAB8 cell line to the organic extract of mycobacteria and showed that OAB8 recognized purified mycobacterial mycolic acid (FIG. 29). Moreover, antibody blocking experiments demonstrated that the OAB8 cell line was restricted by the CD1c molecule (FIG. 30), as anti-CD1c monoclonal antibody blocked its response whereas antibodies to CD1a, CD1b and MHC class I molecules had no effect.

These data indicate that in addition to the reactivity of $CD4^-8^-$ TCR $\alpha\beta^+$ bearing T-cells to CD1-restricted microbial antigens, other major T-cell populations are CD1 restricted. Because $CD8^+$ TCR $\alpha\beta^+$ bearing T-cells account for approximately 35% of all circulating T-cells and TCR γδ bearing T-cells account for another 5% of all T-cells, the potential magnitude of the CD1-restricted immune response is likely to be significant in a variety of immunological response and syndromes. Moreover, since these T-cell populations are known to secrete an array of cytokines and to mediate cytolytic activity, the effector capabilities of CD1-restricted $CD8^+$ TCR $\alpha\beta^+$ and TCR $\gamma\delta^+$ T-cells specific for nonpeptide antigens may play a critical role in host defense.

Incorporation by Reference

The entire text of all publications cited herein are entirely incorporated herein by reference.

What is claimed is:

1. A vaccine comprising:
    an amount of an isolated CD1-presented mycobacterial glycolipid antigen effective to induce a CD1-restricted immune response, wherein the mycobacterial glycolipid antigen is a lipoarabinomannan;
    an adjuvant; and
    a pharmaceutically acceptable carrier.

2. The vaccine of claim 1, wherein the vaccine is suitable for oral administration.

3. The vaccine of claim 1, wherein the mycobacterial glycolipid antigen is derived from a mycobacterium selected from the group consisting of *M. tuberculosis, M. bovis, M. leprae, M. fortuitum,* and *M. avium.*

4. The vaccine of claim 1, wherein the antigen has a structure that is capable of presentment by a CD1 molecule selected from the group consisting of CD1a, CD1b, CD1c, CD1d, and CD1e.

5. The vaccine of claim 1, wherein the CD1 molecule is selected from the group consisting of CD1a, CD1b, and CD1c.

6. The vaccine of claim 1, wherein the vaccine further comprises at least one cytokine which induces CD1 expression on antigen-presenting cells.

7. The vaccine of claim 6, wherein the cytokine is selected from the group consisting of IL-4 and GM-CSF.

8. A vaccine comprising:
    an amount of an isolated CD1-presented mycobacterial glycolipid antigen effective to induce a CD1-restricted immune response, wherein the mycobacterial glycolipid antigen is a lipoarabinomannan;
    an adjuvant; and
    a pharmaceutically acceptable carrier; and
    wherein the vaccine does not further comprise a non-CD1 presented antigen.

9. The vaccine of claim 8, wherein the vaccine is suitable for oral administration.

10. The vaccine of claim 8, wherein the myobacterial glycolipid antigen is derived from a mycobacterium selected from the group consisting of *M. tuberculosis, M. bovis, M. leprae, M. fortuitum,* and *M. avium.*

11. The vaccine of claim 8, wherein the antigen has a structure that is capable of presentment by a CD1 molecule selected from the group consisting of CD1a, CD1b, CD1c, CD1d, and CD1e.

12. The vaccine of claim 8, wherein the CD1 molecule is selected from the group consisting of CD1a, CD1b, and CD1c.

13. The vaccine of claim 8, wherein the vaccine further comprises at least one cytokine which induces CD1 expression on antigen-presenting cells.

14. The vaccine of claim 13, wherein the cytokine is selected from the group consisting of IL-4 and GM-CSF.

15. A vaccine comprising:
    an amount of an isolated CD1-presented mycobacterial glycolipid antigen effective to induce a CD1-restricted immune response, wherein the mycobacterial glycolipid antigen is a mycolic acid;
    an adjuvant; and
    a pharmaceutically acceptable carrier.

16. The vaccine of claim 15, wherein the vaccine is suitable for oral administration.

17. The vaccine of claim 15, wherein the mycobacterium is selected from the group consisting of *M. tuberculosis, M. bovis, M. leprae, M. fortuitum,* and *M. avium.*

18. The vaccine of claim 15, wherein the antigen has a structure that is capable of presentment by a CD1 molecule selected from the group consisting of CD1a, CD1b, CD1c, CD1d, and CD1e.

19. The vaccine of claim 15, wherein the CD1 molecule is selected from the group consisting of CD1a, CD1b, and CD1c.

20. The vaccine of claim 15, wherein the vaccine further comprises at least one cytokine which induces CD1 expression on antigen-presenting cells.

21. The vaccine of claim 15, wherein the cytokine is selected from the group consisting of IL-4 and GM-CSF.

22. A vaccine comprising:
    an amount of an isolated CD1-presented mycobacterial glycolipid antigen effective to induce a CD1-restricted immune response, wherein the mycobacterial glycolipid antigen is a mycolic acid;
    an adjuvant; and
    a pharmaceutically acceptable carrier; and
    wherein the vaccine does not further comprise a non-CD1 presented antigen.

23. The vaccine of claim 22, wherein the vaccine is suitable for oral administration.

24. The vaccine of claim 22, wherein the mycobacterium is selected from the group consisting of *M. tuberculosis, M. bovis, M. leprae, M. fortuitum,* and *M. avium.*

25. The vaccine of claim 22, wherein the antigen has a structure that is capable of presentment by a CD1 molecule selected from the group consisting of CD1a, CD1b, CD1c, CD1d, and CD1e.

26. The vaccine of claim 22, wherein the CD1 molecule is selected from the group consisting of CD1a, CD1b, and CD1c.

27. The vaccine of claim 22, wherein the vaccine further comprises at least one cytokine which induces CD1 expression on antigen-presenting cells.

28. The vaccine of claim 22, wherein the cytokine is selected from the group consisting of IL-4 and GM-CSF.

* * * * *